(12) United States Patent
Bardy et al.

(10) Patent No.: US 7,657,322 B2
(45) Date of Patent: Feb. 2, 2010

(54) SUBCUTANEOUS ELECTRODE WITH IMPROVED CONTACT SHAPE FOR TRANSTHORACIC CONDUCTION

(75) Inventors: Gust H. Bardy, Seattle, WA (US); Riccardo Cappato, Ferrara (IT); William J. Rissmann, Coto de Caza, CA (US); Gary H. Sanders, Rancho Santa Margarita, CA (US)

(73) Assignee: Cameron Health, Inc., San Clemente, CA (US)

( * ) Notice: Subject to any disclaimer, the term of this patent is extended or adjusted under 35 U.S.C. 154(b) by 433 days.

(21) Appl. No.: 11/429,089

(22) Filed: May 5, 2006

(65) Prior Publication Data

US 2006/0206181 A1 Sep. 14, 2006

Related U.S. Application Data

(63) Continuation of application No. 10/013,980, filed on Nov. 5, 2001, now Pat. No. 7,065,410, and a continuation-in-part of application No. 09/941,814, filed on Aug. 27, 2001, now abandoned, and a continuation-in-part of application No. 09/663,606, filed on Sep. 18, 2000, now Pat. No. 6,647,292, which is a continuation-in-part of application No. 09/663,607, filed on Sep. 18, 2000, now Pat. No. 6,721,597.

(51) Int. Cl.
*A61N 1/05* (2006.01)
(52) U.S. Cl. .................. 607/116; 607/129; 607/149
(58) Field of Classification Search .................. None
See application file for complete search history.

(56) References Cited

U.S. PATENT DOCUMENTS

| | | | |
|---|---|---|---|
| 3,653,387 A | 4/1972 | Ceier |
| 3,710,374 A | 1/1973 | Kelly |
| 3,828,766 A | 8/1974 | Krasnow |
| 3,911,925 A | 10/1975 | Tillery, Jr. |
| 4,010,758 A | 3/1977 | Rockland et al. |
| 4,030,509 A | 6/1977 | Heilman et al. |
| 4,157,720 A | 6/1979 | Greatbatch |
| 4,191,942 A | 3/1980 | Long |
| 4,223,678 A | 9/1980 | Langer et al. |

(Continued)

FOREIGN PATENT DOCUMENTS

DE 298 01 807 U1 7/1998

(Continued)

OTHER PUBLICATIONS

Bardy, Gust H. et al., "Multicenter Experience with a Pectoral Unipolar Implantable Cardioverter-Defibrillator," *JACC*, Aug. 1996, vol. 28, No. 2, pp. 400-410.

(Continued)

*Primary Examiner*—Kennedy J Schaetzle
(74) *Attorney, Agent, or Firm*—Pramudji Wendt & Tran, LLP; Ari Pramudji; Mark Schroeder

(57) ABSTRACT

One embodiment of the present invention provides a lead electrode assembly for use with an implantable cardioverter-defibrillator subcutaneously implanted outside the ribcage between the third and twelfth ribs comprising the electrode.

10 Claims, 38 Drawing Sheets

U.S. PATENT DOCUMENTS

| | | |
|---|---|---|
| 4,248,237 A | 2/1981 | Kenny |
| 4,291,707 A | 9/1981 | Heilman et al. |
| 4,314,095 A | 2/1982 | Moore et al. |
| 4,402,322 A | 9/1983 | Duggan |
| 4,407,288 A | 10/1983 | Langer et al. |
| 4,424,818 A | 1/1984 | Doring et al. |
| 4,450,527 A | 5/1984 | Sramek |
| 4,567,900 A | 2/1986 | Moore |
| 4,602,637 A | 7/1986 | Elmqvist et al. |
| 4,603,705 A | 8/1986 | Speicher et al. |
| 4,693,253 A | 9/1987 | Adams |
| 4,757,817 A | 7/1988 | Healy |
| 4,765,341 A | 8/1988 | Mower et al. |
| 4,800,883 A | 1/1989 | Winstrom |
| 4,830,005 A | 5/1989 | Woskow |
| 4,944,300 A | 7/1990 | Saksena |
| 5,020,544 A | 6/1991 | Dahl et al. |
| 5,105,810 A | 4/1992 | Collins et al. |
| 5,109,842 A | 5/1992 | Adinolfi |
| 5,129,392 A | 7/1992 | Bardy et al. |
| 5,133,353 A | 7/1992 | Hauser |
| 5,144,946 A | 9/1992 | Weinberg et al. |
| 5,184,616 A | 2/1993 | Weiss |
| 5,191,901 A | 3/1993 | Dahl et al. |
| 5,203,348 A | 4/1993 | Dahl et al. |
| 5,230,337 A | 7/1993 | Dahl et al. |
| 5,255,692 A | 10/1993 | Neubauer et al. |
| 5,261,400 A | 11/1993 | Bardy |
| 5,300,106 A | 4/1994 | Dahl et al. |
| 5,306,291 A | 4/1994 | Kroll et al. |
| 5,331,966 A | 7/1994 | Bennett et al. |
| 5,342,407 A | 8/1994 | Dahl et al. |
| 5,354,328 A | 10/1994 | Doan et al. |
| 5,366,496 A | 11/1994 | Dahl et al. |
| 5,376,103 A | 12/1994 | Anderson et al. |
| 5,376,104 A | 12/1994 | Sakai et al. |
| 5,385,574 A | 1/1995 | Hauser et al. |
| 5,391,200 A | 2/1995 | KenKnight et al. |
| 5,405,363 A | 4/1995 | Kroll et al. |
| 5,411,539 A | 5/1995 | Neisz |
| 5,411,547 A | 5/1995 | Causey, III |
| 5,413,591 A | 5/1995 | Knoll |
| 5,423,326 A | 6/1995 | Wang et al. |
| 5,431,681 A | 7/1995 | Helland |
| 5,476,503 A | 12/1995 | Yang |
| 5,509,923 A | 4/1996 | Middleman et al. |
| 5,509,928 A | 4/1996 | Acken |
| 5,531,765 A | 7/1996 | Pless |
| 5,531,766 A | 7/1996 | Kroll et al. |
| 5,534,019 A | 7/1996 | Paspa |
| 5,534,022 A | 7/1996 | Hoffmann et al. |
| 5,597,956 A | 1/1997 | Ito et al. |
| 5,601,607 A | 2/1997 | Adams |
| 5,603,732 A | 2/1997 | Dahl et al. |
| 5,618,287 A | 4/1997 | Fogarty et al. |
| 5,620,477 A | 4/1997 | Pless et al. |
| 5,643,328 A | 7/1997 | Cooke et al. |
| 5,645,586 A | 7/1997 | Meltzer |
| 5,658,317 A | 8/1997 | Haefner et al. |
| 5,658,321 A | 8/1997 | Fayram et al. |
| 5,674,260 A | 10/1997 | Weinberg |
| 5,690,648 A | 11/1997 | Fogarty et al. |
| 5,690,683 A | 11/1997 | Haefner et al. |
| 5,697,953 A | 12/1997 | Kroll et al. |
| 5,709,644 A | 1/1998 | Bush |
| 5,713,926 A | 2/1998 | Hauser et al. |
| 5,766,226 A | 6/1998 | Pedersen |
| 5,776,169 A | 7/1998 | Schroeppel |
| 5,814,090 A | 9/1998 | Latterell et al. |
| 5,836,976 A | 11/1998 | Min et al. |
| 5,895,414 A | 4/1999 | Sanchez-Zambrano |
| 5,919,211 A | 7/1999 | Adams |
| 5,919,222 A | 7/1999 | Hjelle et al. |
| 5,925,069 A | 7/1999 | Graves et al. |
| 5,935,154 A | 8/1999 | Westlund |
| 5,941,904 A | 8/1999 | Johnston et al. |
| 6,014,586 A | 1/2000 | Weinberg et al. |
| 6,026,325 A | 2/2000 | Weinberg et al. |
| 6,038,484 A | 3/2000 | Kuzma |
| 6,058,328 A | 5/2000 | Levine et al. |
| 6,093,173 A | 7/2000 | Balceta et al. |
| 6,095,987 A | 8/2000 | Shmulewitz et al. |
| 6,112,124 A | 8/2000 | Loeb |
| H1905 H | 10/2000 | Hill |
| 6,128,531 A | 10/2000 | Campbell-Smith |
| 6,144,866 A | 11/2000 | Miesel et al. |
| 6,185,450 B1 | 2/2001 | Seguine et al. |
| 6,256,541 B1 | 7/2001 | Heil et al. |
| 6,272,385 B1 | 8/2001 | Bishay et al. |
| 6,411,844 B1 | 6/2002 | Kroll et al. |
| 6,539,260 B1 | 3/2003 | Schloss |
| 6,647,292 B1 | 11/2003 | Bardy et al. |
| 6,721,597 B1 | 4/2004 | Bardy et al. |
| 6,754,528 B2 | 6/2004 | Bardy et al. |
| 6,778,860 B2 | 8/2004 | Ostroff et al. |
| 6,788,974 B2 | 9/2004 | Bardy et al. |
| 6,834,204 B2 | 12/2004 | Ostroff et al. |
| 6,856,835 B2 | 2/2005 | Bardy et al. |
| 6,865,417 B2 | 3/2005 | Rissmann et al. |
| 6,866,044 B2 | 3/2005 | Bardy et al. |
| 6,927,721 B2 | 8/2005 | Ostroff et al. |
| 6,937,907 B2 | 8/2005 | Bardy et al. |
| 6,950,705 B2 | 9/2005 | Bardy et al. |
| 6,952,608 B2 | 10/2005 | Ostroff |
| 6,952,610 B2 | 10/2005 | Ostroff et al. |
| 6,954,670 B2 | 10/2005 | Ostroff |
| 6,988,003 B2 | 1/2006 | Bardy et al. |
| 2001/0027330 A1 | 10/2001 | Sullivan et al. |
| 2002/0035381 A1 | 3/2002 | Bardy et al. |

FOREIGN PATENT DOCUMENTS

| | | |
|---|---|---|
| EP | 0 095 727 A1 | 12/1983 |
| EP | 0 316 616 A2 | 5/1989 |
| EP | 0 316 616 A3 | 5/1989 |
| EP | 0 347 353 A1 | 12/1989 |
| EP | 0 517 494 A3 | 12/1992 |
| EP | 0 517 494 B1 | 12/1992 |
| EP | 0 518 599 A2 | 12/1992 |
| EP | 0 518 599 B1 | 12/1992 |
| EP | 0 536 873 B1 | 4/1993 |
| EP | 0 586 858 B1 | 3/1994 |
| EP | 0 627 237 A1 | 12/1994 |
| EP | 0 641 573 A2 | 3/1995 |
| EP | 0 641 573 A3 | 3/1995 |
| EP | 0 677 301 A1 | 10/1995 |
| EP | 0 917 887 A1 | 5/1999 |
| EP | 0 923 130 A1 | 6/1999 |
| EP | 1 000 634 A1 | 5/2000 |
| WO | WO 93/19809 A1 | 10/1993 |
| WO | WO 97/29802 A2 | 8/1997 |
| WO | WO 98/25349 A1 | 6/1998 |
| WO | WO 99/03534 A1 | 1/1999 |
| WO | WO 99/37362 A1 | 7/1999 |
| WO | WO 99/53991 A1 | 10/1999 |
| WO | WO 00/41766 A1 | 7/2000 |
| WO | WO 00/50120 A1 | 8/2000 |
| WO | WO 01/43649 A1 | 6/2001 |
| WO | WO 01/56166 A2 | 8/2001 |
| WO | WO 02/22208 A2 | 3/2002 |
| WO | WO 02/22208 A3 | 3/2002 |
| WO | WO 02/24275 A2 | 3/2002 |
| WO | WO 02/24275 A3 | 3/2002 |
| WO | WO 02/068046 A1 | 9/2002 |

WO WO 03/018121 A2 3/2003

OTHER PUBLICATIONS

Friedman, Richard A. et al., "Implantable Defibrillators In Children: From Whence to Shock," *Journal of Cardiovascular Electrophysiology*, vol. 12, No. 3, Mar. 2001, pp. 361-362.

Higgins, Steven L. et al., "The First Year Experience with the Dual Chamber ICD," *PACE*, Jan. 2000, vol. 23, pp. 18-25.

Gradaus, Rainer et al., "Nonthoracotomy Implantable Cardioverter Defibrillator Placement in Children: Use of Subcutaneous Array Leads and Abdominally Placed Implantable Cardioverter Defibrillators in Children," *Journal of Cardiovascular Electrophysiology*, vol. 12, No. 3, Mar. 2001, pp. 356-360.

Mirowski, M. et al., "Automatic Detection and Defibrillation of Lethal Arrhythmias—A New Concept," *JAMA*, vol. 213, No. 4, Jul. 27, 1970, pp. 615-616.

Olson, Walter H. et al., "Onset and Stability for Ventricular Tachyarrhythmia Detection in an Implantable Pacer-Cardioverter-Defibrillator," *IEEE*, (1987) pp. 167-170.

Schuder, John C., "Completely Implanted Defibrillator," *JAMA*, vol. 214, No. 6, Nov. 9, 1970. p. 1123 (single sheet).

Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95-124.

Schuder, John C. et al., "Experimental Ventricular Defibrillation with an Automatic and Completely Implanted System," *Trans. Amer. Soc. Artif. Int. Organs*, vol. XVI (1970) pp. 207-212.

Schuder, John C. et al., "Standby Implanted Defibrillators," *Arch Intern. Med*, vol. 127, Feb. 1971, p. 317 (single sheet).

Schuder, John C. et al., "Transthoracic Ventricular Defibrillation in the Dog with Truncated and Untruncated Exponential Stimuli," *IEEE Transactions on Bio-Medical Engineering*, vol. BME-18, No. 6, Nov. 1971, pp. 410-415.

Schwacke, H. et al., "Komplikationen mit Sonden bei 340 Patienten mit einem Implantierbaren Kardioverter/Defibrillator," *Z Kardiol* (1999) vol. 88, No. 8, pp. 559-565.

Tietze U. et al., "Halbleiter-Schaltungstechnik," © Springer-Verlag (Berlin, Germany), (1991), pp. 784-786.

Valenzuela, Terrence D. et al., "Outcomes of Rapid Defibrillation by Security Officers After Cardiac Arrest in Casinos," *The New England Journal of Medicine*, Oct. 26, 2000, vol. 343, No. 17, pp. 1206-1209.

Walters, R.A. et al., "Analog to Digital Conversion Techniques in Implantable Devices," *Annual International Conference of the IEEE Engineering in Medicine and Biology Society*, vol. 13 No. 4 (1991) p. 1674-1676.

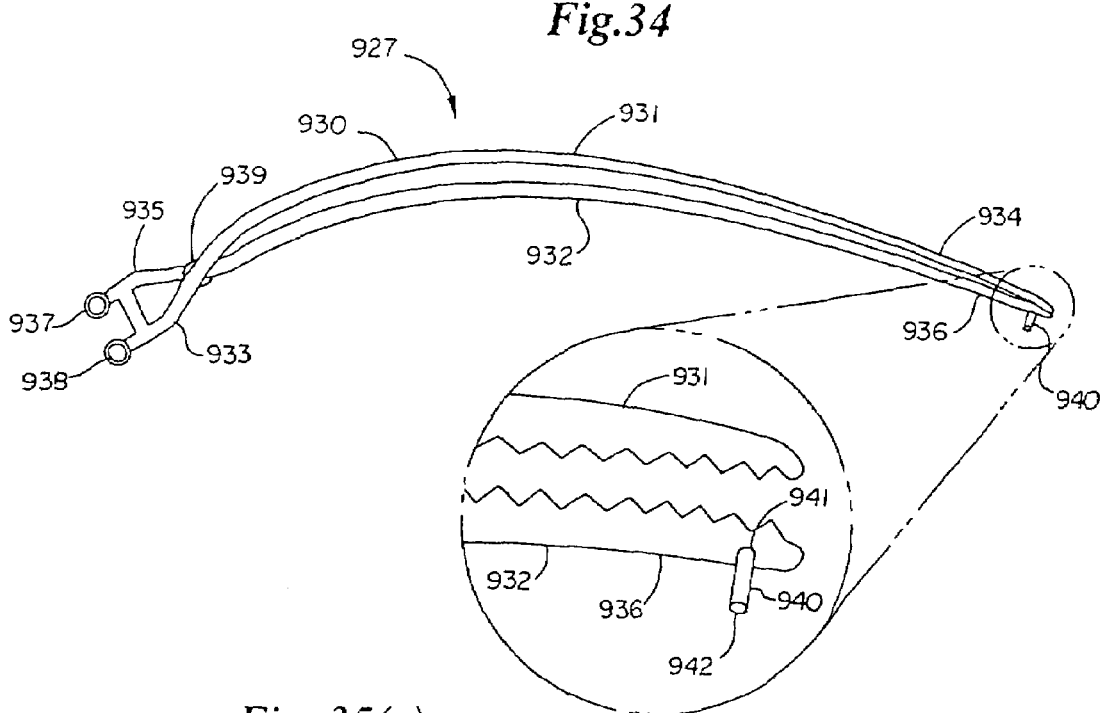
Fig. 34
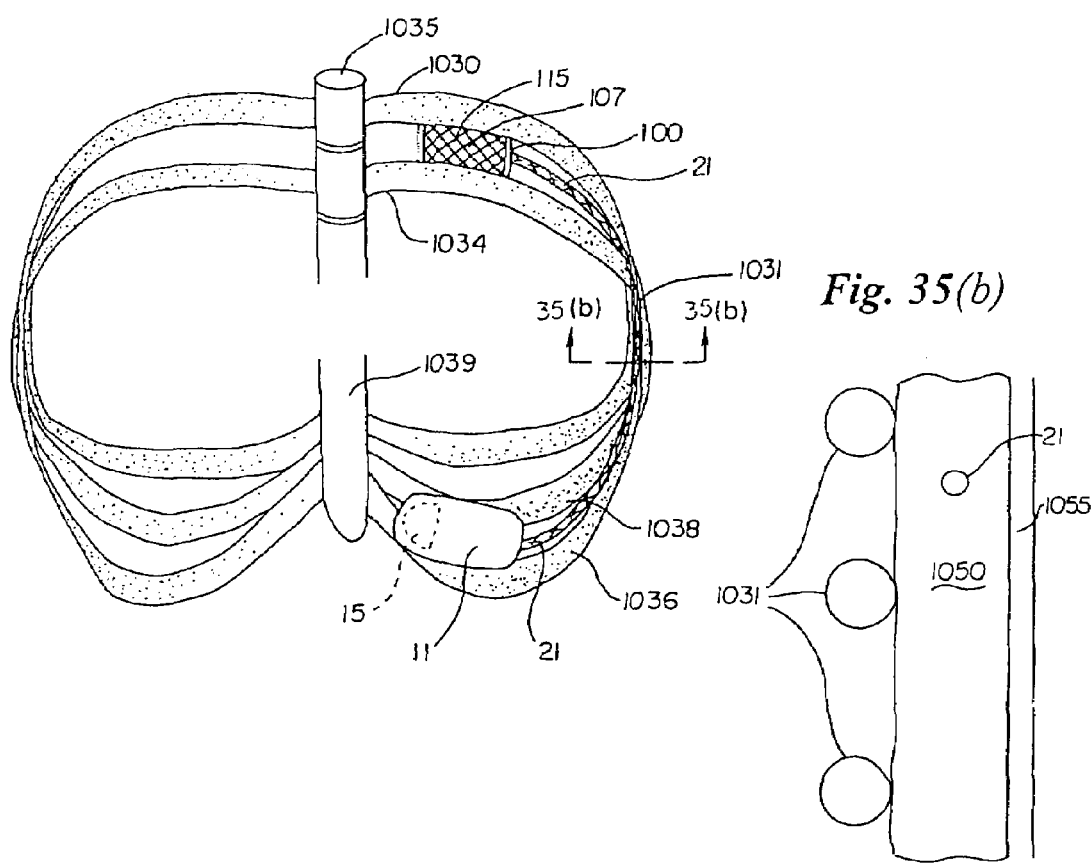
Fig. 35(a)
Fig. 35(b)

SUBCUTANEOUS ELECTRODE WITH IMPROVED CONTACT SHAPE FOR TRANSTHORACIC CONDUCTION

CROSS-REFERENCE TO RELATED APPLICATIONS

This application is a continuation of U.S. patent application Ser. No. 10/013,980, filed Nov. 5, 2001 and now U.S. Pat. No. 7,065,410; which is a continuation-in-part of U.S. patent application Ser. No. 09/663,607, filed Sept. 18, 2000 and now U.S. Pat. No. 6,721,597; and a continuation-in-part of U.S. patent application Ser. No. 09/663,606, filed Sept. 18, 2000 and now U.S. Pat. No. 6,647,292; and a continuation-in-part of U.S. patent application Ser. No. 09/941,814, filed Aug. 27, 2001, abandoned, the entire disclosures of which are all hereby incorporated by reference.

FIELD OF THE INVENTION

The present invention relates to an apparatus and method for performing electrical cardioversion/defibrillation and optional pacing of the heart via a totally subcutaneous non-transvenous system.

BACKGROUND OF THE INVENTION

Defibrillation/cardioversion is a technique employed to counter arrhythmic heart conditions including some tachycardias in the atria and/or ventricles. Typically, electrodes are employed to stimulate the heart with electrical impulses or shocks, of a magnitude substantially greater than pulses used in cardiac pacing. Shocks used for defibrillation therapy can comprise a biphasic truncated exponential waveform. As for pacing, a constant current density is desired to reduce or eliminate variability due to the electrode/tissue interface.

Defibrillation/cardioversion systems include body implantable electrodes that are connected to a hermetically sealed container housing the electronics, battery supply and capacitors. The entire system is referred to as implantable cardioverter/defibrillators (ICDs). The electrodes used in ICDs can be in the form of patches applied directly to epicardial tissue, or, more commonly, are on the distal regions of small cylindrical insulated catheters that typically enter the subclavian venous system, pass through the superior vena cava, and into one or more endocardial areas of the heart. Such electrode systems are called intravascular or transvenous electrodes. U.S. Pat. Nos. 4,603,705; 4,693,253; 4,944,300; and 5,105,810, the disclosures of which are all incorporated herein by reference, disclose intravascular or transvenous electrodes, employed either alone, in combination with other intravascular or transvenous electrodes, or in combination with an epicardial patch or subcutaneous electrodes. Compliant epicardial defibrillator electrodes are disclosed in U.S. Pat. Nos. 4,567,900 and 5,618,287, the disclosures of which are incorporated herein by reference. A sensing epicardial electrode configuration is disclosed in U.S. Pat No. 5,476,503, the disclosure of which is incorporated herein by reference.

In addition to epicardial and transvenous electrodes, subcutaneous electrode systems have also been developed. For example, U.S. Pat. Nos. 5,342,407 and 5,603,732, the disclosures of which are incorporated herein by reference, teach the use of a pulse monitor/generator surgically implanted into the abdomen and subcutaneous electrodes implanted in the thorax. This system is far more complicated to use than current ICD systems using transvenous lead systems together with an active can electrode and therefore it has no practical use. It has in fact never been used because of the surgical difficulty of applying such a device (3 incisions), the impractical abdominal location of the generator and the electrically poor sensing and defibrillation aspects of such a system.

Recent efforts to improve the efficiency of ICDs have led manufacturers to produce ICDs which are small enough to be implanted in the pectoral region. In addition, advances in circuit design have enabled the housing of the ICD to form a subcutaneous electrode. Some examples of ICDs in which the housing of the ICD serves as an optional additional electrode are described in U.S. Pat. Nos. 5,133,353; 5,261,400; 5,620,477; and 5,658,321, the disclosures of which are incorporated herein by reference.

ICDs are now an established therapy for the management of life threatening cardiac rhythm disorders, primarily ventricular fibrillation (V-Fib). ICDs are very effective at treating V-Fib, but are therapies that still require significant surgery.

As ICD therapy becomes more prophylactic in nature and used in progressively less ill individuals, especially children at risk of cardiac arrest, the requirement of ICD therapy to use intravenous catheters and transvenous leads is an impediment to very long term management as most individuals will begin to develop complications related to lead system malfunction sometime in the 5-10 year time frame, often earlier. In addition, chronic transvenous lead systems, their reimplantation and removals, can damage major cardiovascular venous systems and the tricuspid valve, as well as result in life threatening perforations of the great vessels and heart. Consequently, use of transvenous lead systems, despite their many advantages, are not without their chronic patient management limitations in those with life expectancies of >5 years. The problem of lead complications is even greater in children where body growth can substantially alter transvenous lead function and lead to additional cardiovascular problems and revisions. Moreover, transvenous ICD systems also increase cost and require specialized interventional rooms and equipment as well as special skill for insertion. These systems are typically implanted by cardiac electrophysiologists who have had a great deal of extra training.

In addition to the background related to ICD therapy, the present invention requires a brief understanding of a related therapy, the automatic external defibrillator (AED). AEDs employ the use of cutaneous patch electrodes, rather than implantable lead systems, to effect defibrillation under the direction of a bystander user who treats the patient suffering from V-Fib with a portable device containing the necessary electronics and power supply that allows defibrillation. AEDs can be nearly as effective as an ICD for defibrillation if applied to the victim of ventricular fibrillation promptly, i.e., within 2 to 3 minutes of the onset of the ventricular fibrillation.

AED therapy has great appeal as a tool for diminishing the risk of death in public venues such as in air flight. However, an AED must be used by another individual, not the person suffering from the potential fatal rhythm. It is more of a public health tool than a patient-specific tool like an ICD. Because >75% of cardiac arrests occur in the home, and over half occur in the bedroom, patients at risk of cardiac arrest are often alone or asleep and cannot be helped in time with an AED. Moreover, its success depends to a reasonable degree on an acceptable level of skill and calm by the bystander user.

What is needed therefore, especially for children and for prophylactic long term use for those at risk of cardiac arrest, is a combination of the two forms of therapy which would provide prompt and near-certain defibrillation, like an ICD, but without the long-term adverse sequelae of a transvenous lead system while simultaneously using most of the simpler and lower cost technology of an AED. What is also needed is a cardioverter/defibrillator that is of simple design and can be comfortably implanted in a patient for many years.

SUMMARY OF THE INVENTION

One embodiment of the present invention provides a lead electrode assembly for use with an implantable cardioverter-defibrillator subcutaneously implanted outside the ribcage between the third and twelfth ribs comprising an electrode.

BRIEF DESCRIPTION OF THE DRAWINGS

For a better understanding of the invention, reference is now made to the drawings where like numerals represent similar objects throughout the figures where:

FIG. 34 is a perspective view of a custom hemostat for lead electrode assembly implantation;

FIG. 35(a) is a perspective view of a patient's ribcage showing the orientation of the components in an implanted S-ICD system;

FIG. 35(b) is a cross-sectional side plan view of a patient's rib cage, skin, fat and the lead of the lead electrode assembly;

DETAILED DESCRIPTION

Figure 1:
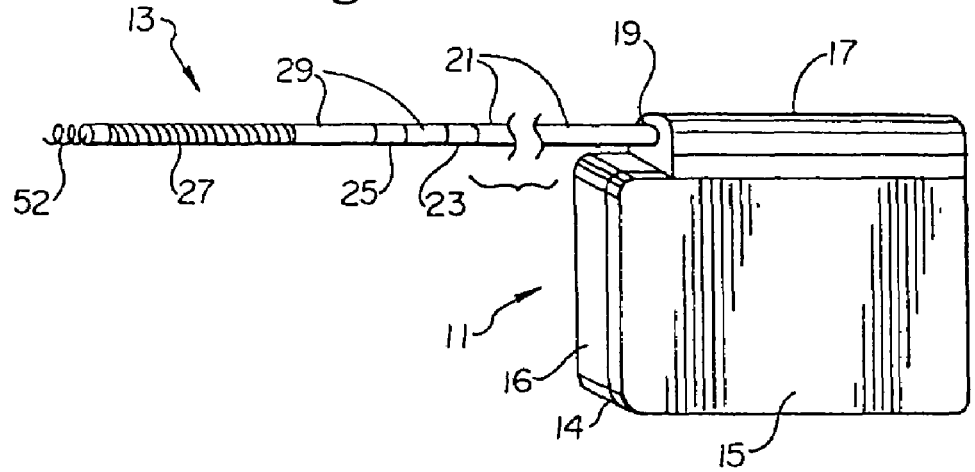
FIG. 1 is a schematic view of a Subcutaneous ICD (S-ICD) of the present invention.

Turning now to FIG. 1, the S-ICD of the present invention is illustrated. The S-ICD consists of an electrically active canister 11 and a subcutaneous electrode 13 attached to the canister. The canister has an electrically active surface 15 that is electrically insulated from the electrode connector block 17 and the canister housing 16 via insulating area 14. The canister can be similar to numerous electrically active canisters commercially available in that the canister will contain a battery supply, capacitor and operational circuitry. Alternatively, the canister can be thin and elongated to conform to the intercostal space. The circuitry will be able to monitor cardiac rhythms for tachycardia and fibrillation, and if detected, will initiate charging the capacitor and then delivering cardioversion/defibrillation energy through the active surface of the housing and to the subcutaneous electrode. Examples of such circuitry are described in U.S. Pat. Nos. 4,693,253 and 5,105,810, the entire disclosures of which are herein incorporated by reference. The canister circuitry can provide cardioversion/defibrillation energy in different types of waveforms. In one embodiment, a 100 uF biphasic waveform is used of approximately 10-20 ms total duration and with the initial phase containing approximately ⅔ of the energy, however, any type of waveform can be utilized such as monophasic, biphasic, multiphasic or alternative waveforms as is known in the art.

In addition to providing cardioversion/defibrillation energy, the circuitry can also provide transthoracic cardiac pacing energy. The optional circuitry will be able to monitor the heart for bradycardia and/or tachycardia rhythms. Once a bradycardia or tachycardia rhythm is detected, the circuitry can then deliver appropriate pacing energy at appropriate intervals through the active surface and the subcutaneous electrode. Pacing stimuli can be biphasic in one embodiment and similar in pulse amplitude to that used for conventional transthoracic pacing.

This same circuitry can also be used to deliver low amplitude shocks on the T-wave for induction of ventricular fibrillation for testing S-ICD performance in treating V-Fib as is described in U.S. Pat. No. 5,129,392, the entire disclosure of which is hereby incorporated by reference. Also the circuitry can be provided with rapid induction of ventricular fibrillation or ventricular tachycardia using rapid ventricular pacing. Another optional way for inducing ventricular fibrillation would be to provide a continuous low voltage, i.e., about 3 volts, across the heart during the entire cardiac cycle.

Another optional aspect of the present invention is that the operational circuitry can detect the presence of atrial fibrillation as described in Olson, W. et al. "Onset And Stability For Ventricular Tachyarrhythmia Detection in an Implantable Pacer-Cardioverter-Defibrillator," Computers in Cardiology (1986) pp. 167-170. Detection can be provided via R-R Cycle length instability detection algorithms. Once atrial fibrillation has been detected, the operational circuitry will then provide QRS synchronized atrial defibrillation/cardioversion using the same shock energy and waveshape characteristics used for ventricular defibrillation/cardioversion.

The sensing circuitry will utilize the electronic signals generated from the heart and will primarily detect QRS waves. In one embodiment, the circuitry will be programmed to detect only ventricular tachycardias or fibrillations. The detection circuitry will utilize in its most direct form, a rate detection algorithm that triggers charging of the capacitor once the ventricular rate exceeds some predetermined level for a fixed period of time: for example, if the ventricular rate exceeds 240 bpm on average for more than 4 seconds. Once the capacitor is charged, a confirmatory rhythm check would ensure that the rate persists for at least another 1 second before discharge. Similarly, termination algorithms could be instituted that ensure that a rhythm less than 240 bpm persisting for at least 4 seconds before the capacitor charge is drained to an internal resistor. Detection, confirmation and termination algorithms as are described above and in the art can be modulated to increase sensitivity and specificity by examining QRS beat-to-beat uniformity, QRS signal frequency content, R-R interval stability data, and signal amplitude characteristics all or part of which can be used to increase or decrease both sensitivity and specificity of S-ICD arrhythmia detection function.

In addition to use of the sense circuitry for detection of V-Fib or V-Tach by examining the QRS waves, the sense circuitry can check for the presence or the absence of respiration. The respiration rate can be detected by monitoring the impedance across the thorax using subthreshold currents delivered across the active can and the high voltage subcutaneous lead electrode and monitoring the frequency in undulation in the waveform that results from the undulations of transthoracic impedance during the respiratory cycle. If there is no undulation, then the patient is not respiring and this lack of respiration can be used to confirm the QRS findings of cardiac arrest. The same technique can be used to provide information about the respiratory rate or estimate cardiac output as described in U.S. Pat. Nos. 6,095,987; 5,423,326; and 4,450,527, the entire disclosures of which are incorporated herein by reference.

The canister of the present invention can be made out of titanium alloy or other presently preferred electrically active canister designs. However, it is contemplated that a malleable canister that can conform to the curvature of the patient's chest will be preferred. In this way the patient can have a comfortable canister that conforms to the shape of the patient's rib cage. Examples of conforming canisters are provided in U.S. Pat. No. 5,645,586, the entire disclosure of which is herein incorporated by reference. Therefore, the canister can be made out of numerous materials such as medical grade plastics, metals, and alloys. In the preferred embodiment, the canister is smaller than 60 cc volume having a weight of less than 100 gms for long term wearability, especially in children. The canister and the lead of the S-ICD can also use fractal or wrinkled surfaces to increase surface area to improve defibrillation capability. Because of the primary prevention role of the therapy and the likely need to reach energies over 40 Joules, a feature of one embodiment is that the charge time for the therapy is intentionally left relatively long to allow capacitor charging within the limitations of device size. Examples of small ICD housings are disclosed in U.S. Pat. Nos. 5,597,956 and 5,405,363, the entire disclosures of which are herein incorporated by reference.

Figure 2:
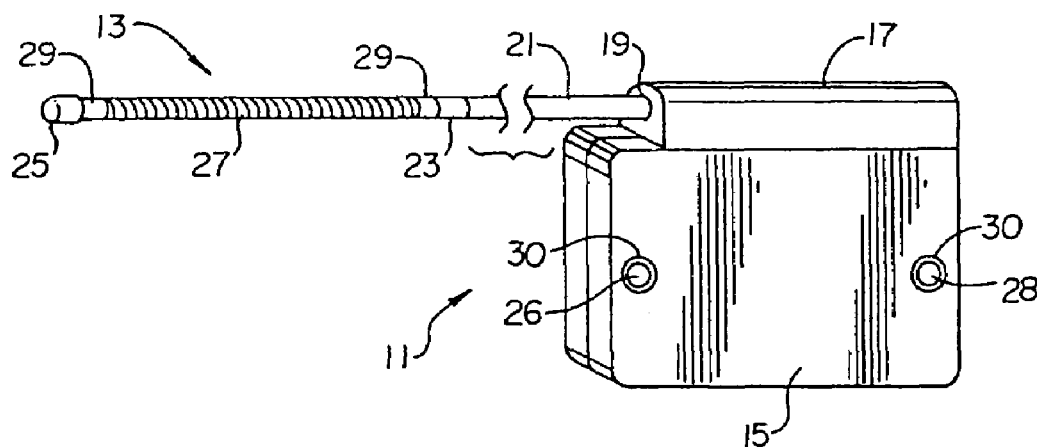
FIG. 2 is a schematic view of an alternate embodiment of a subcutaneous electrode of the present invention.
Figure 3:
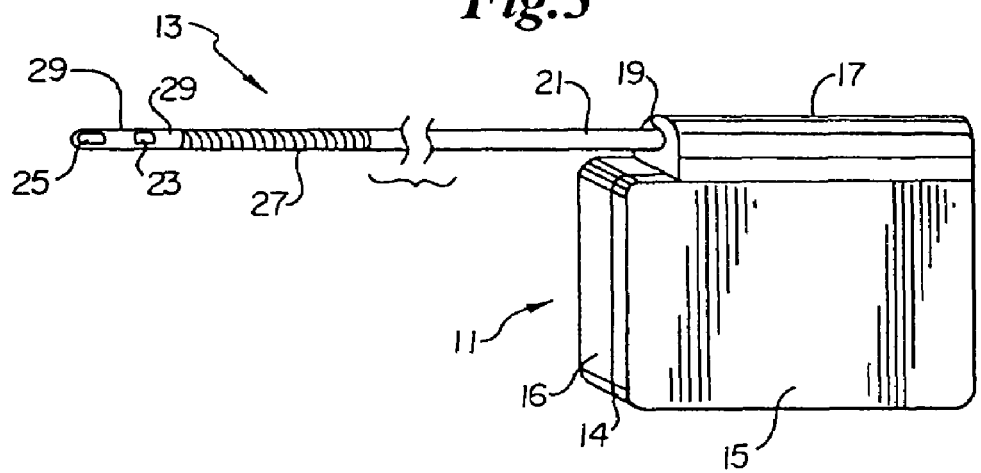
FIG. 3 is a schematic view of an alternate embodiment of a subcutaneous electrode of the present invention.

Different subcutaneous electrodes 13 of the present invention are illustrated in FIGS. 1-3. Turning to FIG. 1, the lead 21 for the subcutaneous electrode is preferably composed of silicone or polyurethane insulation. The electrode is connected to the canister at its proximal end via connection port 19 which is located on an electrically insulated area 17 of the canister. The electrode illustrated is a composite electrode with three different electrodes attached to the lead. In the embodiment illustrated, an optional anchor segment 52 is attached at the most distal end of the subcutaneous electrode for anchoring the electrode into soft tissue such that the electrode does not dislodge after implantation.

The most distal electrode on the composite subcutaneous electrode is a coil electrode 27 that is used for delivering the high voltage cardioversion/defibrillation energy across the heart. The coil cardioversion/defibrillation electrode is about 5-10 cm in length. Proximal to the coil electrode are two sense electrodes, a first sense electrode 25 is located proximally to the coil electrode and a second sense electrode 23 is located proximally to the first sense electrode. The sense electrodes are spaced far enough apart to be able to have good QRS detection. This spacing can range from 1 to 10 cm with 4 cm being presently preferred. The electrodes may or may not be circumferential with the preferred embodiment. Having the electrodes non-circumferential and positioned outward, toward the skin surface, is a means to minimize muscle artifact and enhance QRS signal quality. The sensing electrodes are electrically isolated from the cardioversion/defibrillation electrode via insulating areas 29. Similar types of cardioversion/defibrillation electrodes are currently commercially available in a transvenous configuration. For example, U.S. Pat. No. 5,534,022, the entire disclosure of which is herein incorporated by reference, discloses a composite electrode with a coil cardioversion/defibrillation electrode and sense electrodes. Modifications to this arrangement are contemplated within the scope of the invention. One such modification is illustrated in FIG. 2 where the two sensing electrodes 25 and 23 are non-circumferential sensing electrodes and one is located at the distal end, the other is located proximal thereto with the coil electrode located in between the two sensing electrodes. In this embodiment, the sense electrodes are spaced about 6 to about 12 cm apart depending on the length of the coil electrode used. FIG. 3 illustrates yet a further embodiment where the two sensing electrodes are located at the distal end to the composite electrode with the coil electrode located proximally thereto. Other possibilities exist and are contemplated within the present invention, for example, having only one sensing electrode, either proximal or distal to the coil cardioversion/defibrillation electrode with the coil serving as both a sensing electrode and a cardioversion/defibrillation electrode.

It is also contemplated within the scope of the invention that the sensing of QRS waves (and transthoracic impedance) can be carried out via sense electrodes on the canister housing or in combination with the cardioversion/defibrillation coil electrode and/or the subcutaneous lead sensing electrode(s). In this way, sensing could be performed via the one coil electrode located on the subcutaneous electrode and the active surface on the canister housing. Another possibility would be to have only one sense electrode located on the subcutaneous electrode and the sensing would be performed by that one electrode and either the coil electrode on the subcutaneous electrode or by the active surface of the canister. The use of sensing electrodes on the canister would eliminate the need for sensing electrodes on the subcutaneous electrode. It is also contemplated that the subcutaneous electrode would be provided with at least one sense electrode, the canister with at least one sense electrode, and if multiple sense electrodes are used on either the subcutaneous electrode and/or the canister, that the best QRS wave detection combination will be identified when the S-ICD is implanted and this combination can be selected, activating the best sensing arrangement from all the existing sensing possibilities. Turning again to FIG. 2, two sensing electrodes 26 and 28 are located on the electrically active surface 15 with electrical insulator rings 30 placed between the sense electrodes and the active surface. These canister sense electrodes could be switched off and electrically insulated during and shortly after defibrillation/cardioversion shock delivery. The canister sense electrodes may also be placed on the electrically inactive surface of the canister. In the embodiment of FIG. 2, there are actually four sensing electrodes, two on the subcutaneous lead and two on the canister. In the preferred embodiment, the ability to change which electrodes are used for sensing would be a programmable feature of the S-ICD to adapt to changes in the patient physiology and size (in the case of children) over time. The programming could be done via the use of physical switches on the canister, or as presently preferred, via the use of a programming wand or via a wireless connection to program the circuitry within the canister.

The canister could be employed as either a cathode or an anode of the S-ICD cardioversion/defibrillation system. If the canister is the cathode, then the subcutaneous coil electrode would be the anode. Likewise, if the canister is the anode, then the subcutaneous electrode would be the cathode.

The active canister housing will provide energy and voltage intermediate to that available with ICDs and most AEDs. The typical maximum voltage necessary for ICDs using most biphasic waveforms is approximately 750 Volts with an associated maximum energy of approximately 40 Joules. The typical maximum voltage necessary for AEDs is approximately 2000-5000 Volts with an associated maximum energy of approximately 200-360 Joules depending upon the model and waveform used. The S-ICD and the US-ICD of the present invention use maximum voltages in the range of about 50 to about 3500 Volts and is associated with energies of about 0.5 to about 350 Joules. The capacitance of the devices can range from about 25 to about 200 micro farads.

The sense circuitry contained within the canister is highly sensitive and specific for the presence or absence of life threatening ventricular arrhythmias. Features of the detection algorithm are programmable and the algorithm is focused on the detection of V-FIB and high rate V-TACH (>240 bpm). Although the S-ICD of the present invention may rarely be used for an actual life threatening event, the simplicity of design and implementation allows it to be employed in large populations of patients at modest risk with modest cost by non-cardiac electrophysiologists. Consequently, the S-ICD of the present invention focuses mostly on the detection and therapy of the most malignant rhythm disorders. As part of the detection algorithm's applicability to children, the upper rate range is programmable upward for use in children, known to have rapid supraventricular tachycardias and more rapid ventricular fibrillation. Energy levels also are programmable downward in order to allow treatment of neonates and infants.

Figure 4:
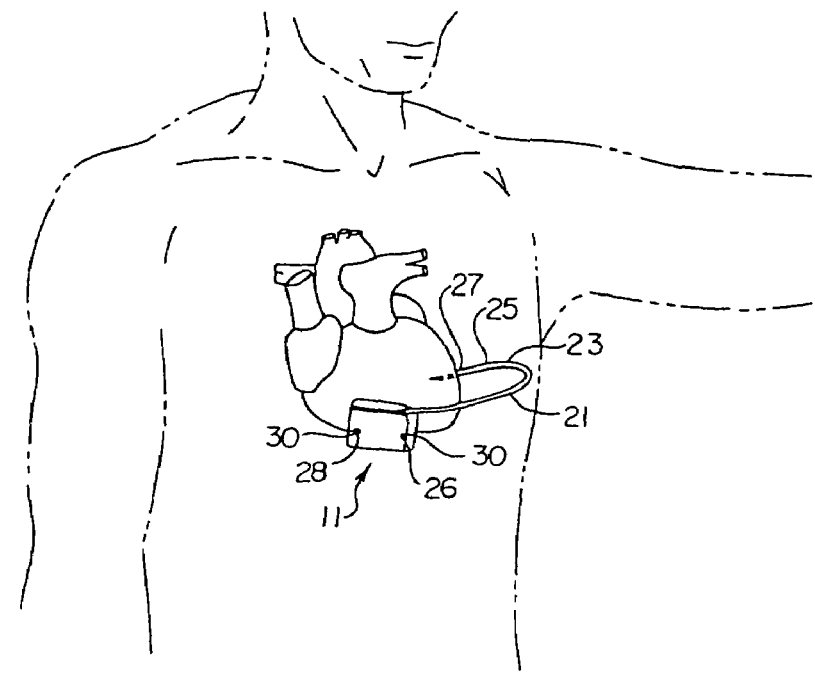
FIG. 4 is a schematic view of the S-ICD and lead of FIG. 1 subcutaneously implanted in the thorax of a patient.

Turning now to FIG. 4, the optimal subcutaneous placement of the S-ICD of the present invention is illustrated. As would be evidence to a person skilled in the art, the actual location of the S-ICD is in a subcutaneous space that is developed during the implantation process. The heart is not exposed during this process and the heart is schematically illustrated in the figures only for help in understanding where the canister and coil electrode are three dimensionally located in the left mid-clavicular line approximately at the level of the inframammary crease at approximately the 5th rib. The lead 21 of the subcutaneous electrode traverses in a subcutaneous path around the thorax terminating with its distal electrode end at the posterior axillary line ideally just lateral to the left scapula. This way the canister and subcutaneous cardioversion/defibrillation electrode provide a reasonably good pathway for current delivery to the majority of the ventricular myocardium.

Figure 5:
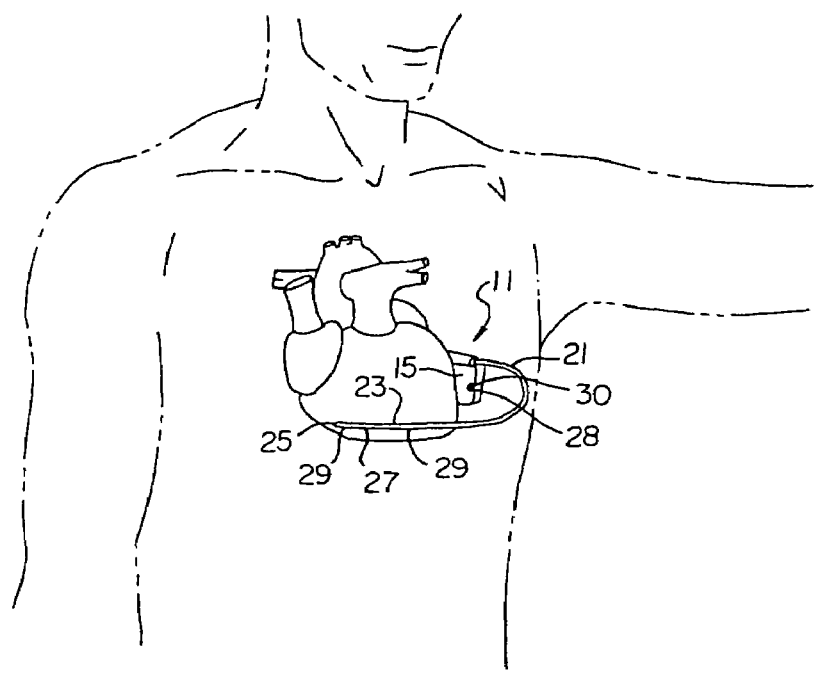
FIG. 5 is a schematic view of the S-ICD and lead of FIG. 2 subcutaneously implanted in an alternate location within the thorax of a patient.
Figure 6:
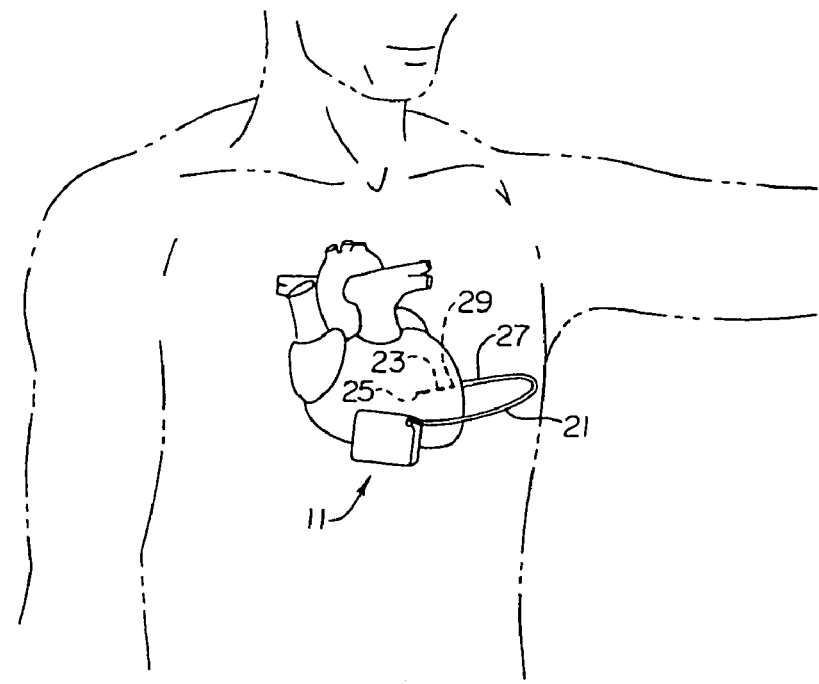
FIG. 6 is a schematic view of the S-ICD and lead of FIG. 3 subcutaneously implanted in the thorax of a patient.

FIG. 5 illustrates a different placement of the present invention. The S-ICD canister with the active housing is located in the left posterior axillary line approximately lateral to the tip of the inferior portion of the scapula. This location is especially useful in children. The lead 21 of the subcutaneous electrode traverses in a subcutaneous path around the thorax terminating with its distal electrode end at the anterior precordial region, ideally in the inframammary crease. FIG. 6 illustrates the embodiment of FIG. 1 subcutaneously implanted in the thorax with the proximal sense electrodes 23 and 25 located at approximately the left axillary line with the cardioversion/defibrillation electrode just lateral to the tip of the inferior portion of the scapula.

Figure 7:
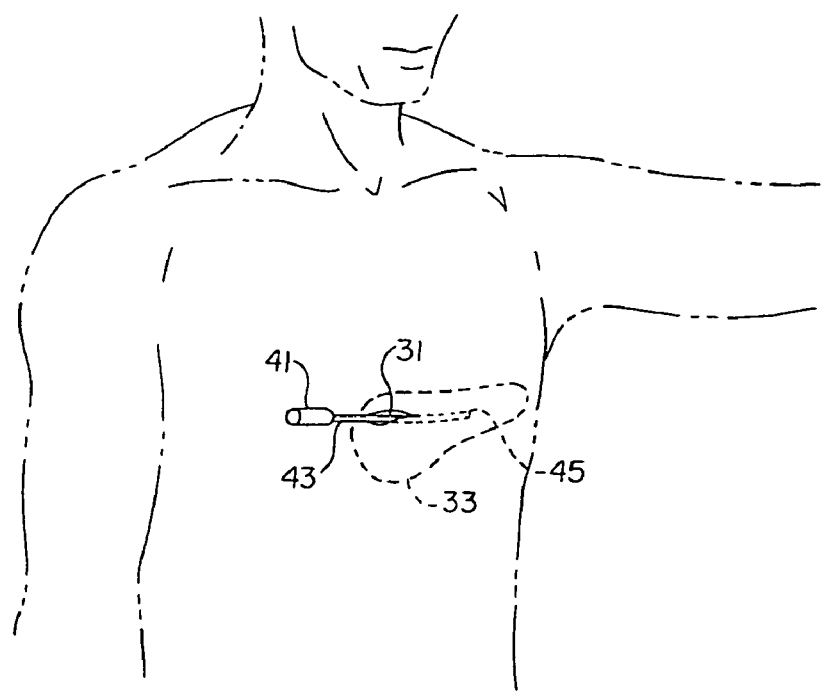
FIG. 7 is a schematic view of the method of making a subcutaneous path from the preferred incision and housing implantation point to a termination point for locating a subcutaneous electrode of the present invention.

FIG. 7 schematically illustrates the method for implanting the S-ICD of the present invention. An incision 31 is made in the left anterior axillary line approximately at the level of the cardiac apex. This incision location is distinct from that chosen for S-ICD placement and is selected specifically to allow both canister location more medially in the left inframammary crease and lead positioning more posteriorly via the introducer set (described below) around to the left posterior axillary line lateral to the left scapula. That said, the incision can be anywhere on the thorax deemed reasonably by the implanting physician although in the preferred embodiment, the S-ICD of the present invention will be applied in this region. A subcutaneous pathway 33 is then created medially to the inframammary crease for the canister and posteriorly to the left posterior axillary line lateral to the left scapula for the lead.

Figure 8:
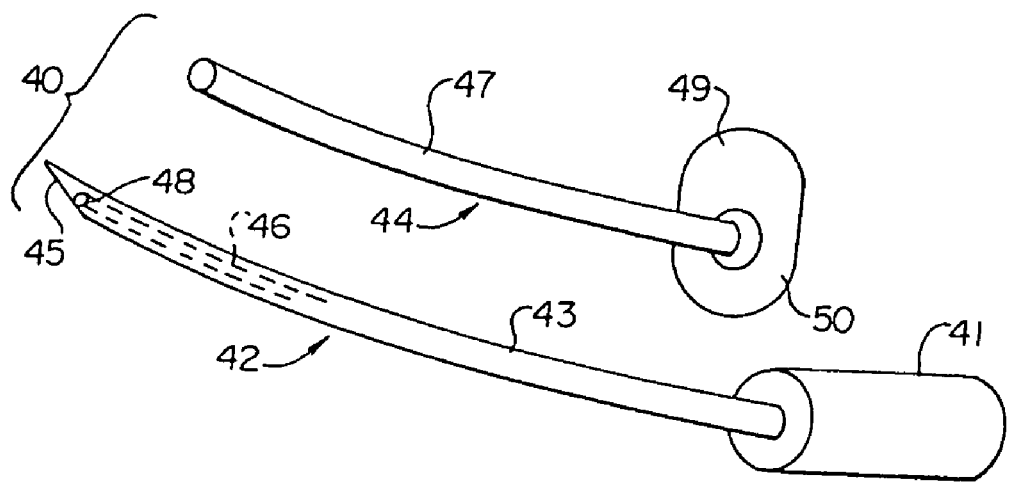
FIG. 8 is a schematic view of an introducer set for performing the method of lead insertion of any of the described embodiments.

The S-ICD canister 11 is then placed subcutaneously at the location of the incision or medially at the subcutaneous region at the left inframammary crease. The subcutaneous electrode 13 is placed with a specially designed curved introducer set 40 (see FIG. 8). The introducer set comprises a curved trocar 42 and a stiff curved peel away sheath 44. The peel away sheath is curved to allow for placement around the rib cage of the patient in the subcutaneous space created by the trocar. The sheath has to be stiff enough to allow for the placement of the electrodes without the sheath collapsing or bending. Preferably the sheath is made out of a biocompatible plastic material and is perforated along its axial length to allow for it to split apart into two sections. The trocar has a proximal handle 41 and a curved shaft 43. The distal end 45 of the trocar is tapered to allow for dissection of a subcutaneous path 33 in the patient. Preferably, the trocar is cannulated having a central Lumen 46 and terminating in an opening 48 at the distal end. Local anesthetic such as lidocaine can be delivered, if necessary, through the lumen or through a curved and elongated needle designed to anesthetize the path to be used for trocar insertion should general anesthesia not be employed. The curved peel away sheath 44 has a proximal pull tab 49 for breaking the sheath into two halves along its axial shaft 47. The sheath is placed over a guidewire inserted through the trocar after the subcutaneous path has been created. The subcutaneous pathway is then developed until it terminates subcutaneously at a location that, if a straight line were drawn from the canister location to the path termination point the line would intersect a substantial portion of the left ventricular mass of the patient. The guidewire is then removed leaving the peel away sheath. The subcutaneous lead system is then inserted through the sheath until it is in the proper location. Once the subcutaneous lead system is in the proper location, the sheath is split in half using the pull tab 49 and removed. If more than one subcutaneous electrode is being used, a new curved peel away sheath can be used for each subcutaneous electrode.

Figure 9:
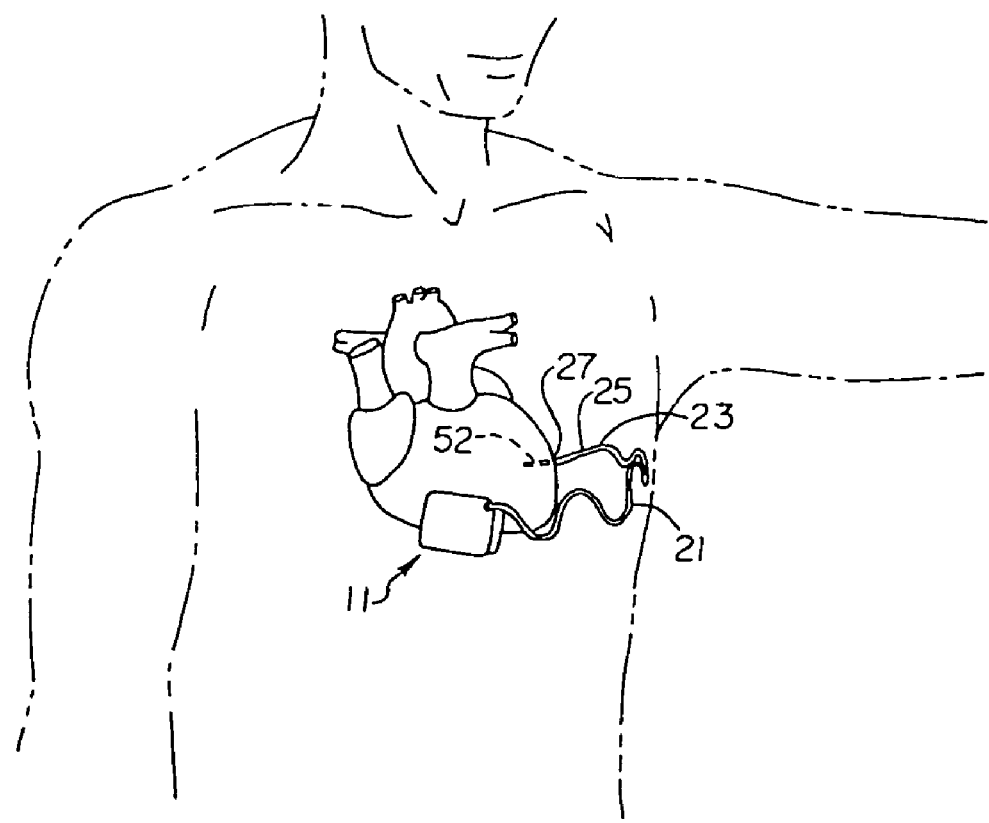
FIG. 9 is a schematic view of an alternative S-ICD of the present invention illustrating a lead subcutaneously and serpiginously implanted in the thorax of a patient for use particularly in children.

The S-ICD will have prophylactic use in adults where chronic transvenous/epicardial ICD lead systems pose excessive risk or have already resulted in difficulty, such as sepsis or lead fractures. It is also contemplated that a major use of the S-ICD system of the present invention will be for prophylactic use in children who are at risk for having fatal arrhythmias, where chronic transvenous lead systems pose significant management problems. Additionally, with the use of standard transvenous ICDs in children, problems develop during patient growth in that the lead system does not accommodate the growth. FIG. 9 illustrates the placement of the S-ICD subcutaneous lead system such that the problem that growth presents to the lead system is overcome. The distal end of the subcutaneous electrode is placed in the same location as described above providing a good location for the coil cardioversion/defibrillation electrode 27 and the sensing electrodes 23 and 25. However, insulated lead 21 is no longer placed in a taut configuration. Instead, the lead is serpiginously placed with a specially designed introducer trocar and sheath such that it has numerous waves or bends. As the child grows, the waves or bends will straighten out lengthening the lead system while maintaining proper electrode placement. Although it is expected that fibrous scarring especially around the defibrillation coil will help anchor it into position to maintain its posterior position during growth, a lead system with a distal tine or screw electrode anchoring system 52 can also be incorporated into the distal tip of the lead to facilitate lead stability (see FIG. 1). Other anchoring systems can also be used such as hooks, sutures, or the like.

Figure 10:
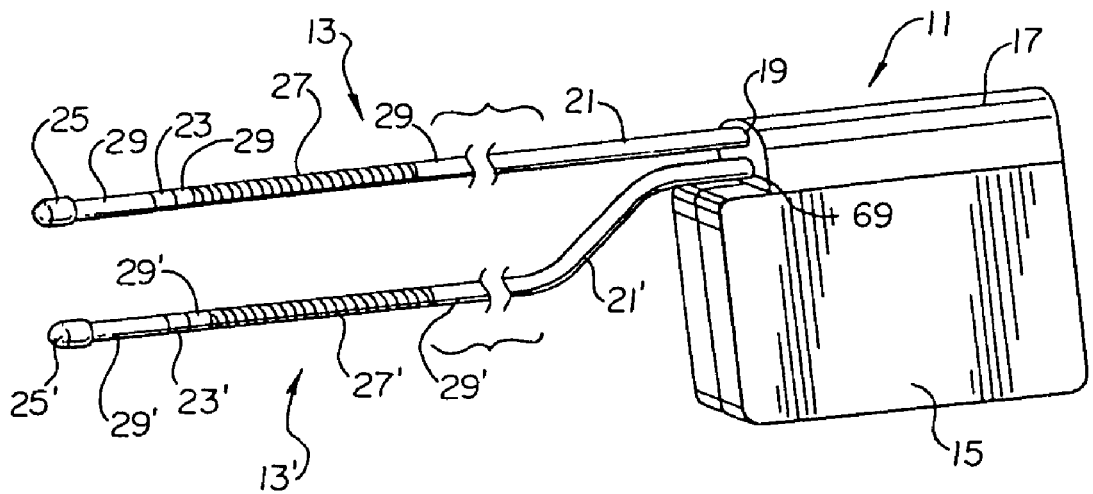
FIG. 10 is a schematic view of an alternate embodiment of an S-ICD of the present invention.
Figure 11:
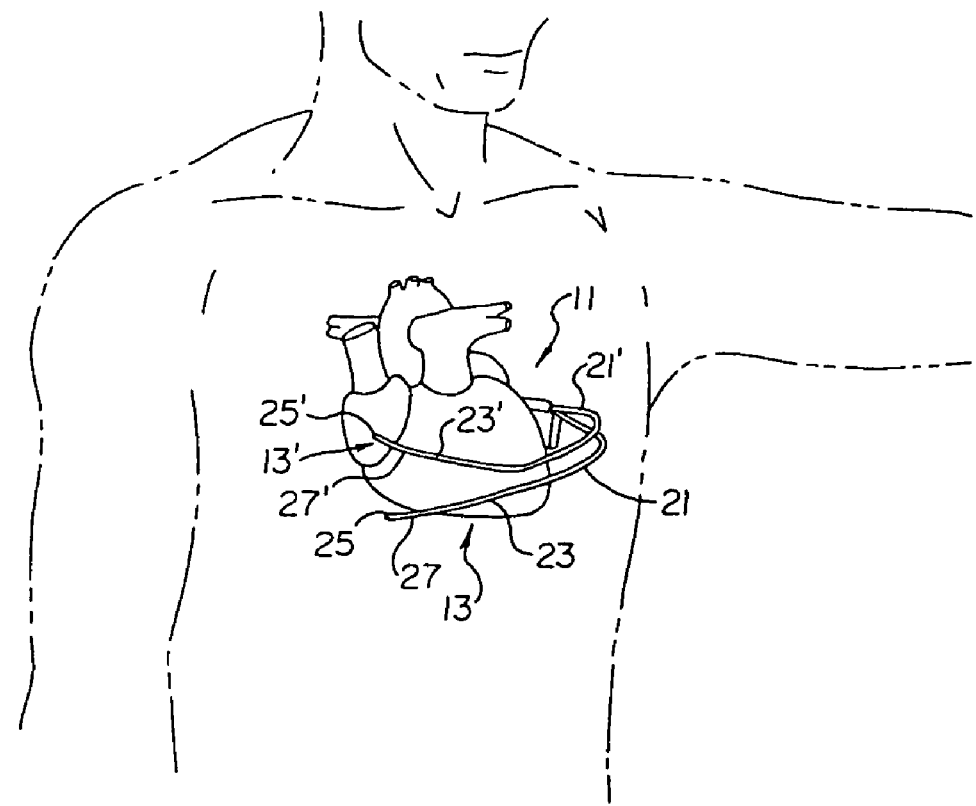
FIG. 11 is a schematic view of the S-ICD of FIG. 10 subcutaneously implanted in the thorax of a patient.

FIGS. 10 and 11 illustrate another embodiment of the present S-ICD invention. In this embodiment there are two subcutaneous electrodes 13 and 13' of opposite polarity to the canister. The additional subcutaneous electrode 13' is essentially identical to the previously described electrode. In this embodiment the cardioversion/defibrillation energy is delivered between the active surface of the canister and the two coil electrodes 27 and 27'. Additionally, provided in the canister is means for selecting the optimum sensing arrangement between the four sense electrodes 23, 23', 25, and 25'. The two electrodes are subcutaneously placed on the same side of the heart. As illustrated in FIG. 6, one subcutaneous electrode 13 is placed inferiorly and the other electrode 13' is placed superiorly. It is also contemplated with this dual subcutaneous electrode system that the canister and one subcutaneous electrode are the same polarity and the other subcutaneous electrode is the opposite polarity.

Figure 12:
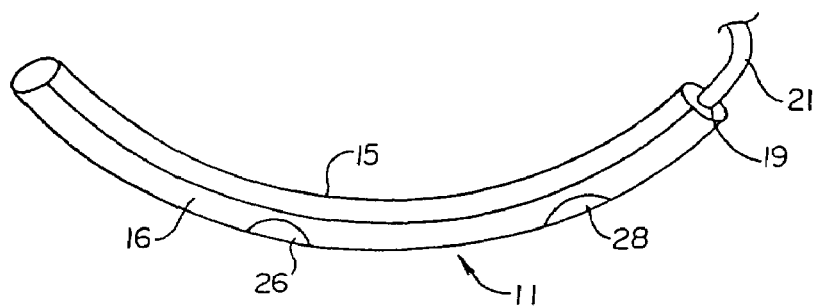
FIG. 12 is a schematic view of yet a further embodiment where the canister of the S-ICD of the present invention is shaped to be particularly useful in placing subcutaneously adjacent and parallel to a rib of a patient.
Figure 13:
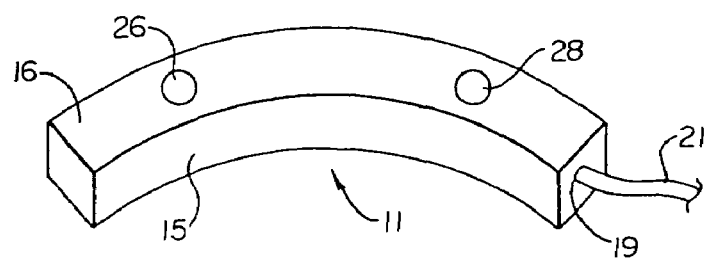
FIG. 13 is a schematic view of a different embodiment where the canister of the S-ICD of the present invention is shaped to be particularly useful in placing subcutaneously adjacent and parallel to a rib of a patient.

Turning now to FIGS. 12 and 13, further embodiments are illustrated where the canister 11 of the S-ICD of the present invention is shaped to be particularly useful in placing subcutaneously adjacent and parallel to a rib of a patient. The canister is long, thin, and curved to conform to the shape of the patient's rib. In the embodiment illustrated in FIG. 12, the canister has a diameter ranging from about 0.5 cm to about 2 cm without 1 cm being presently preferred. Alternatively, instead of having a circular cross sectional area, the canister could have a rectangular or square cross sectional area as illustrated in FIG. 13 without falling outside of the scope of the present invention. The length of the canister can vary depending on the size of the patient's thorax. In an embodiment, the canister is about 5 cm to about 40 cm long with about 10 being presently preferred. The canister is curved to conform to the curvature of the ribs of the thorax. The radius of the curvature will vary depending on the size of the patient, with smaller radiuses for smaller patients and larger radiuses for larger patients. The radius of the curvature can range from about 5 cm to about 35 cm depending on the size of the patient. Additionally, the radius of the curvature need not be uniform throughout the canister such that it can be shaped closer to the shape of the ribs. The canister has an active surface 15 that is located on the interior (concave) portion of the curvature and an inactive surface 16 that is located on the exterior (convex) portion of the curvature. The leads of these embodiments, which are not illustrated except for the attachment port 19 and the proximal end of the lead 21, can be any of the leads previously described above, with the lead illustrated in FIG. 1 being presently preferred.

The circuitry of this canister is similar to the circuitry described above. Additionally, the canister can optionally have at least one sense electrode located on either the active surface of the inactive surface and the circuitry within the canister can be programmable as described above to allow for the selection of the best sense electrodes. It is presently preferred that the canister have two sense electrodes 26 and 28 located on the inactive surface of the canisters as illustrated, where the electrodes are spaced from about 1 to about 10 cm apart with a spacing of about 3 cm being presently preferred. However, the sense electrodes can be located on the active surface as described above.

It is envisioned that the embodiment of FIG. 12 will be subcutaneously implanted adjacent and parallel to the left anterior 5th rib, either between the 4th and 5th ribs or between the 5th and 6th ribs. However other locations can be used.

Another component of the S-ICD of the present invention is a cutaneous test electrode system designed to simulate the subcutaneous high voltage shock electrode system as well as the QRS cardiac rhythm detection system. This test electrode system is comprised of a cutaneous patch electrode of similar surface area and impedance to that of the S-ICD canister itself together with a cutaneous strip electrode comprising a defibrillation strip as well as two button electrodes for sensing of the QRS. Several cutaneous strip electrodes are available to allow for testing various bipole spacings to optimize signal detection comparable to the implantable system.

FIGS. 14, 15, 16, 17 and 18 depict particular US-ICD embodiments of the present invention. The various sensing, shocking and pacing circuitry described in detail above with respect to the S-ICD embodiments may additionally be incorporated into the following US-ICD embodiments. Furthermore, particular aspects of any individual S-ICD embodiment discussed above may be incorporated, in whole or in part, into the US-ICD embodiments depicted in the following figures.

Figure 14:
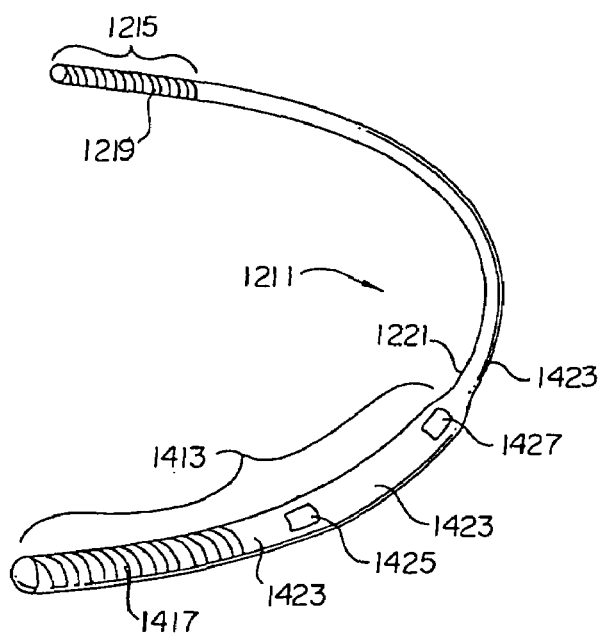
FIG. 14 is a schematic view of a Unitary Subcutaneous ICD (US-ICD) of the present invention.

Turning now to FIG. 14, the US-ICD of the present invention is illustrated. The US-ICD consists of a curved housing 1211 with a first and second end. The first end 1413 is thicker than the second end 1215. This thicker area houses a battery supply, capacitor and operational circuitry for the US-ICD. The circuitry will be able to monitor cardiac rhythms for tachycardia and fibrillation, and if detected, will initiate charging the capacitor and then delivering cardioversion/defibrillation energy through the two cardioversion/defibrillating electrodes 1417 and 1219 located on the outer surface of the two ends of the housing. The circuitry can provide cardioversion/defibrillation energy in different types of waveforms. In one embodiment, a 100 uF biphasic waveform is used of approximately 10-20 ms total duration and with the initial phase containing approximately ⅔ of the energy, however, any type of waveform can be utilized such as monophasic, biphasic, multiphasic or alternative waveforms as is known in the art.

The housing of the present invention can be made out of titanium alloy or other presently preferred ICD designs. It is contemplated that the housing is also made out of biocompatible plastic materials that electronically insulate the electrodes from each other. However, it is contemplated that a malleable canister that can conform to the curvature of the patient's chest will be preferred. In this way the patient can have a comfortable canister that conforms to the unique shape of the patient's rib cage. Examples of conforming ICD housings are provided in U.S. Pat. No. 5,645,586, the entire disclosure of which is herein incorporated by reference. In the preferred embodiment, the housing is curved in the shape of a $5^{th}$ rib of a person. Because there are many different sizes of people, the housing will come in different incremental sizes to allow a good match between the size of the rib cage and the size of the US-ICD. The length of the US-ICD will range from about 15 to about 50 cm. Because of the primary preventative role of the therapy and the need to reach energies over 40 Joules, a feature of the preferred embodiment is that the charge time for the therapy intentionally be relatively long to allow capacitor charging within the limitations of device size.

The thick end of the housing is currently needed to allow for the placement of the battery supply, operational circuitry, and capacitors. It is contemplated that the thick end will be about 0.5 cm to about 2 cm wide with about 1 cm being presently preferred. As microtechnology advances, the thickness of the housing will become smaller.

The two cardioversion/defibrillation electrodes on the housing are used for delivering the high voltage cardioversion/defibrillation energy across the heart. In the preferred embodiment, the cardioversion/defibrillation electrodes are coil electrodes, however, other cardioversion/defibrillation electrodes could be used such as having electrically isolated active surfaces or platinum alloy electrodes. The coil cardioversion/defibrillation electrodes are about 5-10 cm in length. Located on the housing between the two cardioversion/defibrillation electrodes are two sense electrodes 1425 and 1427. The sense electrodes are spaced far enough apart to be able to have good QRS detection. This spacing can range from 1 to 10 cm with 4 cm being presently preferred. The electrodes may or may not be circumferential with the preferred embodiment. Having the electrodes non-circumferential and positioned outward, toward the skin surface, is a means to minimize muscle artifact and enhance QRS signal quality. The sensing electrodes are electrically isolated from the cardioversion/defibrillation electrode via insulating areas 1423. Analogous types of cardioversion/defibrillation electrodes are currently commercially available in a transvenous configuration. For example, U.S. Pat. No. 5,534,022, the entire disclosure of which is herein incorporated by reference, discloses a composite electrode with a coil cardioversion/defibrillation electrode and sense electrodes. Modifications to this arrangement are contemplated within the scope of the invention. One such modification is to have the sense electrodes at the two ends of the housing and have the cardioversion/defibrillation electrodes located in between the sense electrodes. Another modification is to have three or more sense electrodes spaced throughout the housing and allow for the selection of the two best sensing electrodes. If three or more sensing electrodes are used, then the ability to change which electrodes are used for sensing would be a programmable feature of the US-ICD to adapt to changes in the patient physiology and size over time. The programming could be done via the use of physical switches on the canister, or as presently preferred, via the use of a programming wand or via a wireless connection to program the circuitry within the canister.

Figure 15:
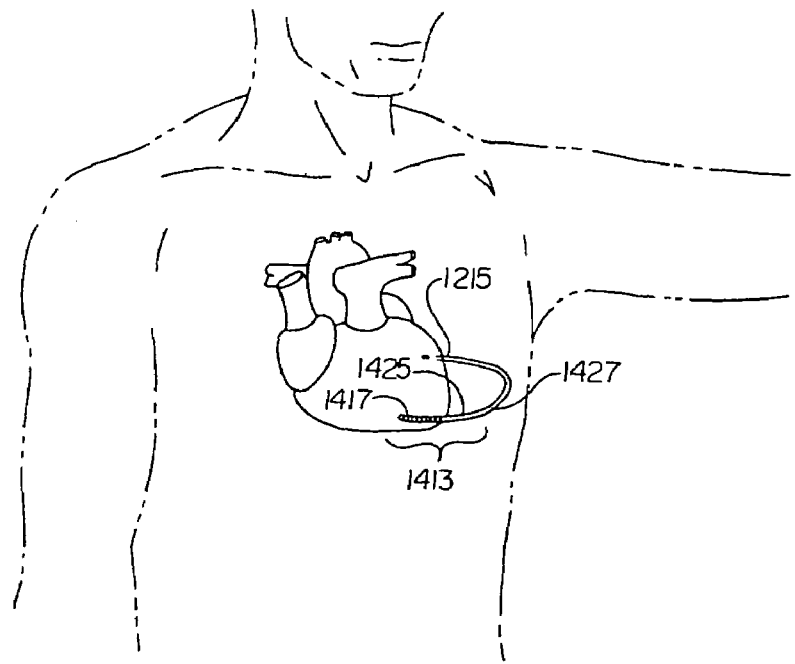
FIG. 15 is a schematic view of the US-ICD subcutaneously implanted in the thorax of a patient.

Turning now to FIG. 15, the optimal subcutaneous placement of the US-ICD of the present invention is illustrated. As would be evident to a person skilled in the art, the actual location of the US-ICD is in a subcutaneous space that is developed during the implantation process. The heart is not exposed during this process and the heart is schematically illustrated in the figures only for help in understanding where the device and its various electrodes are three dimensionally located in the thorax of the patient. The US-ICD is located between the left mid-clavicular line approximately at the level of the inframammary crease at approximately the $5^{th}$ rib and the posterior axillary line, ideally just lateral to the left scapula. This way the US-ICD provides a reasonably good pathway for current delivery to the majority of the ventricular myocardium.

Figure 16:
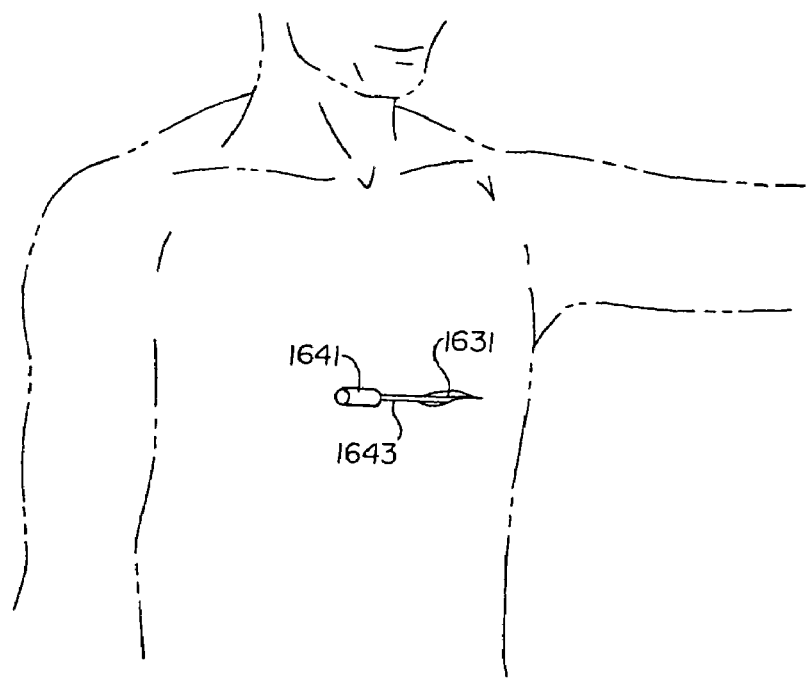
FIG. 16 is a schematic view of the method of making a subcutaneous path from the preferred incision for implanting the US-ICD.
Figure 17:
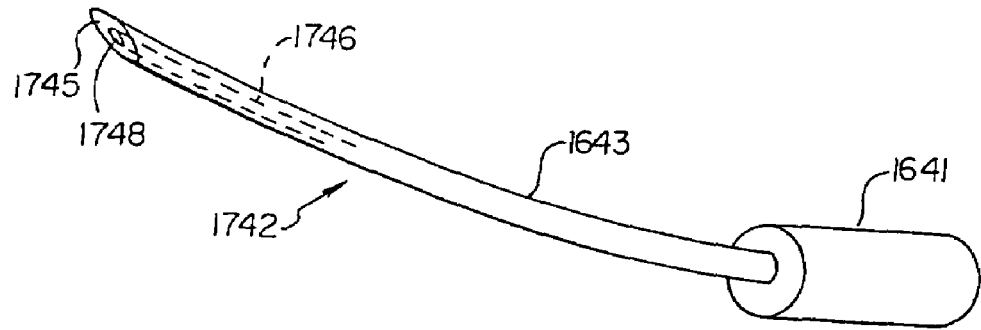
FIG. 17 is a schematic view of an introducer for performing the method of US-ICD implantation.

FIG. 16 schematically illustrates the method for implanting the US-ICD of the present invention. An incision 1631 is made in the left anterior axillary line approximately at the level of the cardiac apex. A subcutaneous pathway is then created that extends posteriorly to allow placement of the US-ICD. The incision can be anywhere on the thorax deemed reasonable by the implanting physician although in the preferred embodiment, the US-ICD of the present invention will be applied in this region. The subcutaneous pathway is created medially to the inframammary crease and extends posteriorly to the left posterior axillary line. The pathway is developed with a specially designed curved introducer 1742 (see FIG. 17). The trocar has a proximal handle 1641 and a curved shaft 1643. The distal end 1745 of the trocar is tapered to allow for dissection of a subcutaneous path in the patient. Preferably, the trocar is cannulated having a central lumen 1746 and terminating in an opening 1748 at the distal end. Local anesthetic such as lidocaine can be delivered, if necessary, through the lumen or through a curved and elongated needle designed to anesthetize the path to be used for trocar insertion should general anesthesia not be employed. Once the subcutaneous pathway is developed, the US-ICD is implanted in the subcutaneous space, the skin incision is closed using standard techniques.

Figure 18:
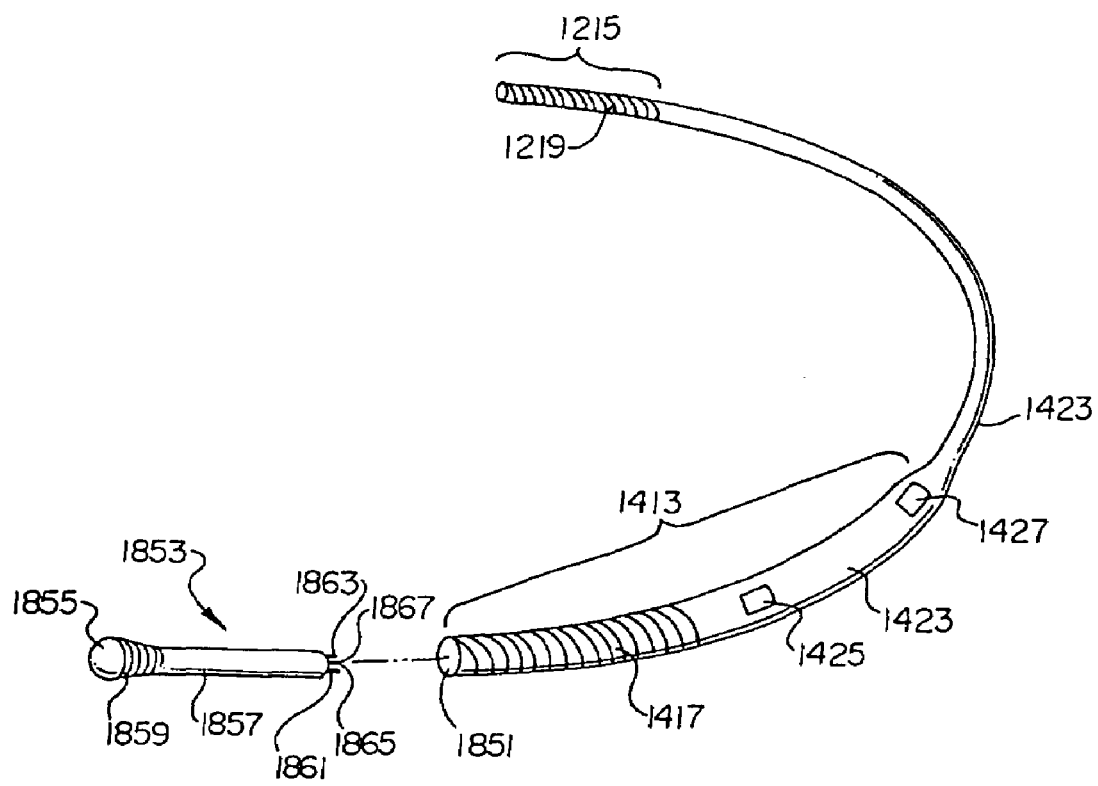
FIG. 18 is an exploded schematic view of an alternate embodiment of the present invention with a plug-in portion that contains operational circuitry and means for generating cardioversion/defibrillation shock waves.

As described previously, the US-ICDs of the present invention vary in length and curvature. The US-ICDs are provided in incremental sizes for subcutaneous implantation in different sized patients. Turning now to FIG. 18, a different embodiment is schematically illustrated in exploded view which provides different sized US-ICDs that are easier to manufacture. The different sized US-ICDs will all have the same sized and shaped thick end 1413. The thick end is hollow inside allowing for the insertion of a core operational member 1853. The core member comprises a housing 1857 which contains the battery supply, capacitor and operational circuitry for the US-ICD. The proximal end of the core member has a plurality of electronic plug connectors. Plug connectors 1861 and 1863 are electronically connected to the sense electrodes via pressure fit connectors (not illustrated) inside the thick end which are standard in the art. Plug connectors 1865 and 1867 are also electronically connected to the cardioverter/defibrillator electrodes via pressure fit connectors inside the thick end. The distal end of the core member comprises an end cap 1855, and a ribbed fitting 1859 which creates a water-tight seal when the core member is inserted into opening 1851 of the thick end of the US-ICD.

The S-ICD and US-ICD, in alternative embodiments, have the ability to detect and treat atrial rhythm disorders, including atrial fibrillation. The S-ICD and US-ICD have two or more electrodes that provide a far-field view of cardiac electrical activity that includes the ability to record the P-wave of the electrocardiogram as well as the QRS. One can detect the onset and offset of atrial fibrillation by referencing to the P-wave recorded during normal sinus rhythm and monitoring for its change in rate, morphology, amplitude and frequency content. For example, a well-defined P-wave that abruptly disappeared and was replaced by a low-amplitude, variable morphology signal would be a strong indication of the absence of sinus rhythm and the onset of atrial fibrillation. In an alternative embodiment of a detection algorithm, the ventricular detection rate could be monitored for stability of the R-R coupling interval. In the examination of the R-R interval sequence, atrial fibrillation can be recognized by providing a near constant irregularly irregular coupling interval on a beat-by-beat basis. An R-R interval plot during AF appears "cloud-like" in appearance when several hundred or thousands of R-R intervals are plotted over time when compared to sinus rhythm or other supraventricular arrhythmias. Moreover, a distinguishing feature compared to other rhythms that are irregularly irregular, is that the QRS morphology is similar on a beat-by-beat basis despite the irregularity in the R-R coupling interval. This is a distinguishing feature of atrial fibrillation compared to ventricular fibrillation where the QRS morphology varies on a beat-by-beat basis. In yet another embodiment, atrial fibrillation may be detected by seeking to compare the timing and amplitude relationship of the detected P-wave of the electrocardiogram to the detected QRS (R-wave) of the electrocardiogram. Normal sinus rhythm has a fixed relationship that can be placed into a template matching algorithm that can be used as a reference point should the relationship change.

In other aspects of the atrial fibrillation detection process, one may include alternative electrodes that may be brought to bear in the S-ICD or US-ICD systems either by placing them in the detection algorithm circuitry through a programming maneuver or by manually adding such additional electrode systems to the S-ICD or US-ICD at the time of implant or at the time of follow-up evaluation. One may also use electrodes for the detection of atrial fibrillation that may or may not also be used for the detection of ventricular arrhythmias given the different anatomic locations of the atria and ventricles with respect to the S-ICD or US-ICD housing and surgical implant sites.

Once atrial fibrillation is detected, the arrhythmia can be treated by delivery of a synchronized shock using energy levels up to the maximum output of the device therapy for terminating atrial fibrillation or for other supraventricular arrhythmias. The S-ICD or US-ICD electrode system can be used to treat both atrial and ventricular arrhythmias not only with shock therapy but also with pacing therapy. In a further embodiment of the treatment of atrial fibrillation or other atrial arrhythmias, one may be able to use different electrode systems than what is used to treat ventricular arrhythmias. Another embodiment would allow for different types of therapies (amplitude, waveform, capacitance, etc.) for atrial arrhythmias compared to ventricular arrhythmias.

The core member of the different sized and shaped US-ICD will all be the same size and shape. That way, during an implantation procedure, multiple sized US-ICDs can be available for implantation, each one without a core member. Once the implantation procedure is being performed, then the correct sized US-ICD can be selected and the core member can be inserted into the US-ICD and then programmed as described above. Another advantage of this configuration is when the battery within the core member needs replacing it can be done without removing the entire US-ICD.

FIG. 19(*a*) illustrates an embodiment of the subcutaneous lead electrode or "lead electrode assembly" 100. The lead electrode assembly 100 is designed to provide an electrode 107 to be implanted subcutaneously in the posterior thorax of a patient for delivery of cardioversion/defibrillation energy. The lead electrode assembly 100 is further designed to provide a path for the cardioversion/defibrillation energy to reach the electrode 107 from the operational circuitry within the canister 11 of an S-ICD such as the embodiment shown in FIG. 1.

The lead electrode assembly 100 comprises a connector 111, a lead 21, a lead fastener 146, an electrode 107 and an appendage 118. The connector 111 is connected to the lead 21. The lead 21 is further connected to the electrode 107 with the lead fastener 146. The appendage 118 is mounted to the electrode 107.

The connector 111 provides an electrical connection between the lead 21 and the operational circuitry within the canister 11 of an S-ICD such as the embodiment shown in FIG. 1. Connector 111 is designed to mate with the connection port 19 on the canister 11. In the embodiment under discussion, the connector 111 meets the IS-I standard.

The lead 21 of the lead electrode assembly 100 provides an electrical connection between the connector 111 and the electrode 107. The lead 21 comprises a distal end 101 and a proximal end 102. The distal end 101 of the lead 21 is attached to the connector 111. The proximal end 102 of the lead 21 is attached to electrode 107 with the lead fastener 146.

The lead 21 has a lead length, $l_{Lead}$, measured from the connector 111 along the lead 21 to the lead fastener 146 of the electrode 107. The length of the lead 21 is approximately 25 cm. In alternative embodiments, the lead lengths range between approximately 5 cm and approximately 55 cm.

The lead fastener 146 provides a robust physical and electrical connection between the lead 21 and the electrode 107. The lead fastener 146 joins the proximal end 102 of the lead 21 to electrode 107.

The electrode 107 comprises an electrically conductive member designed to make contact with the tissue of the patient and transfer cardioversion/defibrillation energy to the tissue of the patient from the S-ICD canister 11.

The electrode 107 illustrated is generally flat and planar, comprising a top surface 110, a bottom surface 115, a distal end 103 and a proximal end 104. The lead fastener 146 is attached to the top surface 110 of the distal end 103 of the electrode 107.

The electrode 107 may have shapes other than planar. In an alternate embodiment, the electrode 107 is shaped like a coil.

The appendage 118 is a member attached to the electrode 107 that can be gripped and used to precisely locate the lead electrode assembly 100 during its surgical implantation within the patient.

The appendage 118 has a first end 105, a second end 106, a distal edge 121 and a proximal edge 129. The second end 106 of the appendage 118 is attached to the top surface 110 of the electrode 107. The appendage 118 is positioned such that its proximal edge 129 is within approximately 20 mm of the proximal end 104 of the electrode 107. In alternate embodiments, the appendage 118 is attached to the electrode 107 in other positions.

It is useful at this point, to set out several general definitions for future reference in discussing the dimensions and placement of appendages 118.

The appendage height, $h_{Appendage}$, is defined as the distance from the point of the appendage 118 most distant from the electrode 107 to a point of the appendage 118 closest to the electrode 107 measured along a line perpendicular to the top surface 110 of the electrode 107. The appendage height of the appendage 118 illustrated, for example, would be measured between the first end 105 of the appendage 118 and the second end 106 of the appendage 118.

The appendage height of the appendage 118 illustrated is approximately 5 mm. In alternative embodiments, the appendage heights range between approximately 1 mm and approximately 10 mm.

The appendage interface is defined as the part of the appendage 118 that joins it to the electrode 107. The appendage interface of the appendage 118 illustrated, for example, would be the second end 106 of the appendage 118.

The appendage length, $l_{Appendage}$, is the length of the appendage 118 along the appendage interface. The appendage interface of the appendage 118 illustrated, for example, would be the length of the second end 106 of the appendage 118.

Figure 19A:
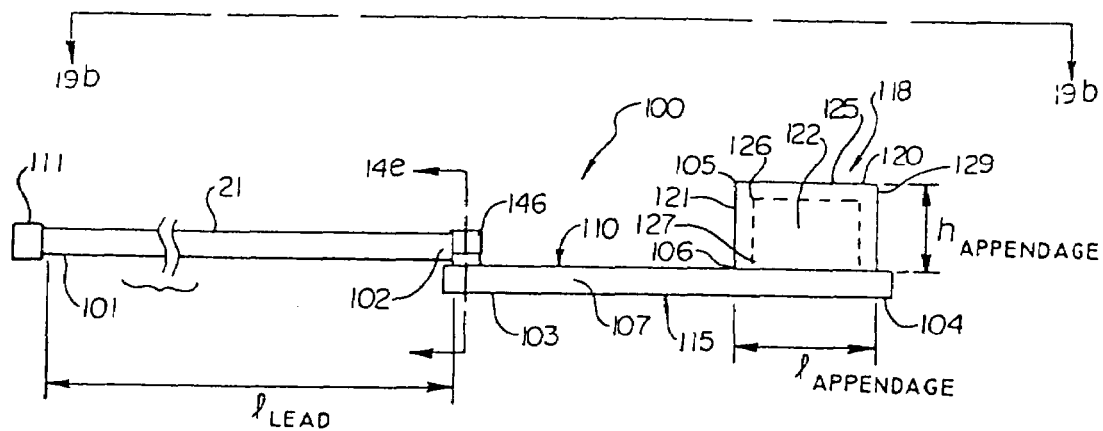
FIG. 19(a) is a side plan view of an embodiment of a lead electrode assembly with a top-mounted fin.

The appendage length of the appendage 118 illustrated in FIG. 19(a) is approximately 1 cm. In alternative embodiments, appendage lengths range between approximately 2 mm and approximately 6 cm. In an alternate embodiment, the appendage 118 is substantially as long as the electrode 107.

More particularly, the appendage 118 of the embodiment illustrated is a fin 120 comprising a fin core 122 (phantom view) and a coating 125.

The fin core 122 generally provides support for the fin 120. The fin core 122 has a first end 126 and a second end 127. The second end 127 of the fin core 122 is attached to the top surface 110 of the electrode 107.

The fin core 122 comprises a metal selected from the group consisting essentially of titanium, nickel alloys, stainless steel alloys, platinum, platinum iridium, and mixtures thereof. In other embodiments, the fin core 122 comprises any rugged material that can be attached to the first surface 110 of the electrode 107.

The coating 125 is disposed around the fin core 122. The coating 125 provides a surface for the fin 120 that can be easily gripped during the implantation of the lead electrode assembly 100. The coating 125 covering the fin core 122 is composed of molded silicone. In an alternative embodiment, the coating 125 may be any polymeric material. In this specification, the term polymeric material includes the group of materials consisting of a polyurethane, a polyamide, a polyetheretherketone (PEEK), a polyether block amide (PEBA), a polytetrafluoroethylene (PTFE), a silicone and mixtures thereof.

In one embodiment, the fin 120 is reinforced with a layer of Dacron® polymer mesh attached to the inside of the coating 125. Dacron® is a registered trademark of E. I. du Pont de Nemours and Company Corporation, Wilmington, Del. In another embodiment, the Dacron® polymer mesh attached to the outside of the coating 125. In another embodiment, the fin 120 is reinforced with a layer of any polymeric material.

Figure 19B:
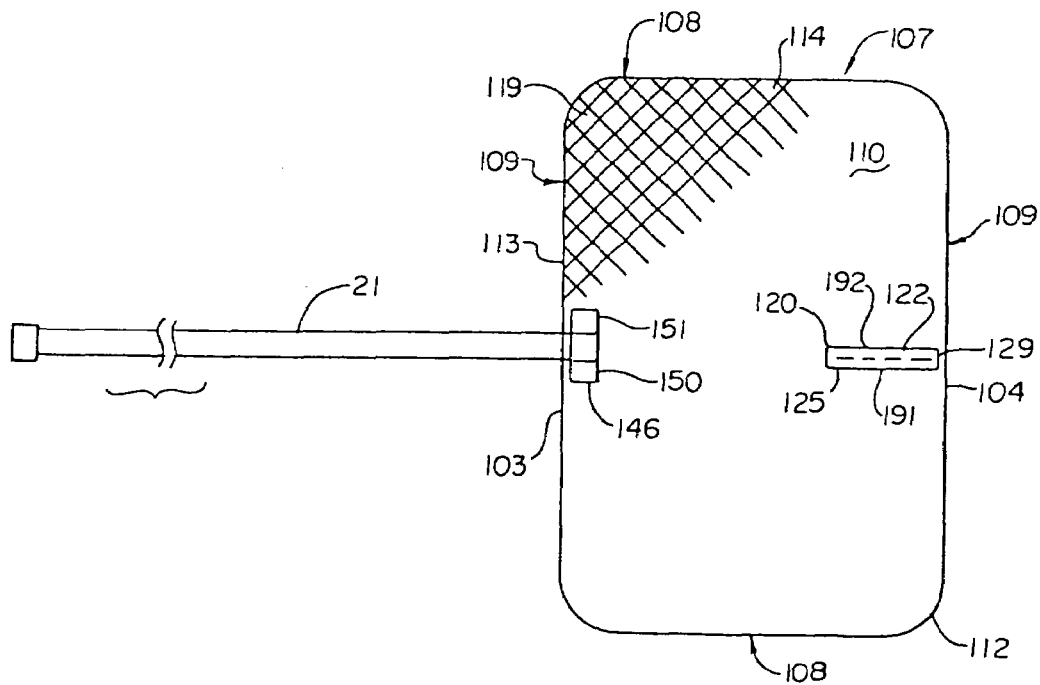
FIG. 19(b) is a top plan view of an embodiment of a lead electrode assembly with a top-mounted fin.

FIG. 19(b) illustrates a top view of the lead electrode assembly 100. The electrode 107 is substantially rectangular in shape, comprising a first pair of sides 108, a second pair of sides 109 and four corners 112. In an alternative embodiment the electrode 107 has a shape other than rectangular. In this embodiment, the corners 112 of the electrode 107 are rounded. In an alternative embodiment the corners 112 of the electrode 107 are not rounded.

The first pair of sides 108 of the electrode 107 is substantially linear, substantially parallel to each other and is approximately 1 cm in length. The second pair of sides 109 of the electrode 107 is also substantially linear, substantially parallel with each other and is approximately 5 cm in length. The bottom surface 115 of the electrode 107 has an area of approximately 500 square mm. In alternative embodiments, the first pair of sides 108 and the second pair of sides 109 of the electrode 107 are neither linear nor parallel.

In alternative embodiments, the length of the first pair of sides 108 and second pair of sides 109 of the electrode 107 range independently between approximately 1 cm and approximately 5 cm. The surface area of the bottom surface 115 of the electrode 107 ranges between approximately 100 sq. mm and approximately 2500 sq. mm. In one embodiment, the first pair of sides 108 and second pair of sides 109 of the electrode 107 are linear and have equal length, such that the electrode 107 is substantially square-shaped.

The electrode 107 comprises a sheet of metallic mesh 114 further comprised of woven wires 119. The metallic mesh 114 comprises a metal selected from the group consisting essentially of titanium, nickel alloys, stainless steel alloys, platinum, platinum iridium, and mixtures thereof. In other embodiments, the metallic mesh 114 comprises any conductive material.

In an alternate embodiment, the electrode 107 comprises a solid metallic plate. The metallic plate comprises a metal selected from the group consisting essentially of titanium, nickel alloys, stainless steel alloys, platinum, platinum iridium, and mixtures thereof. In other embodiments, the solid plate comprises any conductive material.

The metallic mesh 114 is approximately a 150 mesh, having approximately 150 individual wires 119 per inch. In alternative embodiments, the metallic mesh 114 ranges between approximately a 50 mesh and approximately a 200 mesh. In this embodiment, the diameter of the wires 119 of the mesh is approximately 1 mil. In alternative embodiments, the diameter of the wires 119 ranges between approximately 1 and approximately 5 mils.

The metallic mesh 114 is first prepared by spot welding together the wires 119 located along the first pair of sides 108 and second pair of sides 109 of the metallic mesh 114. The excess lengths of wires are then ground or machined flush, so as to produce a smooth edge and to form a smooth border 113. In an alternate embodiment, the wires 119 located along the first pair of sides 108 and second pair of sides 109 of the metallic mesh 114 are bent in toward the metallic mesh 114 to form a smooth border 113.

The fin 120 is attached to the top surface 110 of the electrode 107 in a position centered between the first pair of sides 108 of the electrode 107. In other embodiments, the fin 120 is not centered between the first pair of sides 108 of the electrode 107.

The fin 120 is a planar shape comprising a first face 191 and a second face 192. The first face 191 and the second face 192 of the fin 120 are substantially parallel to the first pair of sides 108 of the electrode 107. In other embodiments, the first face 191 and the second face 192 of the fin 120 are positioned in orientations other than parallel to the first pair of sides 108 of the electrode 107.

The first face 191 and the second face 192 of the fin 120 extend from and substantially perpendicular to the top surface 110 of the electrode 107. In an alternative embodiment, the first face 191 and the second face 192 of the fin 120 extend from the top surface 110 of the electrode 107 at other than right angles.

The fin core 122 of the fin 120 is spot welded to the metallic mesh 114 comprising the electrode 107. In another embodiment, the fin 120 may be composed entirely of a polymeric material and attached to the electrode 107 by means known in the art.

Figure 19C:
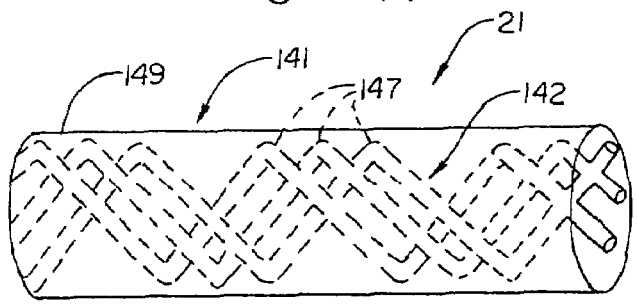
FIG. 19(c) is a side plan view of a section of the lead in an embodiment of the lead electrode assembly.

FIG. 19(c) illustrates in detail a section of the lead 21 of this embodiment. The lead 21 comprises an electrically insulating sheath 141 and an electrical conductor 142.

The electrically insulating sheath 141 is disposed around the electrical conductor 142 (phantom view). The electrically insulating sheath 141 prevents the cardioversion/defibrillation energy passing through the electrical conductor 142 to the electrode from passing into objects surrounding the lead 21. The electrically insulating sheath 141, comprises a tube 149 disposed around the electrical conductor 142. The tube is composed of either silicone, polyurethane or composite materials. One skilled in the art will recognize that the tube 149 could alternately be composed of any insulating, flexible, bio-compatible material suitable to this purpose.

In this embodiment, the electrical conductor 142 comprises three highly-flexible, highly-conductive coiled fibers known as filars 147 (phantom view). These fibers are wound in a helical shape through the electrically insulating sheath 141. In an alternate embodiment, the filars lie as linear cables within the electrically insulating sheath 141. In another alternate embodiment, a combination of helically coiled and linear filars lies within the electrically insulating sheath 141.

Figure 19D:
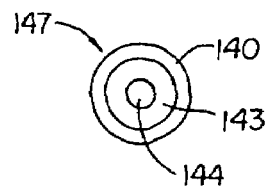
FIG. 19(d) is a cross-sectional view of a filar in the lead in an embodiment of the lead electrode assembly.

FIG. 19(d) illustrates a cross-section of a filar 147. The filars 147 of the embodiment illustrated comprise a metal core 144, a metal tube 143 and an insulating coating 140. The metal tube 143 is disposed around the metal core 144. The insulating coating 140 is disposed around the metal tube. The metal core 144 is made of silver and the metal tube 143 is made of MP35N® stainless steel, a product of SPS Technologies of Jenkintown, Pa. The insulating coating 140 is made of Teflon. The filars 147 of this structure are available as DFT™ (drawn filled tube) conductor coil, available from Fort Wayne Metals Research Products Corp. of Fort Wayne, Ind.

In an alternative embodiment, the filars 147 further comprise an intermediate coating (not shown) disposed between the metal tube 143 and the insulating coating 140. This intermediate coating is made of platinum, iridium ruthenium, palladium or an alloy of these metals.

In another alternative embodiment, the filars 147 comprise DBS™ (drawn braised strands) also available from Fort Wayne Metals Research Products Corp. of Fort Wayne, Ind.

Figure 19E:
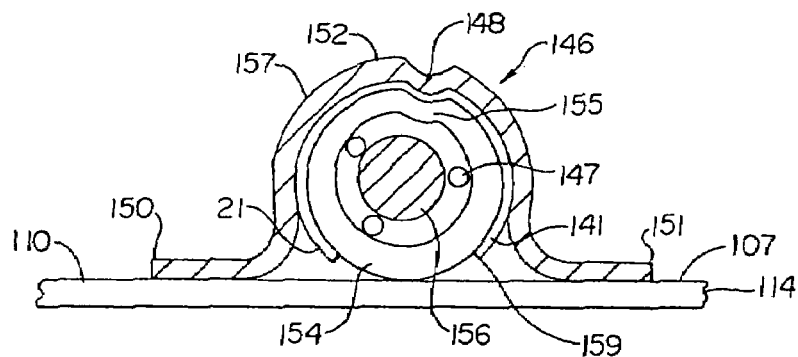
FIG. 19(e) is a cross-sectional view of the lead fastener of an embodiment of a lead electrode assembly.

Turning now to FIG. 19(e), a cross section of the lead fastener 146 is shown in detail. The lead fastener 146 provides a robust physical and electrical connection between the lead 21 and the electrode 107.

In this embodiment, the lead fastener 146 comprises a metal strip 157, a crimping tube 154 and a crimping pin 156. The metal strip 157 has a first end 150, a second end 151, and a middle portion 152. The first end 150 and second end 151 of the metal strip 157 are separated by the middle portion 152. The first end 150 and second end 151 of the metal strip 157 are attached to the electrode 107. In this embodiment, the first end 150 and second end 151 of the lead fastener 146 are spot welded to the top surface 110 of the metallic mesh 114 comprising the electrode 107. In other embodiments, other fastening methods known in the art can be used.

The middle portion 152 of the metal strip 157 is raised away from the electrode 107 to permit the crimping tube 154 and electrically insulating sheath 141 of the lead 21 to fit between the metal strip 157 and the electrode 107.

The middle portion 152 of the metal strip 157 contains a crimp point 148. The crimp point 148 squeezes the crimping tube 154 and electrically insulating sheath 141 of the lead 21 thereby gripping it, and thereby providing a robust structural connection between the lead 21 and the electrode 107.

The filars 147 of the lead 21 are situated between the crimping tube 154 and crimping pin 156. The crimping tube 154 has a crimping point 155 which causes the filars 147 to be squeezed between crimping tube 154 and crimping pin 156. A gap 159 in the electrically insulating sheath 141 allows the crimping tube 155 to make contact the electrode 107, thereby forming a robust electrical connection.

The metal strip 157, the crimping tube 154 and crimping pin 156 are each made of platinum iridium. In an alternative embodiment, the metal strip 157, crimping tube 154 and crimping pin 156 are each made of a metal selected from the group consisting essentially of titanium, nickel alloys, stainless steel alloys, platinum, platinum iridium, and mixtures thereof. In an alternative embodiment, the metal strip 157, crimping tube 154 and crimping pin 156 are each made of any conductive material.

Figure 19F:
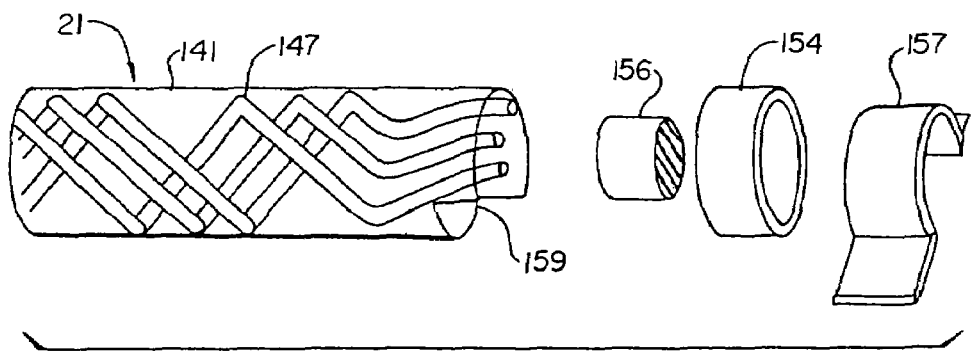
FIG. 19(f) is an exploded view of the lead fastener of an embodiment of a lead electrode assembly.

FIG. 19(f) illustrates an exploded view of the lead fastener 146. In other embodiments, other types of lead fasteners 146 known in the art are used.

Figure 20A:
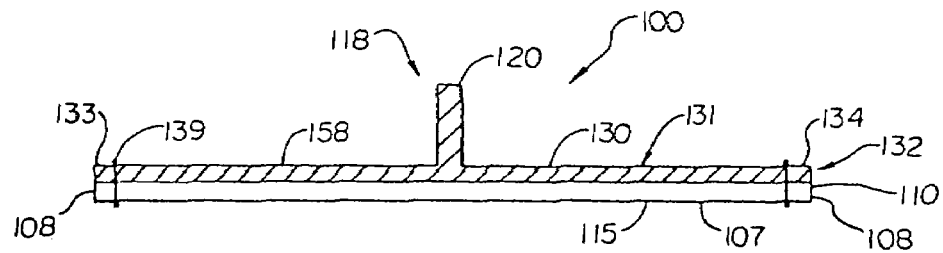
FIG. 20(a) is a cross-sectional front plan view of an embodiment of a lead electrode assembly with a top-mounted fin.

FIG. 20(a) illustrates an alternative embodiment of the lead electrode assembly 100. This embodiment is substantially similar to the lead electrode assembly 100 illustrated in FIGS. 19(a)-19(f). In this embodiment, however, the appendage 118 lacks a fin core 122. Moreover, as seen in FIG. 20(a) the lead electrode assembly 100 of this embodiment further comprises a backing layer 130 and stitching 139. The backing layer 130 acts to insulate the electrode 107 so that cardioversion/ defibrillation energy may not pass to the tissue of the patient that surrounds the top surface 110 of the electrode 107. This has the effect of focusing the cardioversion/defibrillation energy toward the heart of the patient through the bottom surface 115 of the electrode 107.

The backing layer 130 comprises a base portion 158 and an integrated fin 120. The base portion 158 of the backing layer 130 comprises a first surface 131, a second surface 132, a first side 133 and a second side 134.

The base portion 158 of the backing layer 130 is attached to the electrode 107 such that the second surface 132 of the backing layer 130 lies directly adjacent to the top surface 110 of the electrode 107.

The base portion 158 of the backing layer 130 is formed so that the first side 133 and the second side 134 are substantially parallel and of substantially the same size as the first pair of sides 108 of the electrode 107.

Figure 20B:
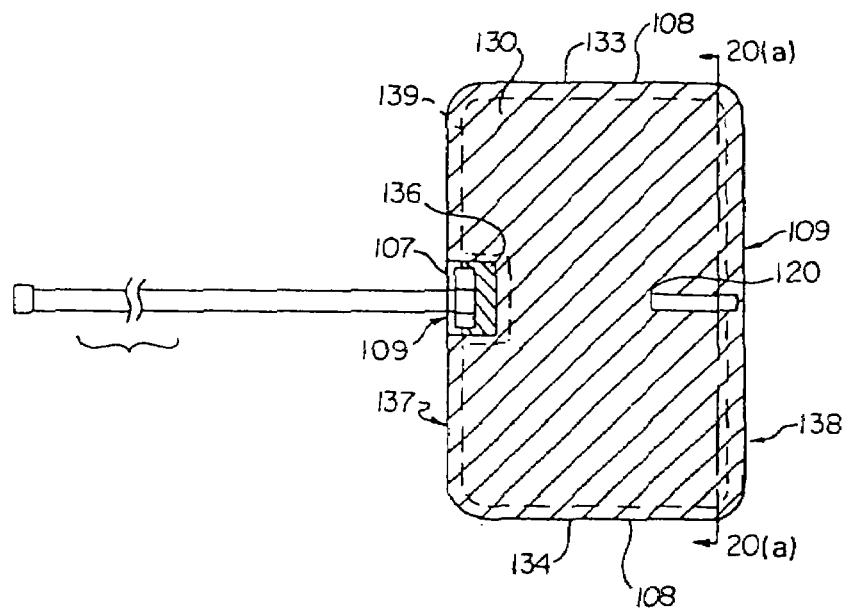
FIG. 20(b) is a top plan view of an embodiment of a lead electrode assembly with a top-mounted fin.

FIG. 20(b) illustrates a top view of the lead electrode assembly 100 of this embodiment. The base portion 158 of the backing layer 130 further comprises a distal end 137 and a proximal end 138.

The distal end 137 and proximal end 138 of the backing layer 130 are parallel to and of substantially the same size as the second pair of sides 109 (hidden) of the electrode 107. The backing layer 130 contains a notch 136 on its distal end 137, through which the lead fastener 146 rises.

The base portion 158 of the backing layer 130 is attached to the electrode 107 with stitching 139. The stitching is composed of nylon. In alternate embodiments, the stitching is composed of any polymeric material.

The backing layer 130 is composed of polyurethane. In an alternative embodiment, the backing layer is composed of molded silicone, nylon, or Dacron®. In alternative embodiments, the backing layer is composed of any polymeric material.

The integrated fin 120 of the backing layer 130 is formed from the same piece of material as the backing layer 130. The integrated fin 120 has the same shape and dimensions as the fin 120 of the embodiment in FIG. 19(b).

In one embodiment, the integrated fin 120 is reinforced with a layer of Dacron® polymer mesh attached to the integrated fin 120. In another embodiment, the integrated fin 120 is reinforced with a layer of any polymeric material.

Figure 21A:
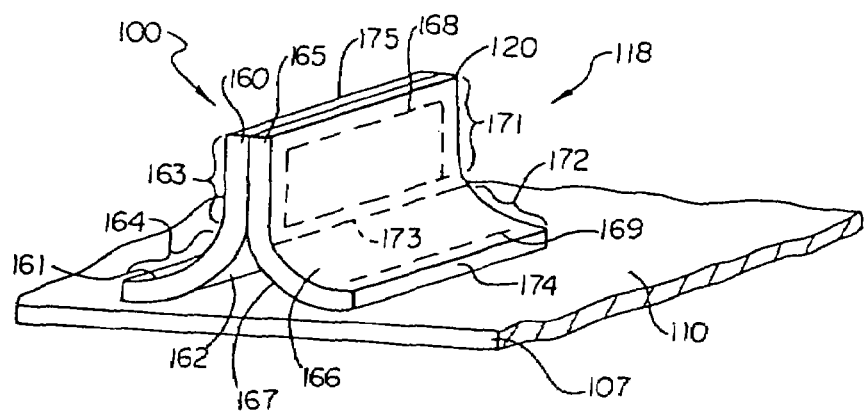
FIG. 21(a) is a perspective view of an embodiment of a lead electrode assembly with a top-mounted fin.

FIG. 21(a) illustrates an alternative embodiment of the lead electrode assembly 100. This embodiment is substantially similar to the lead electrode assembly 100 illustrated in FIGS. 19(a)-19(e). In this embodiment, however, the fin 120 has a different construction.

Here, fin 120 comprises a first fin section 165, a second fin section 160 and stitching 168. The first fin section 165 is a rectangular sheet of polymeric material comprising an inside face 167, an outside face 166, a first side 175 and a second side 174. The first side 175 and second side 174 of the first fin section 165 are substantially parallel and of substantially the same size.

A line 173 divides the first fin section 165 into a first half 171 and a second half 172. The line 173 runs parallel to the first side 175 of the first fin section 165. The first half 171 of the first fin section 165 lies on one side of line 173. The second half 172 of the first fin section 165 lies on the other side of the line 173.

The second fin section 160 is a rectangular sheet of polymeric material of the same size as the first fin section 165 comprising an inside face 162 and an outside face 161. The second fin section 160 is divided in half substantially similarly to the first fin section 165, thereby forming a first half 163 and a second half 164 of the second fin section 160.

In an alternate embodiment, the first fin section 165 and second fin section are not rectangular in shape. In an alternate embodiment, the first fin section 165 and second fin section have an oval shape.

The first half 171 of the first fin section 165 is fastened to the first half 163 of the second fin section 160. The inside face 167 of the first half 171 of the first fin section 165 faces the inside face 162 of the first half 163 of the second fin section 160. The first fin section 165 is fastened the second fin section 160 with stitching 168.

The fin 120 is attached to the top surface 110 of the electrode 107. To accomplish this, the second half 172 of the first fin section 165 is attached to the top surface 110 of the electrode 107 with the stitching 169. The second half 164 of the second fin section 160 is similarly attached to the top surface 110 of the electrode 107 with stitching (not shown).

In one embodiment, the fin 120 is reinforced with a layer of Dacron® polymer mesh positioned between the first fin section 165 and the second fin section 160 of the integrated fin 120. In another embodiment, the Dacrong polymer mesh is attached only to the first fin section 165 or the second fin section 160. In other embodiments, the integrated fin 120 is reinforced with a layer of any polymeric material attached to either or both fin sections.

The appendage height of the fin 120 in this embodiment is approximately 5 mm. In alternative embodiments, the appendage heights range between approximately 1 mm and approximately 10 mm. The appendage length of the fin 120 in this embodiment is approximately 1 cm. In alternative embodiments, appendage lengths range between approximately 2 mm and approximately 6 cm. In one embodiment, the appendage length of the fin 120 is such that the fin 120 is substantially as long as the electrode 107.

Figure 22A:
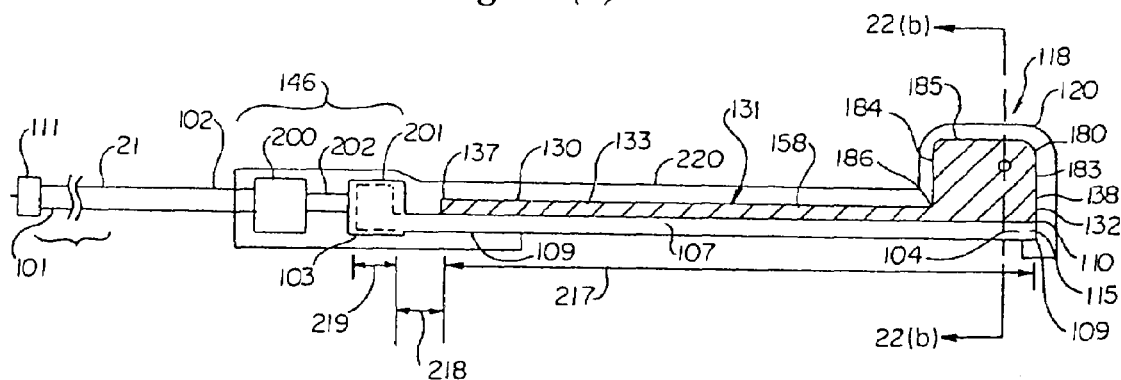
FIG. 22(a) is a cross-sectional side plan view of an embodiment of a lead electrode assembly with a top-mounted fin and a molded cover.

FIG. 22(a) illustrates a side plan view of an alternative embodiment of the lead electrode assembly 100. The lead electrode assembly 100 comprises a connector 111, a lead 21, a lead fastener 146, an electrode 107, a backing layer 130 with an integrated fin tab 180, a molded cover 220 and an appendage 118.

The connector 111 is connected to the lead 21. The lead 21 is further connected to the electrode 107 with the lead fastener 146. The backing layer 130 is positioned over the electrode 107. The fin tab 180 protrudes from the backing layer 130. The molded cover 220 is disposed around the lead fastener 146 and the backing layer 130. The molded cover 220 is further disposed around the fin tab 180 of the backing layer 118 to form the appendage 118. The molded cover 220 also partially envelops the electrode 107.

The connector 111 and the lead 21 are substantially similar to the connector 111 and the lead 21 described with reference to FIGS. 19(a)-19(f). The lead comprises a distal end 101 and a proximal end 102. The distal end 101 of the lead 21 is attached to the connector 111. The proximal end 102 of the lead 21 is connected to the electrode 107 by the lead fastener 146.

In this embodiment, the lead fastener 146 comprises a first crimping tube 200, a crimping pin 202 and a second crimping tube 201. The first crimping tube 200 connects the proximal end 102 of the lead 21 to the crimping pin 202. The second crimping tube 201 connects the crimping pin 202 to the electrode 107.

The electrode 107 comprises a distal end 103 (phantom view), a proximal end 104, a top surface 110 and a bottom surface 115. The electrode further comprises three sections: a main body 217, a mandrel 219 and a mandrel neck 218.

The main body 217 of the electrode 107 is the region of the electrode 107 that makes contact with the tissue of the patient and transfers the cardioversion/defibrillation energy to the patient. This region is substantially rectangular, comprising a first pair of sides 108 (not shown) and a second pair of sides 109. The first pair of sides 108 of the electrode 107 is substantially parallel to each other. The second pair of sides 109 of the electrode 107 is also substantially parallel to each other. In another embodiment, the first pair of sides 108 and the second pair of sides 109 of the electrode 107 are non-parallel. The main body 217 of the electrode 107 is positioned under the backing layer 130, so that the top surface 110 of the electrode faces the backing layer 130.

The mandrel 219 is a region of the electrode 107 shaped to facilitate the connection of the electrode 107 to the lead 21 via the lead fastener 146. The mandrel of the electrode is crimped onto to the crimping pin 202 of the lead fastener 146 with the second crimping tube 201, so that a robust physical and electrical connection is formed. The main body 217 of the electrode 107 is connected to the mandrel 219 of the electrode 107 via the mandrel neck 218 of the electrode 107.

The backing layer 130 comprises a base portion 158 and an integrated fin tab 180. The base portion 158 of the backing layer 130 comprises a first surface 131, a second surface 132, a distal end 137 and a proximal end 138.

The base portion 158 of the backing layer 130 is positioned such that its second surface 132 is adjacent to the top surface 110 of the electrode 107. The base portion 158 of the backing layer 130 is sized and positioned so that the distal end 137 and proximal end 138 of the base portion 158 of the backing layer 130 overlay the second pair of sides 109 of the main body 217 of the electrode 107. The distal end 137 and proximal end 138 of the base portion 158 of the backing layer 130 are also substantially parallel and of substantially the same size as the second pair of sides 109 of the electrode 107.

The integrated fin tab 180 of the backing layer 130 is formed from the same piece of material as the base portion 158 of the backing layer 130. The integrated fin tab 180 is formed on the first surface 131 of the base portion 158 of the backing layer 130.

The integrated fin tab 180 comprises a proximal edge 183, a distal edge 184, a top 185 and a bottom 186. The bottom 186 of the integrated fin tab 180 is joined to the first surface 131 of the base portion 158 of the backing layer 130. The proximal edge 183 and the distal edge 184 of the integrated fin tab 180 extend from, and substantially perpendicular to the first surface 131 of the base portion 158 of the backing layer 130. The proximal edge 183 and distal edge 184 of the integrated fin tab 180 are parallel with each other. The integrated fin tab 180 is positioned so that its proximal edge 183 is substantially flush with the proximal end 138 of the base portion 158 of the backing layer 130.

The backing layer 130 is composed of polyurethane. In an alternative embodiment, the backing layer 130 is composed of silicone. In another alternative embodiment, the backing layer 130 is composed of any polymeric material.

The molded cover 220 envelops and holds together the components of the lead electrode assembly 100. The molded cover 220 also provides rigidity to the lead electrode assembly 100. The molded cover 220 envelops the lead fastener 146 and the backing layer 130. The fin 120 is formed when the molded cover 220 covers the fin tab 180. The thickness of the resulting fin 120 is approximately 2 mm. In alternate embodiments, the thickness of the fin 120 is between approximately 1 mm and approximately 3 mm.

The appendage height of the fin 120 in this embodiment is approximately 5 mm. In alternative embodiments, the appendage heights range between approximately 1 mm and approximately 10 mm. The appendage length of the fin 120 in this embodiment is approximately 1 cm. In alternative embodiments, appendage lengths range between approximately 2 mm and approximately 6 cm. In one embodiment, the appendage length of the fin 120 is such that the fin is as long as the backing layer. In one embodiment, the appendage length of the fin 120 is such that the fin is as long as the electrode 107. In one embodiment, the appendage length of the fin 120 is such that the fin is as long as the molded cover 220.

The molded cover 220 also partially covers the bottom surface 115 of the electrode 107. In this way, the molded cover 220 attaches the backing layer 130 to the electrode 107.

The molded cover 220 in this embodiment is made of silicone. In an alternate embodiment, the molded cover 220 is made of any polymeric material. Stitching 360 holds the molded cover 220, the electrode 107 and the backing layer 130 together.

In one embodiment, the fin 120 is reinforced with a layer of Dacron® polymer mesh positioned between the molded cover 220 and the integrated fin tab 180. In another embodiment, the Dacron® polymer mesh is attached only to the molded cover 220. In other embodiments, the fin 120 is similarly reinforced with a layer of any polymeric material.

Figure 22B:
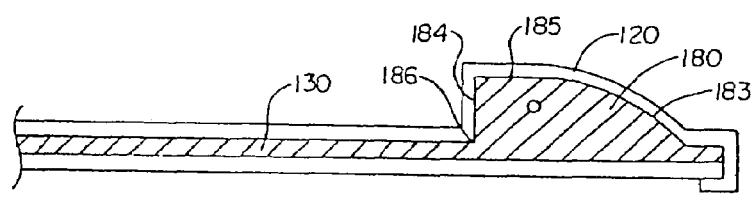
FIG. 22(b) is a cross-sectional side plan view of an embodiment of a lead electrode assembly with a top-mounted fin that is slope-shaped and a molded cover.

As shown in FIG. 22(b), the fin 120 of the embodiment illustrated in FIG. 22(a) can alternately have a sloped shape. The sloped shape can reduce the resistance offered by the tissue of the patient as it slides against the fin 120 during the insertion of the lead electrode assembly 100 into the patient. The slope-shaped fin 120 is constructed so that the proximal edge 183 and distal edge 184 of the integrated fin tab 180 are not parallel with each other. Instead, proximal edge 183 of the integrated fin tab 180 can be curved so that the proximal edge 183 of the integrated fin tab 180 is closer to the proximal edge 184 at the top 185 of the integrated fin tab 180, than at the bottom 186 of the integrated fin tab 180. In alternate embodiments, the proximal edge 183 of the integrated fin tab 180 is not curved. Instead, the proximal edge 183 of the integrated fin tab 180 is straight, and forms an acute angle with the first surface 131 of the backing layer 130. In one alternate embodiment, the proximal edge 183 of the integrated fin tab 180 forms a 45 degree angle with the first surface 131 of the backing layer 130. In alternate embodiments, the distal edge 184 of the integrated fin tab 180 is curved. In alternate embodiments, the distal edge 184 of the integrated fin tab 180 is straight and shaped so that it forms an acute angle with the first surface 131 of the backing layer 130.

Figure 22C:
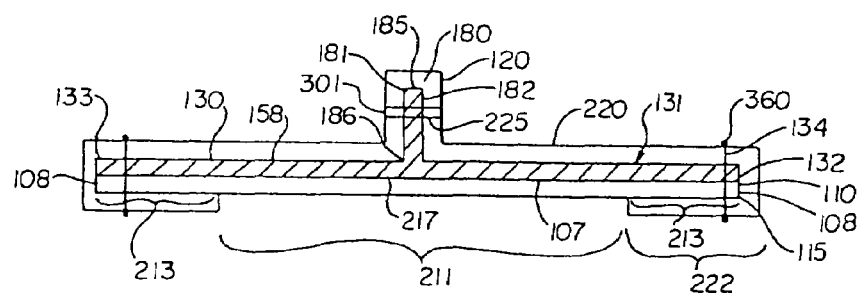
FIG. 22(c) is cross-sectional front plan view of an embodiment of a lead electrode assembly with a top-mounted fin and a molded cover.

FIG. 22(c) illustrates a front plan view of the lead electrode assembly 100 seen in FIG. 22(a). The base portion 158 of the backing layer 130 further comprises a first side 133 and second side 134. The first side 133 and second side 134 of the base portion 158 of the backing layer 130 are substantially parallel. In an alternate embodiment, the first side 133 and second side 134 of the backing layer 130 are not parallel. The base portion 158 of the backing layer 130 is sized so that it is substantially the same size and shape as the main body 217 of the electrode 107.

The integrated fin tab 180 of the backing layer 130 is planar, comprising a first face 181 and a second face 182. The first face 181 and second face 182 of the fin tab 180 are substantially parallel with each other and with the first side 133 and second side 134 of the backing layer 130. The first face 181 and second face 182 of the fin tab 180 extend from, and substantially perpendicular to the first surface 131 of the backing layer 130. In another embodiment, the first face 181 and second face 182 of the fin tab 180 extend from the first surface 131 of the backing layer 130 at angles other than a right angle.

In an alternate embodiment, the first face 181 and a second face 182 of the integrated fin tab 180 of the backing layer 130 are not substantially parallel to each other. Instead, they are angled, such that they are closer together at the top 185 than they are at the bottom 186 of the integrated fin tab 180. This shape can reduce the resistance offered by the tissue of the patient as it slides against the fin 120 during the insertion of the lead electrode assembly 100 into the patient.

In another embodiment, the first face 181 and a second face 182 of the integrated fin tab 180 of the backing layer 130 are angled, such that they are further apart at the top 185 than they are at the bottom 186 of the integrated fin tab 180. This shape can make the fin 120 easier to grip with a tool, such as a hemostat.

The fin tab 180 extends from the backing layer 130 at a position centered between the first side 133 and the second side 134 of the backing layer 130. In an alternate embodiment, the fin tab 180 is not centered between the first side 133 and the second side 134 of the backing layer 130.

An eyelet 301 is formed in the fin 120 of this embodiment. The eyelet can be used to facilitate the capture of the lead electrode assembly by a tool. The eyelet is formed as a hole 225 through the molded cover 220 and between the faces 181 and 182 of fin tab 180. In an alternate embodiment, no eyelet is formed in the fin 120.

The bottom surface 115 of the electrode 107 comprises a periphery 213 and a center 211. The molded cover 220 forms a skirt 222 around the periphery 213 of the bottom surface 115 of the electrode 107. The skirt 222 of the molded cover 220 covers the periphery 213 of the bottom surface 115 of the electrode 107.

The skirt 222 of the molded cover 220 can act to focus cardioversion/defibrillation energy emitted from the electrode 107 of the lead electrode assembly 100 toward the heart of the patient. Because the thorax of a patient is surrounded by a layer of fat that is somewhat conductive, the cardioversion/defibrillation energy may tend to arc through this layer to reach the active surface 15 of the canister 11 (seen in FIG. 1) without passing through the patient's heart. The skirt 222 of the lead electrode assembly 100 acts to minimize the loss of cardioversion/defibrillation energy to surrounding body tissues, or from being diverted away from the patient's heart.

The center 211 of the bottom surface 115 of the electrode 107 is not covered by the molded cover 220 and is left exposed. The width of the periphery 213 of the bottom surface 115 of the electrode 107 covered by the molded cover 220 is approximately 0.125 cm.

The area of the exposed center 211 of the bottom surface 115 of the electrode 107 is approximately 500 square mm. In alternative embodiments, the length of the first pair of sides 108 and the second pair of sides 109 of the electrode 107 varies, such that the area of the center 211 of the bottom surface 115 of the electrode has a surface area between approximately 100 sq. mm. and approximately 2500 sq. mm.

Figure 22D:
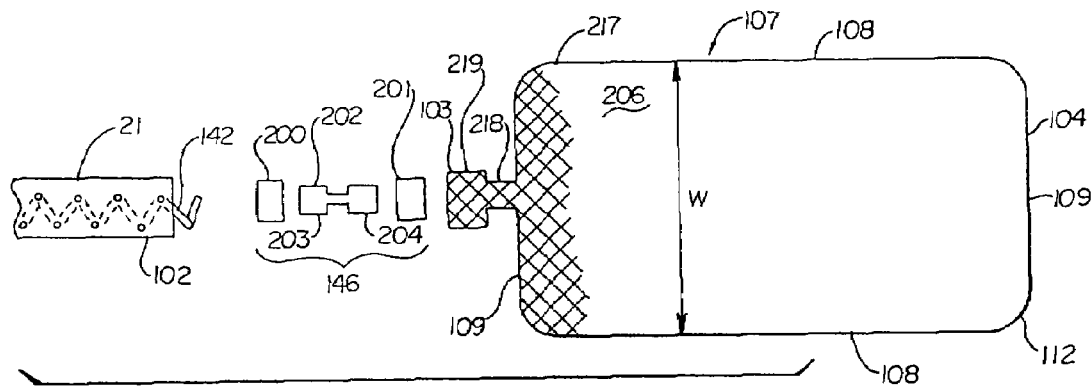
FIG. 22(d) is an exploded top plan view of the lead fastener in an embodiment of a lead electrode assembly with a top-mounted fin and a molded cover.

FIG. 22(d) illustrates an exploded top view of the lead fastener 146 of the embodiments illustrated in FIGS. 22(a)-22(c). The lead fastener connects the proximal end 102 of the lead 21 and the distal end 103 of the electrode 107.

In this embodiment, the lead fastener 146 comprises a first crimping tube 200, a crimping pin 202 and a second crimping tube 201. The crimping pin 202 comprises a first side 203 and a second side 204.

The crimping tube 200 crimps the filars 147 of the lead 21 (here, only one representative filar 147 is shown) to the first side 203 of crimping pin 202. The mandrel 219 of the electrode 107 is then wrapped around the second side 204 of the crimping pin 202. Crimping tube 201 crimps the mandrel 219 to the second side 204 of the crimping pin 202.

The first crimping tube 200, the second crimping tube 201 and the crimping pin 202 are each made of platinum iridium. In an alternative embodiment, the first crimping tube 200, the second crimping tube 201 and the crimping pin 202 are each made of a metal selected from the group consisting essentially of titanium, nickel alloys, stainless steel alloys, platinum, platinum iridium, and mixtures thereof. In other embodiments, the first crimping tube 200, the second crimping tube 201 and the crimping pin 202 each comprise any conductive material.

The electrode 107 in this embodiment comprises a sheet of metallic mesh 206 prepared by the process described with reference to FIG. 19(b). The electrode 107 has a width measured parallel to the second pair of sides 109 of the electrode 107. The width of the mandrel neck 218 of the electrode 107 is approximately 3 mm wide. The width of the mandrel of the electrode 107 is approximately 5 mm wide.

The first pair of sides 108 of the electrode 107 is approximately 5 cm in length. The second pair of sides 109 of the electrode 107 is approximately 1.9 cm in length. In alternative embodiments, the length of the first pair of sides 108 and the second pair of sides 109 of the electrode 107 ranges independently from approximately 1 cm to approximately 5 cm.

The electrode 107 of this embodiment further comprises four corners 112. The corners 112 of the electrode 107 are rounded. In an alternate embodiment, the corners 112 of the electrode 107 are not rounded.

Figure 22E:
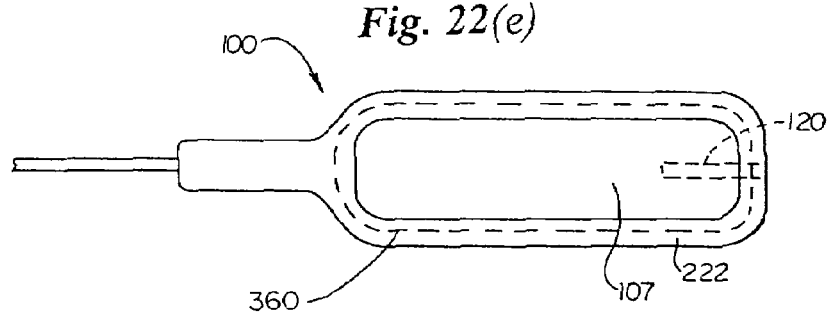
FIG. 22(e) is a bottom plan view of an embodiment of a lead electrode assembly with a top-mounted fin and a molded cover.
Figure 22F:
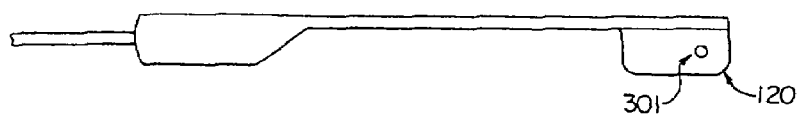
FIG. 22(f) is a side plan view of an embodiment of a lead electrode assembly with a top-mounted fin and a molded cover.
Figure 22G:
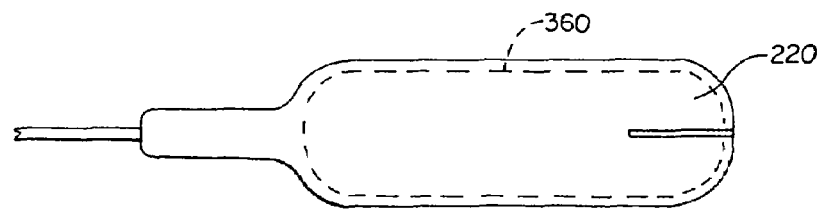
FIG. 22(g) is a top plan view of an embodiment of a lead electrode assembly with a top-mounted fin and a molded cover.

FIGS. 22(e)-22(g) illustrate the size and position of the fin 120 on the molded cover of the lead electrode assembly 100.

Figure 23A:
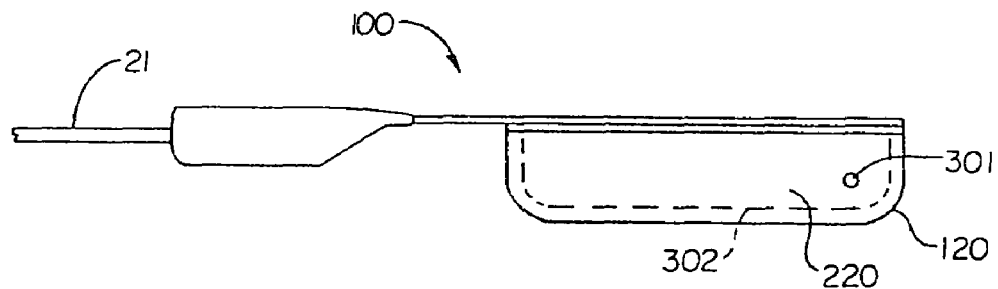
FIG. 23(a) is a side plan view of an embodiment of a lead electrode assembly with an elongated top-mounted fin and a molded cover.
Figure 23B:
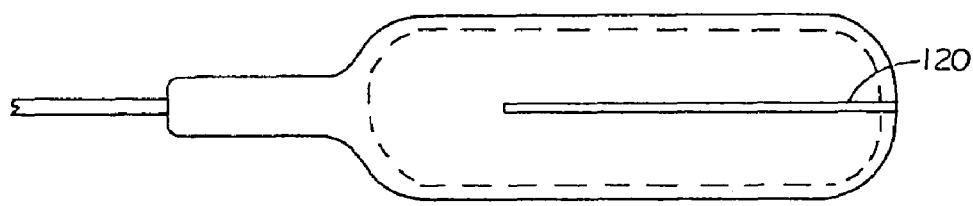
FIG. 23(b) is a top plan view of an embodiment of a lead electrode assembly with an elongated top-mounted fin and a molded cover.
Figure 23C:
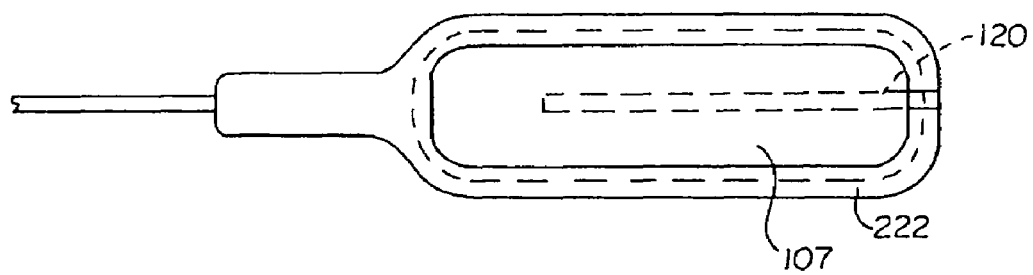
FIG. 23(c) is a bottom plan view of an embodiment of a lead electrode assembly with an elongated top-mounted fin and a molded cover.

FIGS. 23(a)-23(c) illustrate an alternative embodiment of the lead electrode assembly 100. This embodiment is substantially similar to the embodiments illustrated in FIGS. 22(a)-22(g). In this embodiment, however, the appendage height of the fin 120 is approximately 1 cm. The appendage length of the fin 120 in this embodiment is approximately 3.5 cm.

As shown in FIG. 23(a), stitching 302 is placed through the molded cover 220 and the fin 120 to prevent the molded cover 220 from sliding off the fin tab 180 when the molded cover 220 is subjected to a force directed away from the electrode 107.

As shown in FIG. 23(c), the fin 120 (phantom view) extends approximately two thirds of the length of the electrode 107.

Figure 24:
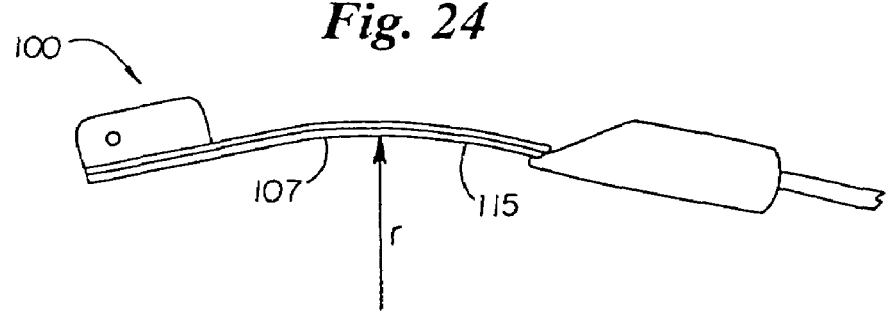
FIG. 24 is a side plan view of a lead electrode assembly demonstrating the curvature of the electrode.

FIG. 24 illustrates an alternative embodiment of the lead electrode assembly 100. This embodiment is substantially similar to the embodiments illustrated in FIGS. 22(a)-22(g). In this embodiment, however, the backing layer 130 (not shown) inside the molded cover 220 is curved. This results in an electrode 107 that has a curvature of radius r, such that the bottom surface 115 of the electrode 107 is concave.

Because a curved electrode 107 may more closely approximate the curvature of the patient's ribs, this curvature may have the effect of making the lead electrode assembly 100 more comfortable for the patient. In one embodiment, the radius r of the curvature varies throughout the electrode 107 such that it is intentionally shaped to approximate the shape of the ribs. Lead electrode assemblies 100 can be custom manufactured with an electrode 107 with a curvature r that matches the curvature of the intended patient's ribcage in the vicinity of the ribcage adjacent to which the electrode 107 is to be positioned.

In an alternative embodiment, lead electrode assemblies 100 are manufactured with an electrode 107 with a radius r that matches the curvature of the ribcage of a statistically significant number of people.

In another embodiment, lead electrode assemblies 100 with electrodes 107 of varying curvatures can be manufactured to allow an electrode radius r to be selected for implantation based on the size of the patient. Smaller radii can be used for children and for smaller adult patients. Larger radii can be used for larger patients. The radius r of the curvature can range from approximately 5 cm to approximately 35 cm depending on the size of the patient.

In an alternative embodiment, the electrode 107 of the lead electrode assembly 100 is flexible, such that it can be bent to conform to the curvature of the intended patient's rib cage at the time of implantation.

Figure 25A:
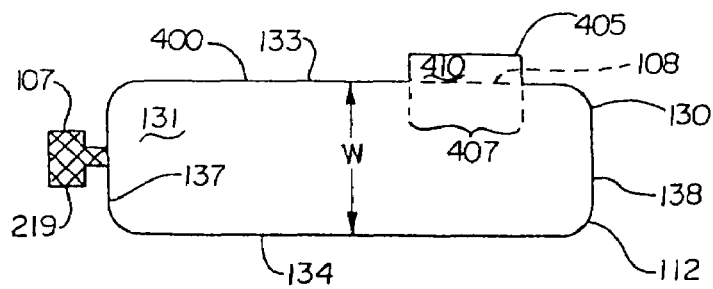
FIG. 25(a) is a top plan view of the backing layer and electrode of an embodiment of a lead electrode assembly with a side-mounted fin.
Figure 25B:
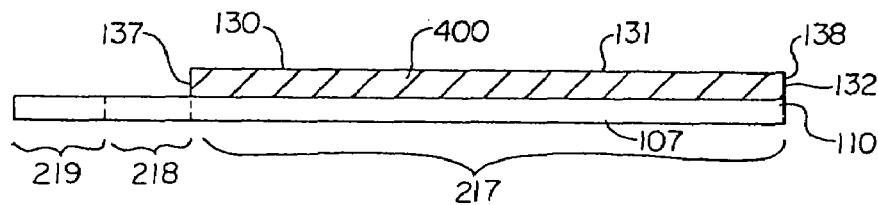
FIG. 25(b) is a side plan view of the backing layer and electrode of an embodiment of a lead electrode assembly with a side-mounted fin.
Figure 25C:
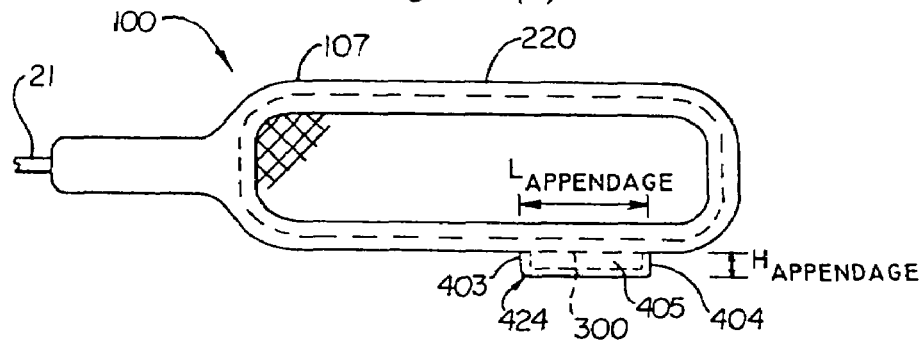
FIG. 25(c) is a bottom plan view of an embodiment of a lead electrode assembly with a side-mounted fin.

FIGS. 25(a)-25(c) illustrate an alternative embodiment of the lead electrode assembly 100. This embodiment is substantially similar to the embodiments illustrated in FIGS. 22(a)-22(g). In this embodiment, however, the backing layer 130 lacks an integrated fin tab 180 mounted on the first surface 131 of the backing layer 130. Moreover, this embodiment further comprises a backing layer 400 having a fin tab 405.

FIGS. 25(a) and 25(b) illustrate only the backing layer 400, the fin tab 405 and the electrode 107 of this embodiment as they are positioned relative to each other in the complete embodiment. Other components of the embodiment are not shown. FIG. 25(c) shows the embodiment in a complete form.

FIG. 25(a) illustrates a top plan view of the backing layer 400 and the electrode 107. The backing layer 400 is positioned over the electrode 107. The electrode 107 of this embodiment is substantially similar to the electrode 107 of the embodiment illustrated in FIG. 22(d). In the complete embodiment, the mandrel 219 of the electrode 107 is joined to the lead 21 (not shown) by a lead fastener 146 (not shown) as shown in FIG. 22(a).

The backing layer 400 is a flat, planar member comprising a distal end 137 and a proximal end 138. The backing layer 400 further comprises a first side 133, a second side 134, a first surface 131, and a second surface 132 (not shown). The backing layer 400 further comprises a width, W, measured as the distance between the first side 133 and the second side 134.

The backing layer 400 includes a fin tab 405 that is formed from the same piece of material as the backing layer 400. The first side 133 of the backing layer 400 lies over one of the first pair of sides 108 of the electrode 107 except over a fin tab region 407. In the fin tab region 407, the backing layer 400 is wider than the electrode 107. In the fin tab region 407, the first side 133 forms a fin tab 405 that protrudes from part of the first side 133 of the backing layer 400 outside the fin tab region 407. The fin tab 405 extends from the first side 133 of the backing layer 400 in an orientation substantially parallel to the top surface 110 of the electrode 107, beyond the first side 108 (phantom view) of the electrode 107.

The fin tab 405 comprises a first face 410 and a second face 411 (not shown). The first face 410 of the fin tab 405 is an extension of the first surface 131 of the backing layer 400. The second face 411 of the fin tab 405 is an extension of the second surface 132 of the backing layer 400.

Aside from the fin tab 405, the backing layer 405 is formed so that it is of substantially the same size and shape as the main body 217 of the electrode 107.

The backing layer 400, including the fin tab 405, is composed of polyurethane. In an alternate embodiment, the backing layer 400 and fin tab 405 are composed of any polymeric material.

FIG. 25(b) is a side plan view of the backing layer 400 and the electrode 107. The backing layer 400 is positioned over the electrode 107 such that the second surface 132 of the backing layer 400 is placed adjacent to the top surface 110 of the electrode 107.

FIG. 25(c) illustrates a bottom plan view of the complete embodiment, in which the backing layer 400 (not shown), the lead fastener 146 (not shown) and the fin tab 405 (phantom view) are coated with a molded cover 220. When the molded cover 220 is applied over the backing layer 400, a fin 424 is formed over the fin tab 405 (phantom view). The fin 424 comprises a proximal end 404 and a distal end 403.

In one embodiment, the fin 424 is reinforced with a layer of Dacron® polymer mesh positioned between the molded cover 220 and the fin tab 405. In another embodiment, the Dacron® polymer mesh is attached only to the molded cover 220. In other embodiments, the fin 424 is similarly reinforced with a layer of any polymeric material.

The appendage height, $h_{Appendage}$, of the fin 424 of this embodiment is approximately 5 mm. In alternative embodiments, the appendage heights range between approximately 1 mm and approximately 10 mm. The appendage length, $L_{Appendage}$, of the fin 424 of this embodiment is measured between the proximal end 404 and the distal end 403 of the fin 424. $L_{Appendage}$ is measured where the fin 424 joins the rest of the lead electrode assembly 100. In this embodiment, the appendage length is approximately 1 cm. In alternative embodiments, the appendage lengths range between approximately 2 mm and approximately 6 cm. In one embodiment, the appendage length of the fin 424 is such that the fin 424 runs the length of the electrode 107. In one embodiment, the appendage length of the fin 424 is such that the fin 424 runs the length of the backing layer 130 (not shown). In one embodiment, the appendage length of the fin 424 is such that the fin 424 runs the length of the molded cover 220.

Figure 25D:
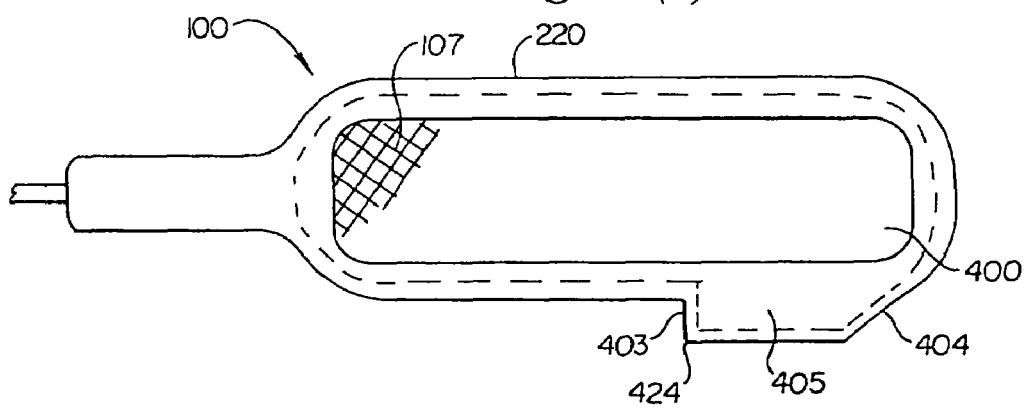
FIG. 25(d) is a bottom plan view of an embodiment of a lead electrode assembly with a side-mounted fin with a sloped shape.

FIG. 25(d) illustrates a bottom plan view of an alternate embodiment of the lead electrode assembly 100. This embodiment is substantially similar to the lead electrode assembly 100 illustrated in FIGS. 25(a)-25(c). In this embodiment, however, proximal end 404 of the fin 424 is sloped. The sloped shape of the fin 424 is formed by the shape of the fin tab 405 (phantom view) inside the fin 424. The backing layer 400 gradually widens in the fin tab region 407 (not shown) with distance from the proximal end 138 (not shown) to the distal end 137 (not shown) of the backing layer 130 (not shown) until the appendage height is reached. The proximal end 404 of the fin 424 is straight and forms an acute angle with the first side 133 of the base portion 158 of the backing layer 130 (not shown). In an alternate embodiment, the proximal end 404 of the fin 424 forms a 45 degree angle with the first side 133 of the base portion 158 of the backing layer 130 (not shown). In another embodiment, the proximal end 404 of the fin 424 is curved slope.

In alternate embodiments, the distal end 403 of the fin 424 is straight and shaped so that it forms an acute angle with the first side 133 of the base portion 158 of the backing layer 130 (not shown). In alternate embodiments, the distal end 403 of the fin 424 is curved.

Figure 26A:
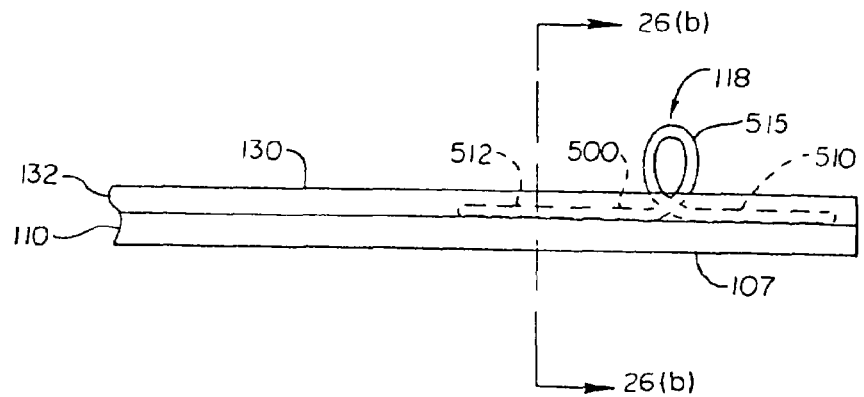
FIG. 26(a) is a side plan view of a lead electrode assembly with a top-mounted loop.
Figure 26B:
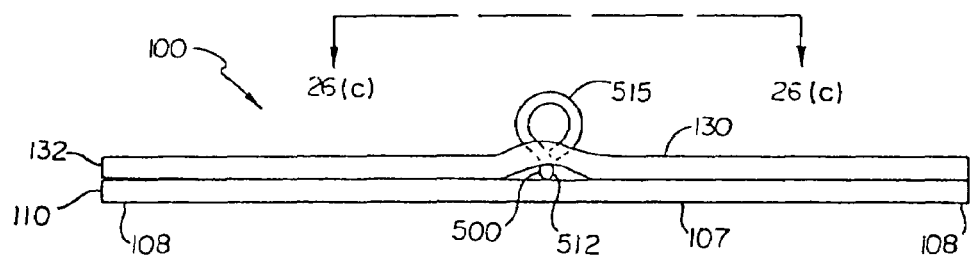
FIG. 26(b) is a cross-sectional rear plan view of a lead electrode assembly with a top-mounted loop.
Figure 26C:
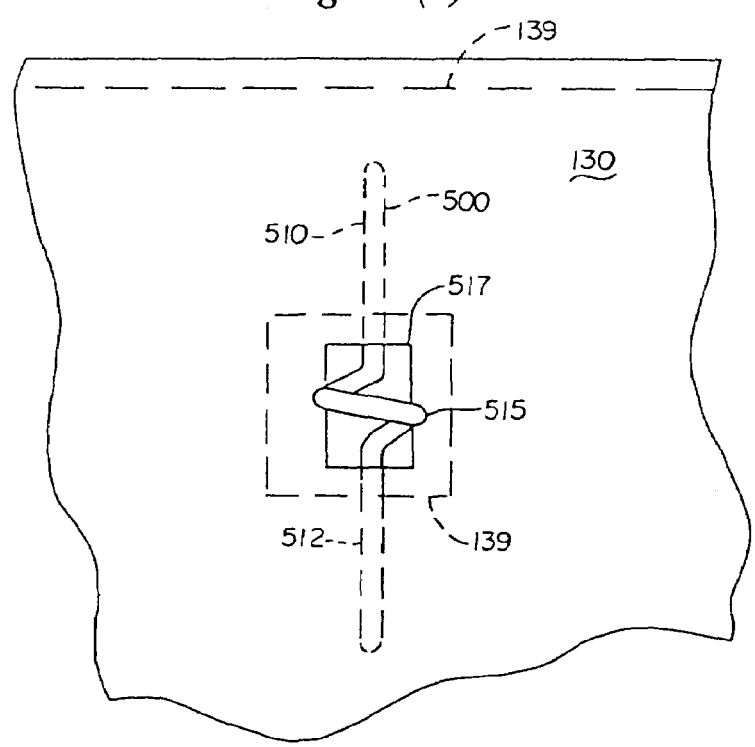
FIG. 26(c) is a top plan view of a lead electrode assembly with a top-mounted loop.

FIGS. 26(a)-26(c) illustrate an alternative embodiment of the lead electrode assembly 100. This embodiment is substantially similar to the embodiment illustrated in FIGS. 20(a)-20(b). The integrated fin 120 is absent, however, from the backing layer 130.

The lead electrode assembly 100 of this embodiment further comprises a cylindrical rod 500 having a loop 515 formed therein. The loop 515 comprises the appendage 118 of this embodiment. The loop 515 is a member attached to the electrode 107 that can be gripped and used to precisely locate the electrode 107 during its surgical implantation within the patient.

FIG. 26(a) illustrates a side plan view of the embodiment. The cylindrical rod 500 comprises a first straight portion 510, a second straight portion 512 and a portion formed into a loop 515. The first straight portion 510 is separated from the second straight portion 512 by the loop 515.

The rod 500 is made of platinum iridium. In an alternative embodiment, the rod 500 is made of titanium or platinum.

The first straight portion 510 and second straight portion 512 are spot welded to the top surface 110 of the electrode 107. The loop 515 in the rod 500 extends away from the top surface 110 of the electrode 107.

The backing layer 130 is similar to the backing layer 130 illustrated in FIGS. 20(a)-20(b). The backing layer 130 is disposed over the electrode 107. The first straight portion 510 and second straight portion 512 of the rod 500 are positioned between the second surface 132 of the backing layer 130 and the top surface 110 of the electrode 107.

FIG. 26(b) illustrates a cross-sectional rear plan view of the embodiment of the lead electrode assembly shown in FIG. 26(a). The first straight portion 510 and second straight portion 512 are positioned such that they are parallel to the first pair of sides 108 of the electrode 107. The first straight portion 510 and second straight portion 512 are both centered between the first pair of sides 108 of the electrode 107. In an alternative embodiment, the first straight portion 510 and second straight portion 512 are not parallel to and centered between the first pair of sides 108 of the electrode 107.

FIG. 26(c) illustrates a top plan view of the embodiment of the lead electrode assembly shown in FIG. 26(a). An aperture 517 is formed in the backing layer 130. The aperture 517 in the backing layer is positioned such that the loop 515 extends through and beyond the aperture 517 in a direction away from the top surface 110 of the electrode 107. The backing layer 130 is attached to the electrode 107 with stitching 139.

FIGS. 27(a)-27(d) illustrate an alternative embodiment of the lead electrode assembly 100. This embodiment is substantially similar to the embodiment illustrated in FIGS. 20(a)-20(b). This embodiment comprises a backing layer 610, however, that lacks the integrated fin 120 illustrated in FIGS. 20(a)-20(b).

Figure 27A:
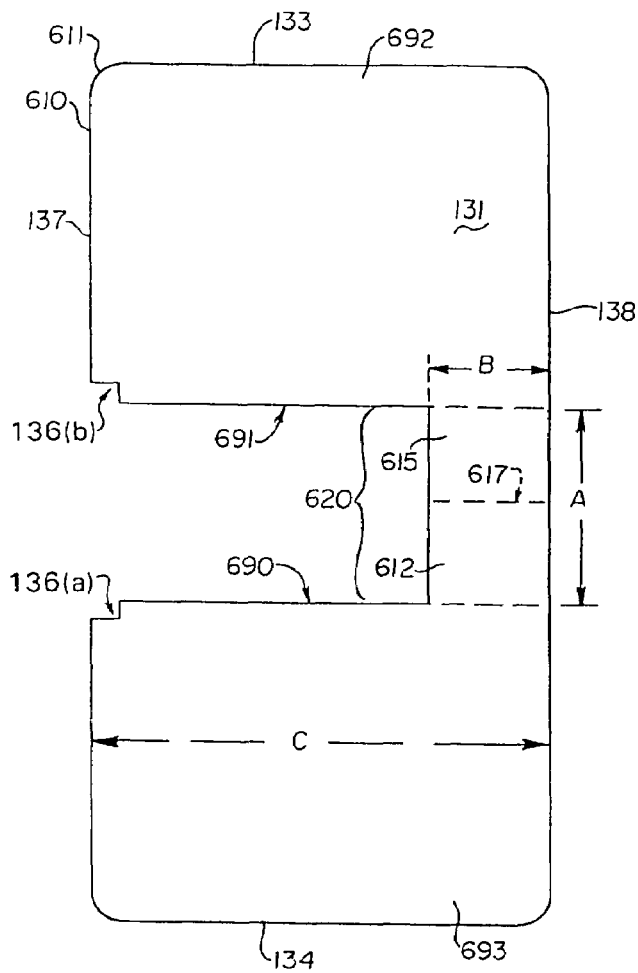
FIG. 27(a) is a top plan view of a backing layer for use in an embodiment of a lead electrode assembly with a top-mounted fin formed as part of the backing layer.

FIG. 27(a) illustrates a top plan view of the backing layer 610 of this embodiment prior to its attachment to the rest of the lead electrode assembly 100. The backing layer 610 is cut in a pattern as shown. The backing layer comprises a first surface 131, a second surface 132 (not shown), a distal end 137, a proximal end 138, a first side 133, a second side 134 and an indented fin-forming region 620. The indented fin-forming region 620 comprises a first edge 690 and a second edge 691.

The backing layer 610 is formed so that the first side 133 and the second side 134 are substantially parallel and of substantially the same size as the first pair of sides 108 of the electrode 107. The proximal end 138 is formed so that it is substantially perpendicular to the first side 133 and the second side 134 of the backing layer 610. The proximal end 138 is longer than the second pair of sides 109 of the electrode 107 by a length A. The backing layer 610 has a varying width C measured from its distal end 137 to its proximal end 138 along a line parallel to its first side 133.

The backing layer is divided into three sections. A first backing section 693, a second backing section 692 and an indented fin-forming region 620 of length A. The length of the fin-forming region 620, A, is approximately 10 mm. In other embodiments, the length of the fin-forming region 620, A, ranges between approximately 2 mm and approximately 20 mm.

The area within the indented fin-forming region 620 is equally divided into a first fin area 612 and a second fin area 615. The dividing line 617 between the first fin area 612 and the second fin area 615 is substantially parallel to the first side 133.

The width, C, of the backing layer 610 is equal to the distance between the second pair of sides 109 of the electrode 107 except in the indented fin-forming region 620. In the indented fin-forming region 620, the width, C, of the backing layer 610 is B. The width, B, of the backing layer 610 in the fin-forming region 620, is approximately 1 cm. In alternate embodiments, the width, B, of the backing layer 610 in the fin-forming region 620 ranges between approximately 2 mm and approximately 6 cm. In other embodiments, however, the fin-forming region 620 ranges between 2 mm and the width, C, of the backing layer 610. In other embodiments, the fin-forming region 620 is longer than the width, C, of the backing layer 610.

The variation in width between the areas inside and outside the indented fin-forming region 620 forms the first edge 690 and a second edge 691 of the fin-forming region 620.

A first notch 136(a) is formed on the distal end 137 the first edge 690 of the fin-forming region 620 of the backing layer 130. A second notch 136(b) is formed on the distal end 137 the second edge 691 of the fin-forming region 620 of the backing layer 130.

The backing layer 610 in this embodiment is formed of flexible silicone. In alternative embodiments the backing layer 610 is formed of any bio-compatible, flexible polymeric material.

Figure 27B:
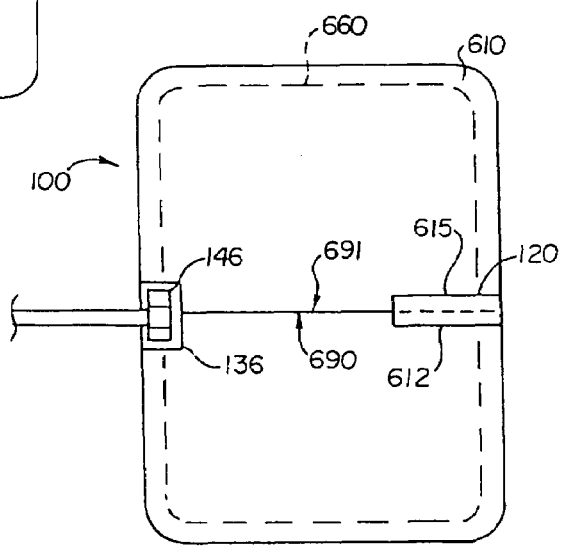
FIG. 27(b) is a top plan view of an embodiment of a lead electrode assembly with a top-mounted fin formed as part of the backing layer.

FIG. 27(b) illustrates a top plan view of the lead electrode assembly 100 of this embodiment. The backing layer 610 is attached to the electrode 107, so that the first edge 690 and a second edge 691 of the fin-forming region 620 of the backing layer 610 meet. This causes the backing layer 610 in the first fin area 612 and the second fin area 615 to fold together to form a fin 120.

The first notch 136(a) and second notch 136(b) formed on the distal end 137 the first edge 690 and second edge 691 of the fin-forming region 620 of the backing layer 130 meet to form a notch 136 on the distal end 137 of the backing layer, through which the lead fastener 146 rises. Stitching 660 holds the backing layer to the electrode 107.

Figure 27C:
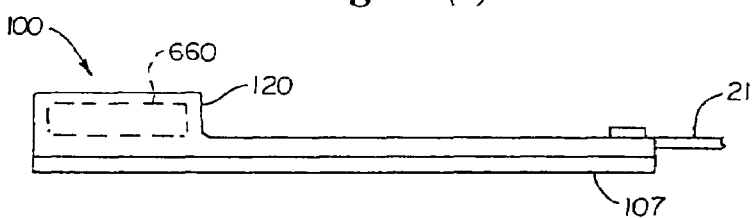
FIG. 27(c) is a side plan view of an embodiment of a lead electrode assembly with a top-mounted fin formed as part of the backing layer.

FIG. 27(c) illustrates a side plan view of the lead electrode assembly 100 of this embodiment. Stitching 660 holds the first fin area 612 and a second fin area 615 of the backing layer 610 together to form the fin 120.

Figure 27D:
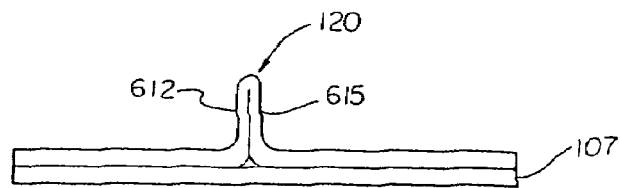
FIG. 27(d) is a front plan view of an embodiment of a lead electrode assembly with a top-mounted fin formed as part of a backing layer.

FIG. 27(d) illustrates a front plan view of the lead electrode assembly 100 of this embodiment. In one embodiment, the fin 120 is reinforced with a layer of Dacron® polymer mesh positioned between the first fin area 612 and a second fin area 615. In another embodiment, the Dacron® polymer mesh is attached only to either first fin area 612 or the second fin area 615. In other embodiments, the fin 120 is similarly reinforced with a layer of any polymeric material.

Figure 27E:
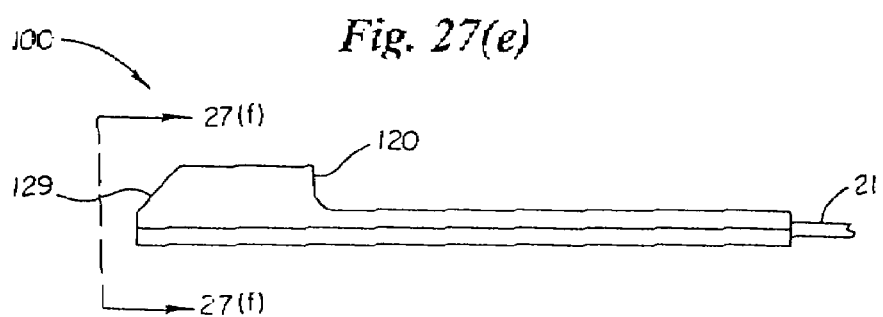
FIG. 27(e) is a side plan view of an embodiment of a lead electrode assembly with a top-mounted fin formed as part of a two-piece backing layer.
Figure 27F:
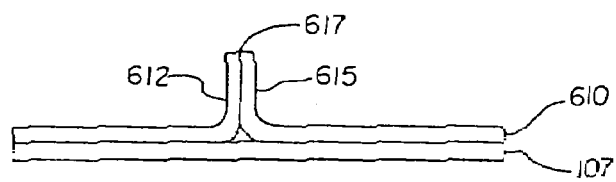
FIG. 27(f) is a front plan view of an embodiment of a lead electrode assembly with a top-mounted fin formed as part of a two-piece backing layer.

FIGS. 27(e) and 27(f) illustrate an alternative embodiment of the lead electrode assembly 100. This embodiment is substantially similar to the embodiment illustrated in FIGS. 27(a)-27(d). The backing layer 610 is substantially similar to the backing layer 610 illustrated in FIG. 27(a). The backing layer 610 in this embodiment, however, is cut along line 617. The fin 120 of this embodiment comprises a proximal edge 129. The proximal edge 129 of the fin 120 is slope-shaped. The sloped shape can reduce the resistance offered by the tissue of the patient as it slides against the fin 120 during the insertion of the lead electrode assembly 100 into the patient.

Figure 28A:
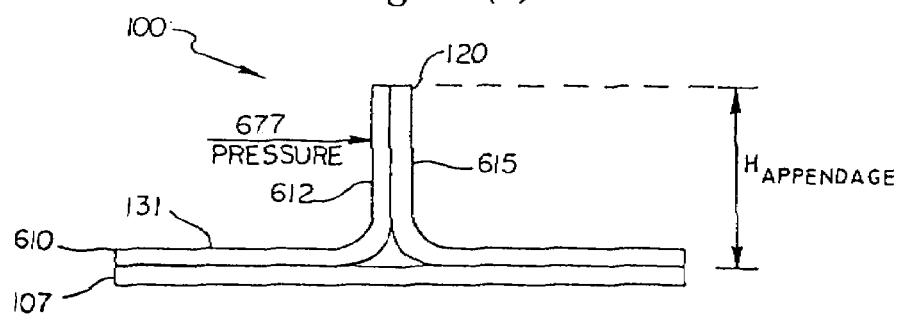
FIG. 28(a) is a front plan view of the embodiment of the lead electrode assembly of FIGS. 27(e) and (f) in an upright position.
Figure 28B:
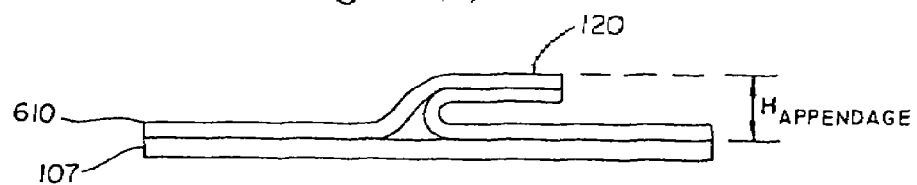
FIG. 28(b) is a front plan view of the embodiment of the lead electrode assembly of FIGS. 27(e) and (f) illustrating the ability of the fin to fold.

FIGS. 28(*a*) and 28(*b*) illustrate a property of the embodiment of the lead electrode assembly 100 illustrated in FIGS. 27(*e*) and 27(*f*). The backing layer 610 is flexible, such that the substantially planar fin 120 formed therefrom is flexible and able to fold. Because the ability of the fin 120 to fold effectively reduces its appendage height, it may make the fin more comfortable to the patient after it is implanted.

FIG. 28(*a*) shows fin 120 in an upright condition. When pressure is applied perpendicular to the first surface 131 of backing layer in the first fin area 612, along line 677 for example, the fin 120 folds as shown in FIG. 28(*b*). When the fin 120 folds, its appendage height, $H_{Appendage}$, is reduced. This can be seen by a comparison between FIG. 28(*a*) and FIG. 28(*b*).

The backing layer 610 in this embodiment is formed of a polymeric material. In an alternative embodiment, the backing layer 610 is formed of any bio-compatible, flexible polymeric material.

Figure 29A:
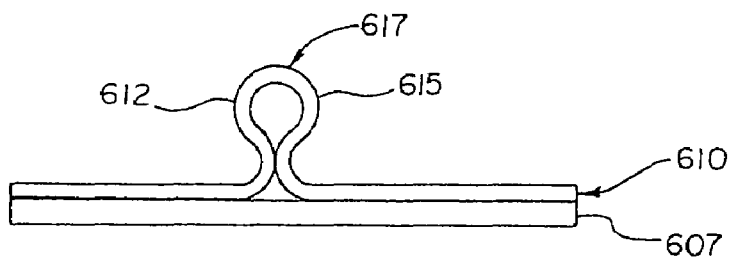
FIG. 29(a) is a front plan view of an embodiment of a lead electrode assembly with a top-mounted tube formed as part of a backing layer.
Figure 29B:
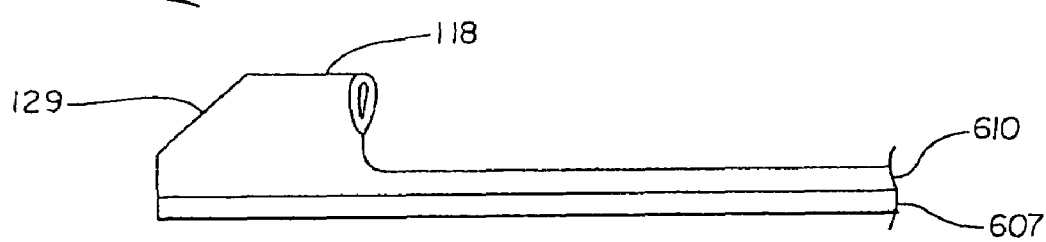
FIG. 29(b) is a side plan view of an embodiment of a lead electrode assembly with a top-mounted tube formed as part of a backing layer.
Figure 29C:
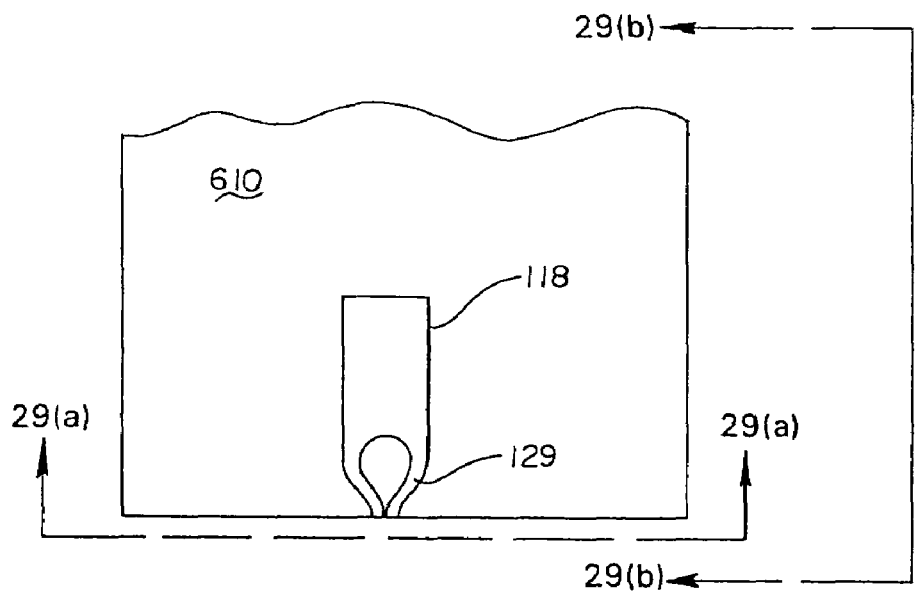
FIG. 29(c) is a top plan view of an embodiment of a lead electrode assembly with a top-mounted tube formed as part of a backing layer.

FIGS. 29(*a*)-29(*c*) illustrate an alternative embodiment of the lead electrode assembly 100. This embodiment is substantially similar to the embodiment illustrated in FIGS. 27(*a*)-27(*d*).

As shown in FIG. 29(*a*), however, the material from the first fin area 612 and the second fin area 615 of the backing layer 610 is not fastened together with stitching 660 in this embodiment. The resulting appendage 118 is formed in the shape of a tube.

In alternate embodiments, the backing layer 610 is coupled to the electrode 107 such that the material from the first fin area 612 and the second fin area 615 of the backing layer 610 does not touch except at the dividing line 617 between the first fin area 612 and the second fin area 615. The separation between the first fin area 612 and the second fin area 615 of the backing layer 610 can allow the appendage 118 of this embodiment to be highly flexible. This flexibility can reduce the resistance offered by the tissue of the patient as it slides against the appendage 118 during the insertion of the lead electrode assembly 100 into the patient.

FIG. 29(*b*) illustrates a side plan view of the embodiment illustrated in FIG. 29(*a*). The appendage 118 of this embodiment comprises a proximal edge 129. The proximal edge 129 of the appendage 118 is slope-shaped. The sloped shape can reduce the resistance offered by the tissue of the patient as it slides against the appendage 118 during the insertion of the lead electrode assembly 100 into the patient.

In alternate embodiments, the proximal edge 129 of the tube formed by the appendage 118 is closed. In one embodiment, the proximal edge 129 of the appendage 118 is closed by a cap (not shown). In another embodiment, the proximal edge 129 of the appendage 118 is closed with stitching placed between the first fin area 612 and the second fin area 615 only at the proximal edge 129 of the appendage 118. In another embodiment, the proximal edge 129 of the appendage 118 is closed by any other means known in the art for this purpose.

FIG. 29(*b*) illustrates a top plan view of the embodiment illustrated in FIGS. 29(*a*)-29(*b*).

Figure 30A:
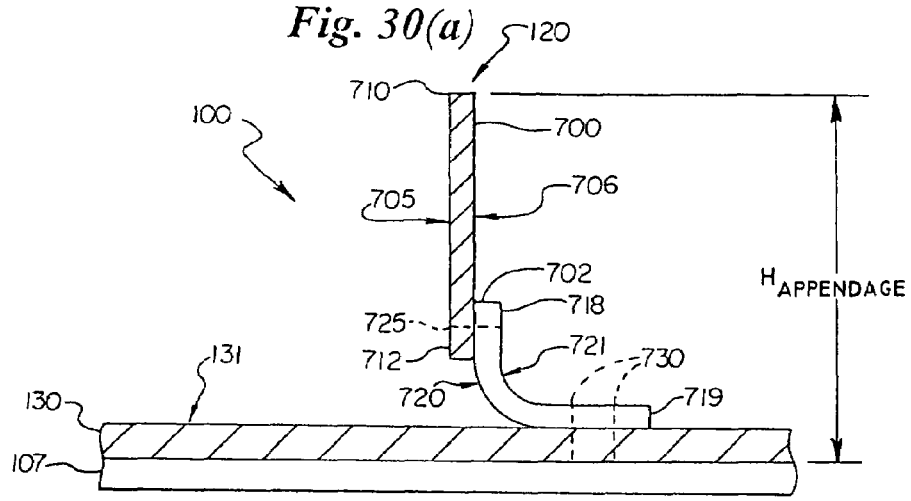
FIG. 30(a) is a front plan view of an embodiment of a lead electrode assembly with a top-mounted fin connected with flexible joining material in an upright position.
Figure 30B:
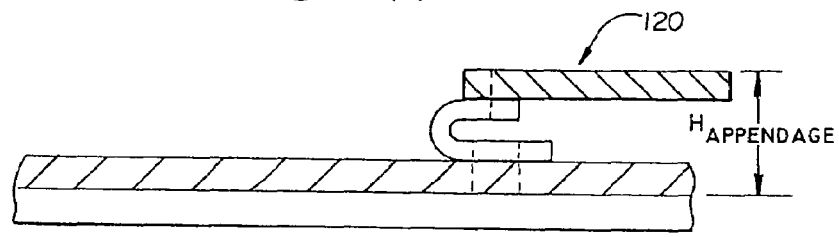
FIG. 30(b) is a front plan view of an embodiment of a lead electrode assembly with a top-mounted fin connected with flexible joining material in a folded position.
Figure 30C:
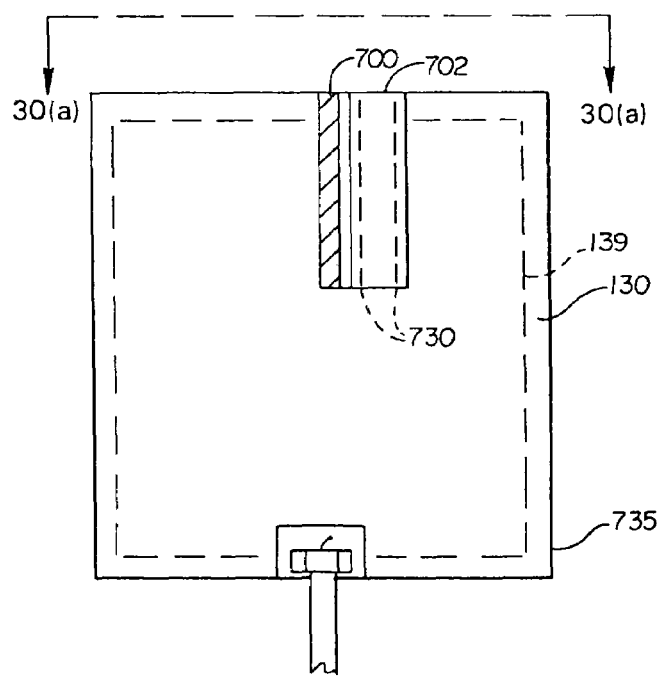
FIG. 30(c) is a top plan view of an embodiment of a lead electrode assembly with a top-mounted fin connected with flexible joining material in an upright position.

FIGS. 30(*a*)-30(*d*) illustrate an alternative embodiment of the lead electrode assembly 100. This embodiment is substantially similar to the embodiment illustrated in FIGS. 20(*a*)-20(*b*). The backing layer 130 of this embodiment, however, lacks an integrated fin 120.

FIG. 30(*a*) illustrates a front plan view of the lead electrode assembly 100. The fin 120 in this embodiment comprises a fin head 700 and flexible joining material 702.

The fin head 700 comprises a rectangular sheet having a first face 705, a second face 706, a first end 710 and a second end 712. The fin head 700 further comprises a height measured along the first face 705 between the first end 710 and the second end 712 and a length measured perpendicular to its height.

The fin head 700 is made of rigid silicone, which has a high durometer. In alternate embodiments, the fin head 700 is composed of any rigid bio-compatible material, such as a rigid bio-compatible polymeric material.

The flexible joining material 702 comprises a rectangular sheet having a first face 720, a second face 721, a first end 718 and a second end 719. The flexible joining material 702 further comprises a height measured along the first face between the first end 718 and the second end 719. The flexible joining material 702 also comprises a length measured perpendicular to its height. The length of the flexible joining material 702 is the same as the length of fin head 700.

The second end 712 of the second face 706 of the fin head 700 is attached to the first end 718 of the first face 720 of the flexible joining material 702. The fin head 700 is attached to the flexible joining material 702 with stitching 725. The second end 719 of the first face 720 of the flexible joining material 702 is attached to the first surface 131 of the backing material 130. The flexible joining material 702 is attached to the backing material 130 with stitching 730.

The flexible joining material 702 is made of flexible silicone. It will be recognized by one skilled in the art, however, that the flexible joining material 702 may be made from many other flexible materials, such as a flexible polymeric material.

FIG. 30(*b*) illustrates a property of the fin 120. When pressure is applied perpendicular to the first surface 705 of the fin head 205, the fin 120 folds as shown. When the fin 120 folds, its appendage height, $H_{Appendage}$, is reduced. This can be seen by a comparison between FIG. 30(*a*), which shows the fin 120 in an upright position and FIG. 30(*b*) that shows the fin 120 in a folded position.

FIG. 30(*c*) illustrates a top planar view of the lead electrode assembly 100 of the embodiment illustrated in FIGS. 30(*a*)-30(*b*). Neither the corners of the electrode 107 nor the corners 735 of the backing layer 130 of this embodiment are rounded. In an alternate embodiment, both the corners of the electrode 107 and the corners 735 of the backing layer 130 of this embodiment are rounded.

Figure 31:
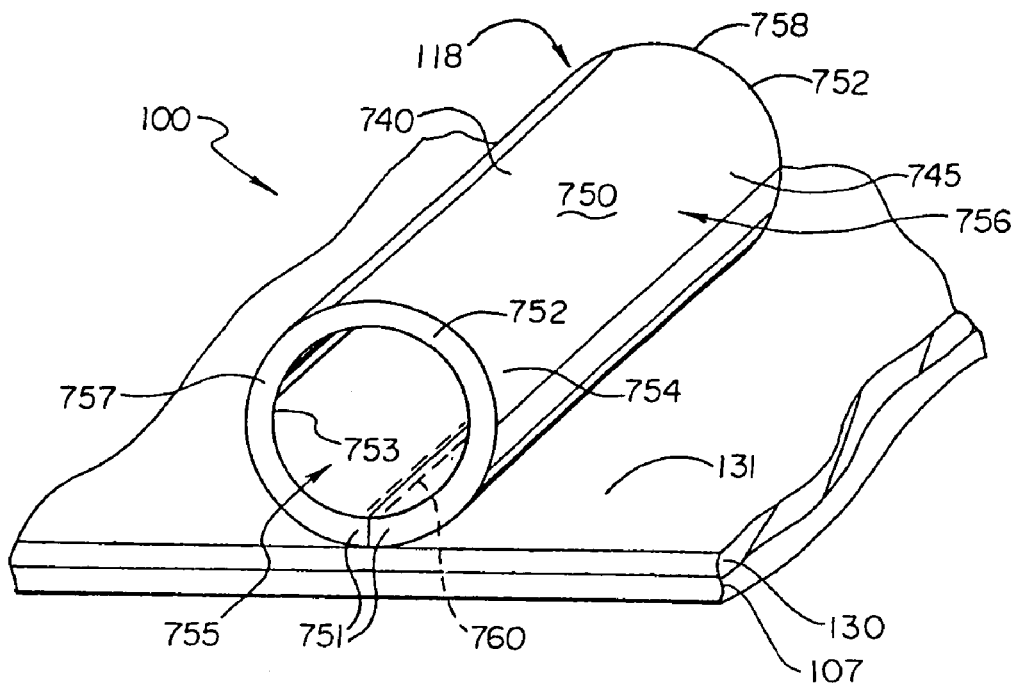
FIG. 31 is a perspective view of an embodiment of a lead electrode assembly in which the appendage is a cylindrical tube.

FIG. 31 illustrates an alternative embodiment of the lead electrode assembly 100. This embodiment is substantially similar to the embodiment illustrated in FIGS. 30(*a*)-30(*d*). The backing layer 130 of this embodiment, however, lacks a fin head 700 and flexible joining material 702.

Moreover, the appendage 118 in this embodiment comprises a tube 740 having an interior 755, an exterior 756, a proximal end 757 and a distal end 758. The tube comprises a sheet of material 750. The sheet of material 750 is substantially rectangular having a first pair of sides 751, a second pair of sides 752, a first surface 753 and a second surface 754.

The sheet of material 750 is folded so that its first pair of sides 751 abuts each other. The folded sheet of material 750 forms a tube 740. The first surface 753 of the sheet of material 750 faces the interior 755 of the tube 740. The second surface 754 of the sheet of material 750 faces the exterior of the tube 756. In folding the sheet of material 750 so that the first pair of sides 751 abuts each other, the second pair of sides 752 of the sheet of material 750 is folded in a circular shape to form the proximal end 757 and distal end 758 of the tube 740. This results in the tube 740 having a cylindrical shape. The diameter of the circular proximal end 757 and distal end 758 of the tube 756 is approximately 5 mm. In alternate embodiments, the diameter range between approximately 1 mm and approximately 10 mm. The length of the tube 756 as measured between the proximal end 757 and distal end 758 of the tube 756 is approximately 1 cm. In alternate embodiments, length of the tube 756 ranges between approximately 2 mm and approximately 6 cm. In one embodiment, the tube 756 is substantially as long as the electrode 107.

The second surface 754 of the sheet of material 750 is attached to the first surface 131 of the backing layer 130. The first pair of sides 751 of the sheet of material 750 is attached to the backing layer 130 with stitching 760.

In alternate embodiments, the proximal end 757 of the tube 740 is closed. In one embodiment, the proximal end 757 of the tube 740 is closed by a cap (not shown). In another embodiment, the proximal end 757 of the tube 740 is closed by holding one of the second pair of sides 752 of the sheet of material 750 closed with stitching. In another embodiment, the proximal end 757 of the tube 740 is closed by any other means known in the art for this purpose.

It should be noted that the appendage 118 in some alternative embodiments comprises a tube with a shape other than a cylinder. An example of a tube with a shape other than cylindrical is illustrated below in FIG. 32.

Figure 32:
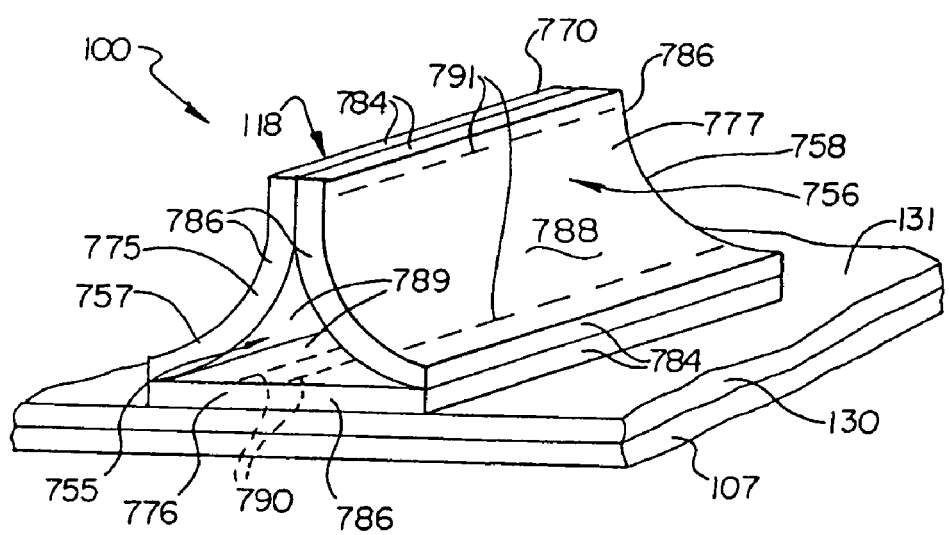
FIG. 32 is a perspective view of an embodiment of a lead electrode assembly in which the appendage is a tube with a substantially triangular cross section.
Figure 33A:
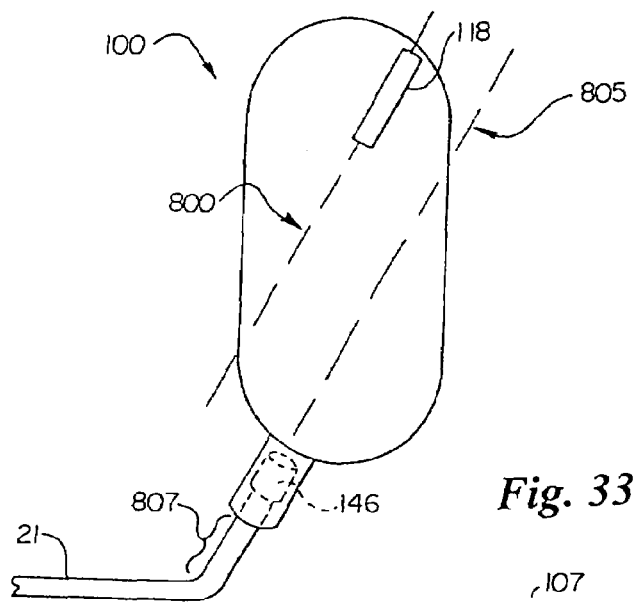
FIGS. 33(a)-(d) are top plan views of embodiments of lead electrode assemblies illustrating shapes of the electrode and the lines of the lead.
Figure 33B:
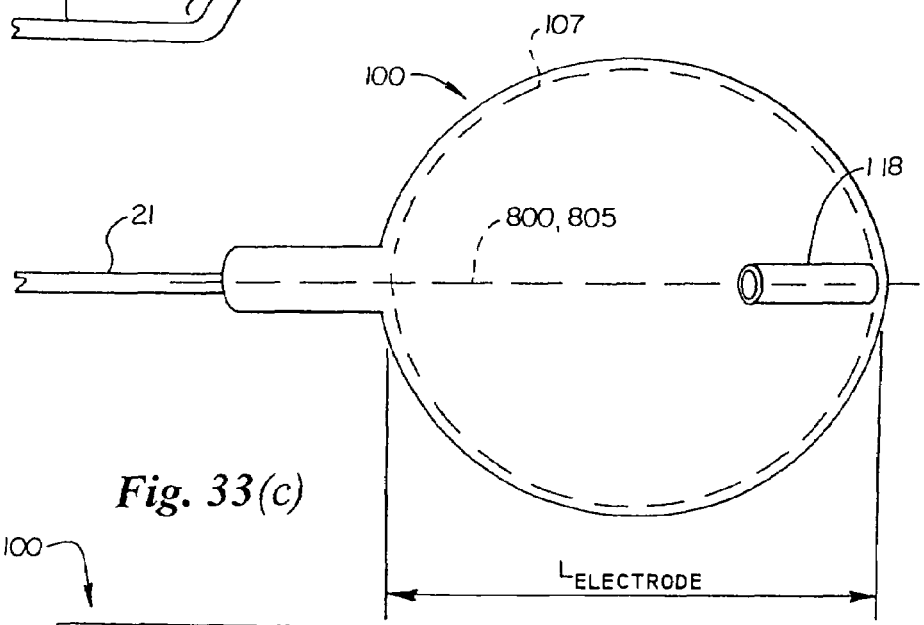
Figure 33C:
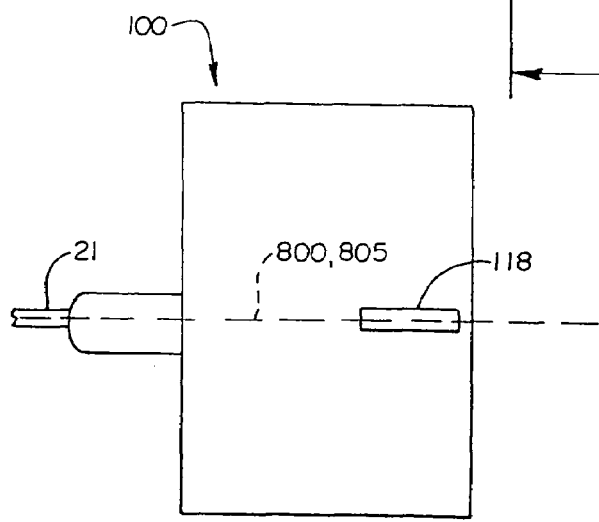
Figure 33D:
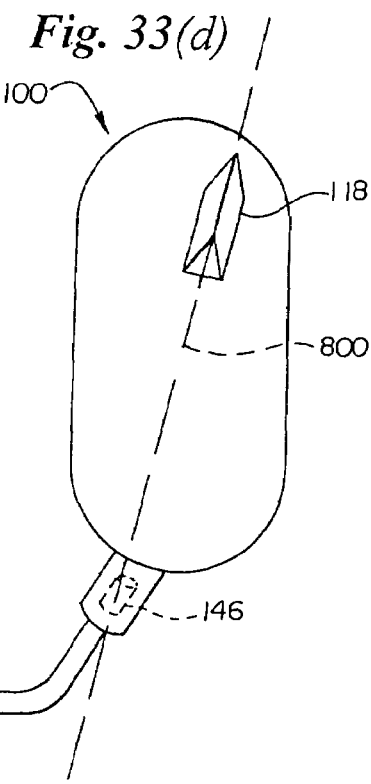
Figure 33E:
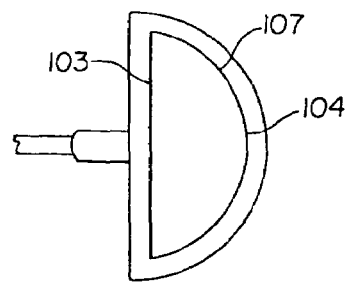
FIGS. 33(e)-(h) are bottom plan views of embodiments of lead electrode assemblies illustrating shapes of the electrode.
Figure 33F:
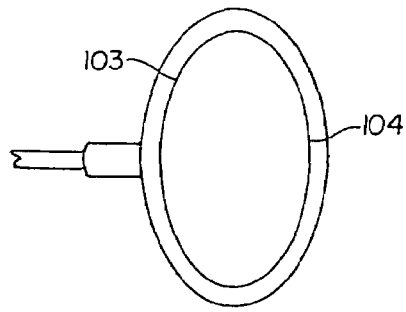
Figure 33G:
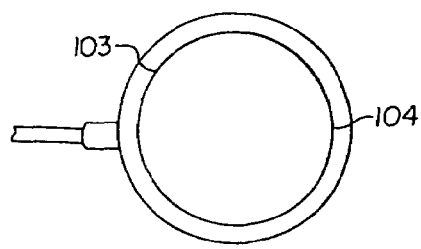
Figure 33H:
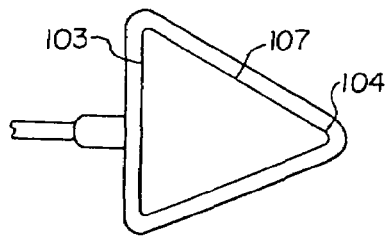

FIG. 32 illustrates an alternative embodiment of the lead electrode assembly 100. This embodiment is substantially similar to the embodiment illustrated in FIG. 31. The tube 740 comprising a sheet of material 750, however, is absent from this embodiment.

Moreover, the appendage 118 of this embodiment comprises a tube 770 having an interior 755 an exterior 756, a proximal end 757 and a distal end 758. The tube comprises a first sheet of material 775, a second sheet of material 776 and a third sheet of material 777. The first sheet of material 775, the second sheet of material 776 and the third sheet of material 777 are all substantially rectangular in shape. Each comprises a first pair of sides 784, a second pair of sides 786, a first surface 788 and a second surface 789. The first pair of sides 784 of each sheet of material is parallel to each other. In another embodiment, the first pair of sides 784 of each sheet of material is non-parallel. The second pair of sides 786 of each sheet of material is parallel to each other. In another embodiment, the second pair of sides 786 of each sheet of material is non-parallel.

The first pairs of sides 784 of each sheet of material are attached to the first pair of sides 784 of the other sheets of material. In this way the second pair of sides 786 of the first sheet of material 775, the second sheet of material 776 and the third sheet of material 777 form a triangular shaped proximal end 757 and distal end 758 of the tube 770. The sheets of material are attached to each other such that the second surface 789 of each sheet of material faces the interior 755 of the tube 770. The sheets of material are attached to each other with stitching 791.

The height of the tube 770 is approximately 5 mm. In alternate embodiments, the height ranges between approximately 1 mm and approximately 10 mm. The length of the tube 770 as measured between the proximal end 757 and distal end 758 of the tube 770 is approximately 1 cm. In alternate embodiments, length of the tube 770 ranges between approximately 2 mm and approximately 6 cm. In one embodiment, the tube 770 is substantially as long as the electrode 107.

The second sheet of material 776 is attached to the backing layer 130 with stitching 790. The first surface 788 of the second sheet of material 776 is positioned next to the first surface 131 of the backing layer 130.

In alternate embodiments, some or all of the sheets of material are reinforced with a layer of Dacron® polymer mesh. In one embodiment, the Dacron® polymer mesh is attached to the first surface 788 of each sheet of material. In another embodiment, the Dacron® polymer mesh is attached to the second surface 789 of each sheet of material. In another embodiment, the sheets of material are similarly reinforced with a layer of any polymeric material.

In alternate embodiments, the proximal end 757 of the tube 770 is closed. In one embodiment, the proximal end 757 of the tube 770 is closed by a cap. In another embodiment, the proximal end 757 of the tube 770 is closed by holding the sides 786 of the first sheet of material 775, the second sheet of material 776 and the third sheet of material 777 that form the proximal end 757 of the tube 770 together with stitching. In another embodiment, the proximal end 757 of the tube 770 is closed by any other means known in the art for this purpose.

FIGS. 33(*a*)-33(*d*) illustrate various possible positions for the appendage 118 relative to the lead 21 of the lead electrode assembly 100. Additionally, up to this point, all embodiments of the electrode 107 illustrated and discussed have had a rectangular shape. These figures illustrate alternative embodiments with electrodes 107 of different shapes.

At this point, it is useful to set out two definitions in order to discuss the possible orientation of appendages 118.

The interface line is defined as the center line of the appendage 118 as traced on the electrode 107. FIG. 33(*a*) illustrates the interface line 800 of the appendage 118 of a lead electrode assembly 100.

The line of the lead is defined as the line along which the lead 21 of the lead electrode assembly 100 enters the lead fastener 146. The line of the lead 805 of line 21 is shown as it enters the lead fastener 146 (in phantom). As the lead 21 approaches the lead fastener 146, the closest section 807 of the lead 21 forms the line of the lead. When the lead 21 is not bent, the entire lead 21 lies along the line of the lead.

FIG. 33(*b*) illustrates an embodiment wherein the lead 21 is not bent and the entire lead 21 lies along the line of the lead 805.

The electrode length, $L_{Electrode}$, is the length of the electrode 107 as measured along the interface line 800.

In the embodiments of the lead electrode assembly 100 shown in FIGS. 33(*b*) and 33(*c*), the interface line 800 is the same line as the line of the lead 805. In the embodiment shown in FIG. 33(*a*) the interface line 800 is parallel with the line of the lead 805.

In the embodiment of the lead electrode assembly 100 shown in FIG. 33(*d*), the interface line 800 intersects the lead fastener 146 (phantom view).

FIGS. 33(*e*)-33(*h*) show various additional electrode shapes disposed in various lead electrode assemblies 100. The electrode shapes are not limited, however, to the shapes specifically illustrated.

The electrode 204 depicted in FIG. 33(*e*) has a "thumbnail" shape. The proximal end 104 of this electrode 107 is generally rounded. As the electrode 107 moves distally along its length, the conductive surface terminates at the distal end 103 of the electrode 107.

An ellipsoidal shaped electrode 107 is depicted in FIG. 33(*f*). The proximal end 104 of the ellipsoidal shaped electrode 107 is generally rounded. As the ellipsoidal shaped electrode 107 moves distally along its length, the conductive surface terminates in a rounded distal end 103.

A circular shaped electrode 107 is illustrated in FIG. 33(*g*).

A triangular shaped electrode 107 is depicted in FIG. 33(*h*). Triangular shaped electrodes 107 also incorporate electrodes that are substantially triangular in shape. In particular to FIG. 33(h), the corners of the triangular shaped electrode 107 are rounded.

Several lead electrode assembly manipulation tools 927 have been developed to manipulate the lead electrode assemblies during their surgical implantation.

FIG. 34 illustrates an embodiment of a lead electrode assembly manipulation tool 927. The lead electrode assembly manipulation tool 927 comprises an enhanced hemostat 930 used to manipulate lead electrode assemblies 100 comprising an eyelet during their implantation in patients.

The enhanced hemostat 930 comprises the following components: a hemostat having a first prong 931, a second prong 932, a hinge 939 and an eyelet pin 940. The first prong 931 is attached to the second prong 932 by the hinge 939. The eyelet pin is attached to the second prong 932.

The first prong 931 comprises a first end 933 and a second end 934. The second prong 932 comprises a first end 935 and a second end 936. The first prong and second prong are approximately 75 cm long and curved with a radius of approximately 30 cm. In alternate embodiments, the curvature of the hemostat does not have a radius of approximately 30 cm, but instead approximates the curvature of the thorax of a patient. In one embodiment, the curvature of the hemostat approximates the curvature of the thorax of a patient along a subcutaneous path taken from the anterior axillary line, posteriorly toward the spine.

The first prong 931 is pivotally attached to the second prong 932 by the hinge 939. The hinge is attached to the first prong 931 approximately 10 cm from the first end 933. In this embodiment, the hinge is attached to the second prong 932 approximately 10 cm from the second end 935.

The eyelet pin 940 can be inserted through the eyelet 301 of a fin 120 of the lead electrode assembly 100 such as the lead electrode assembly 100 discussed with reference to FIGS. 22(a)-22(g) as a means of capturing the lead electrode assembly 100 prior to its implantation in a patient.

The eyelet pin 940 is a cylindrical member having a first end 941 and a second end 942. In an alternate embodiment, the eyelet pin 940 is a hook-shaped member. The diameter of the cylinder is approximately 2 mm. In alternate embodiments, the diameter of the cylinder ranges from approximately 1 mm to approximately 5 mm. The length of the eyelet pin 940 is approximately 8 mm. In alternate embodiments, the length of the eyelet pin 940 ranges from approximately 4 to approximately 15 mm.

The first end of the eyelet pin 940 is attached to the second prong 932, approximately 8 mm from the second end 936 of the second prong 932. In alternate embodiments, the eyelet pin 940 is attached to the second prong 932 at various lengths from the second end 936 of the second prong 932.

The eyelet pin 940 is attached to the second prong 932 in an orientation perpendicular to the length of the second prong 932. The eyelet pin 940 is attached to the second prong 932 so that it extends away from the second end 934 of the first prong 931.

In this embodiment, all of the components are made of stainless steel. In an alternative embodiment, some or all of the components are composed metals other than stainless steel or are composed of a polymeric material.

We now turn to a discussion of the positions of the components that comprise an entire S-ICD system including the lead electrode assembly 100 when it is implanted in a patient.

FIGS. 35(a) and 35(b) illustrate an embodiment of the S-ICD system implanted in a patient as a means of providing cardioversion/defibrillation energy.

FIG. 35(a) is a perspective view of a patient's ribcage with an implanted S-ICD system. The S-ICD canister 11 is implanted subcutaneously in the anterior thorax outside the ribcage 1031 of the patient, left of the sternum 920 in the area over the fifth rib 1038 and sixth rib 1036. The S-ICD canister 11, however, may alternately be implanted anywhere over the area between the third rib and the twelfth rib. The lead 21 of the lead electrode assembly 100 is physically connected to the S-ICD canister 11 where the transthoracic cardiac pacing energy or effective cardioversion/defibrillation shock energy (effective energy) is generated. The term "effective energy" as used in this specification can encompass various terms such as field strength, current density and voltage gradient.

The lead 21 of the lead electrode assembly 100 travels from the S-ICD canister 11 to the electrode 107, which is implanted subcutaneously in the posterior thorax outside the ribcage 1031 of the patient in the area over the eighth rib 1030 and ninth rib 1034. The electrode 107, may alternately be implanted subcutaneously anywhere in the posterior thorax outside the ribcage 1031 of the patient in the area over the third rib 1030 and the twelfth rib 1034. The bottom surface 115 of the electrode 107 faces the ribcage. The electrode or active surface 15 (phantom view) of the canister 11 also faces the ribcage.

FIG. 35(b) is a cross-sectional side plan view of the patient's rib cage. Here it is seen that the lead 21 travels around the circumference of the thorax, in the subcutaneous layer beneath the fat 1050 between the outside of the ribcage 1031 and the skin 1055 covering the thorax.

We now turn to a discussion of a method by which the lead electrode assembly 100 of the S-ICD system is implanted in a patient using a standard hemostat as well as the enhanced hemostat described above. FIG. 36 and FIGS. 37(a)-37(d) illustrate aspects of this method.

Figure 36:
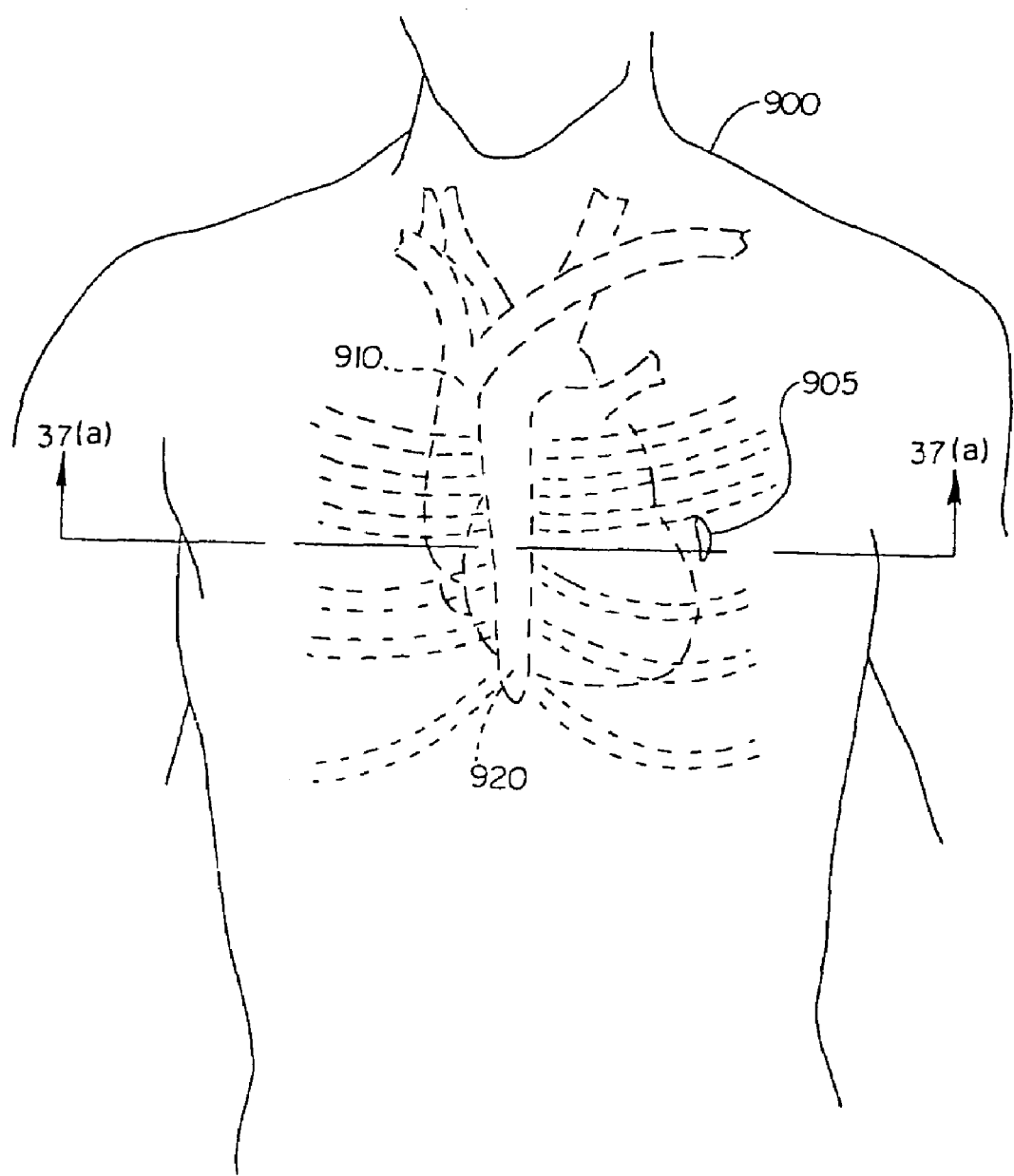
FIG. 36 is a front plan view illustrating the incision point for the surgery to implant the lead electrode assembly.

In operation, as seen in FIG. 36, an incision 905 is made in the patient 900 in the anterior thorax between the patient's third and fifth rib, left of the sternum 920. The incision can alternately be made in any location between the patient's third and twelfth rib. The incision can be made vertically (as shown), horizontally or angulated. In order to minimize scarring, the incision can be made along Langher's lines.

Figure 37A:
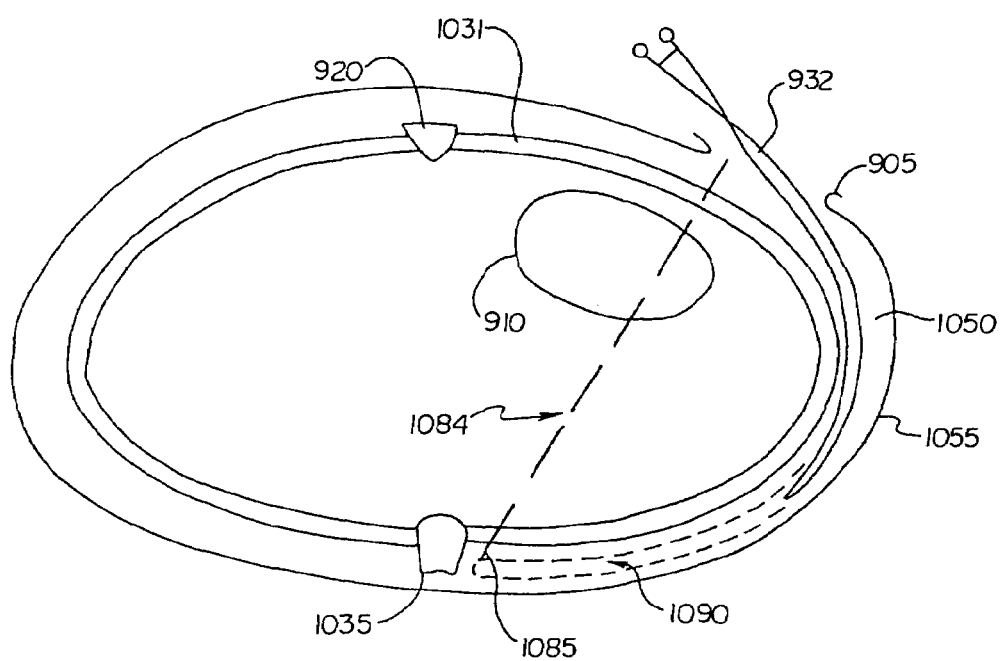
FIG. 37(a) is a cross-sectional bottom plan view of a patient along line 37(a) of FIG. 36 illustrating the creation of a subcutaneous path for implantation of the lead electrode assembly of an S-ICD system.

FIG. 37(a) shows a bottom view cross-section of the patient 900, along the line 37(a) shown in FIG. 36. A hemostat 930, with prongs 932 is introduced into the incision 905. The hemostat 930 is inserted with its prongs together without anything gripped between them. The prongs 932 of the hemostat 930 are pushed through the fat 1050 between the skin 1055 of the thorax and the ribcage 1031 to create a subcutaneous path 1090. The prongs 932 of the hemostat 930 can alternately be pushed beneath the fat 1050 that lies between the skin 1055 of the thorax and the ribcage 1031 to create a subcutaneous path 1090 between the fat 1050 and the ribcage 1031.

The hemostat is moved around the ribcage 1031 until the subcutaneous path 1090 reaches within approximately 10 cm of the spine 1035 between the eighth rib 1030 and ninth rib 1034 (this location is best seen in FIG. 35(a)) between the skin 1055 and the ribcage 1031. The subcutaneous path 1090 can alternately be made to reach any location between the skin 1055 and the ribcage 1031 between the patient's third and twelfth rib. The hemostat 930 is then withdrawn. Alternately, the hemostat 930 can be moved around the ribcage 1031 until the subcutaneous path 1090 terminates at a termination point 1085 at which a line 1084 drawn from the termination point 1085 to the incision 905 would intersect the heart 910.

Figure 37B:
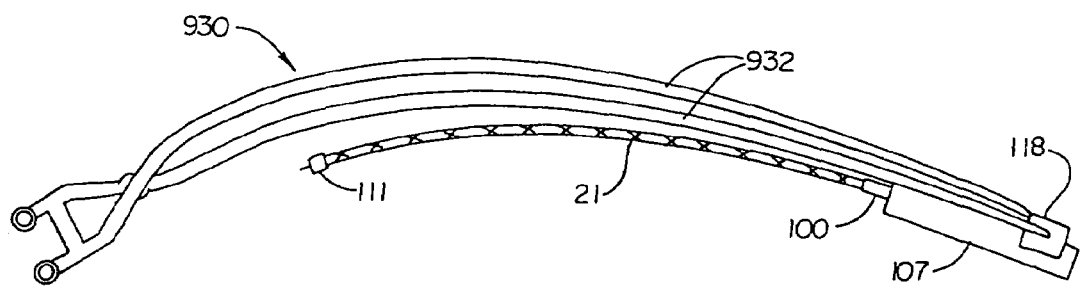
FIG. 37(b) is a perspective view of a lead electrode assembly captured by a custom hemostat.

Next, as shown in FIG. 37(b), the appendage 118 of a lead electrode assembly 100 is squeezed between the tongs 932 of a hemostat 930.

Figure 37C:
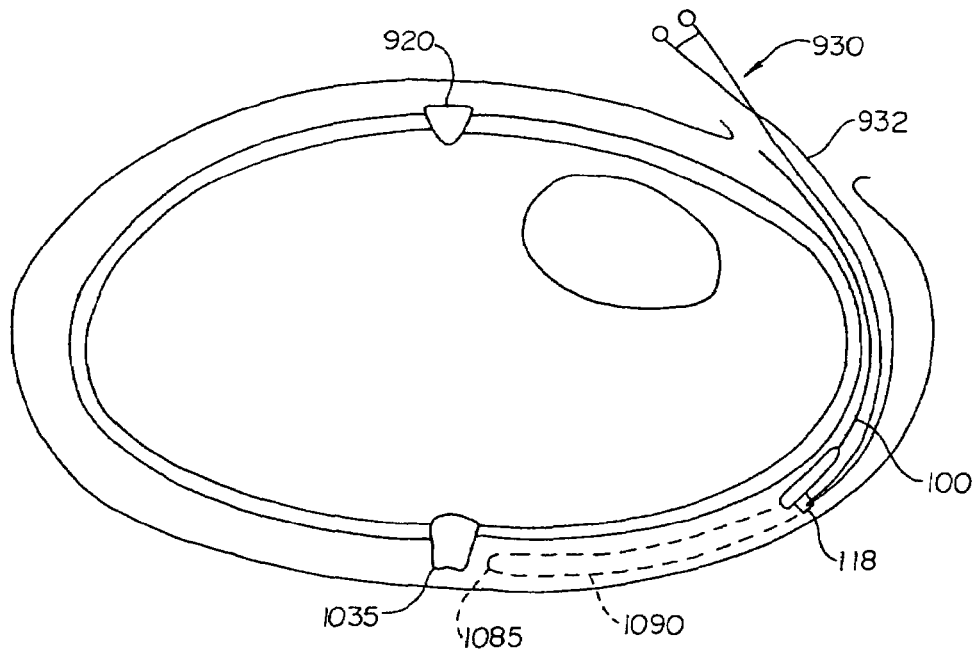
FIG. 37(c) is a cross-sectional bottom plan view of a patient along line 37(a) of FIG. 36 illustrating the implantation of a lead electrode assembly via the subcutaneous path.

As shown in FIG. 37(c), the lead electrode assembly 100 and hemostat tongs 932 are introduced to the subcutaneous path 1090 and pushed through the subcutaneous path until the lead electrode assembly 100 reaches the termination point 1085 of the path. The appendage 118 of the lead electrode assembly 100 is then released from the tongs 932 of the hemostat 930. The hemostat 930 is then withdrawn from the subcutaneous path 1090.

Figure 37D:
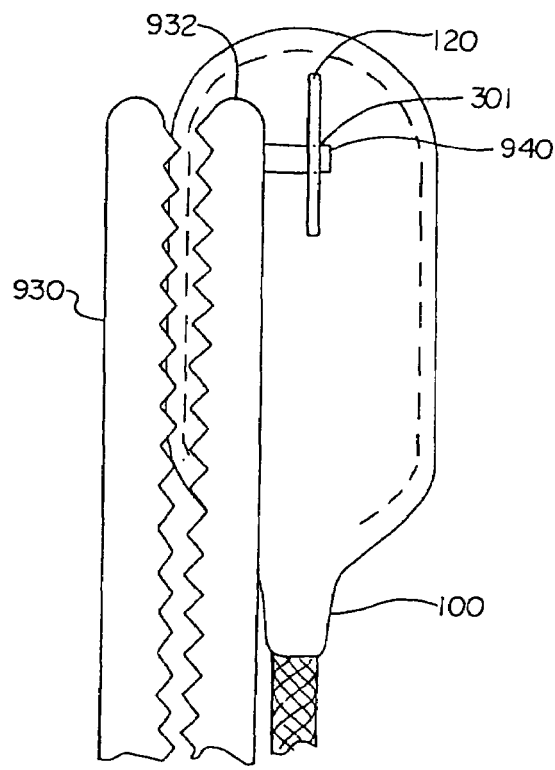
FIG. 37(d) is a top view of a lead electrode assembly captured by a custom hemostat.

In an alternative method, the enhanced hemostat 930 seen in FIG. 34 is used to introduce the lead electrode assembly 100 into the subcutaneous path 1090 created as discussed above. After the subcutaneous path 1090 is created, the lead electrode assembly 100 is attached to the enhanced hemostat 930 as shown in FIG. 37(d). Eyelet pin 1108 is inserted through the eyelet 301 in the fin 120 of the lead electrode assembly 100. The enhanced hemostat 930 is then used to introduce the lead electrode assembly 100 into the subcutaneous path 1090, as shown in FIG. 37(c). The lead electrode assembly 100 is then moved through the subcutaneous path 1090 until the electrode 107 reaches the end of the path 1085. The enhanced hemostat 930 is then moved until the lead electrode assembly 100 is released from the eyelet pin 940. The enhanced hemostat 930 is then withdrawn from the subcutaneous path 1090.

Figure 38A:
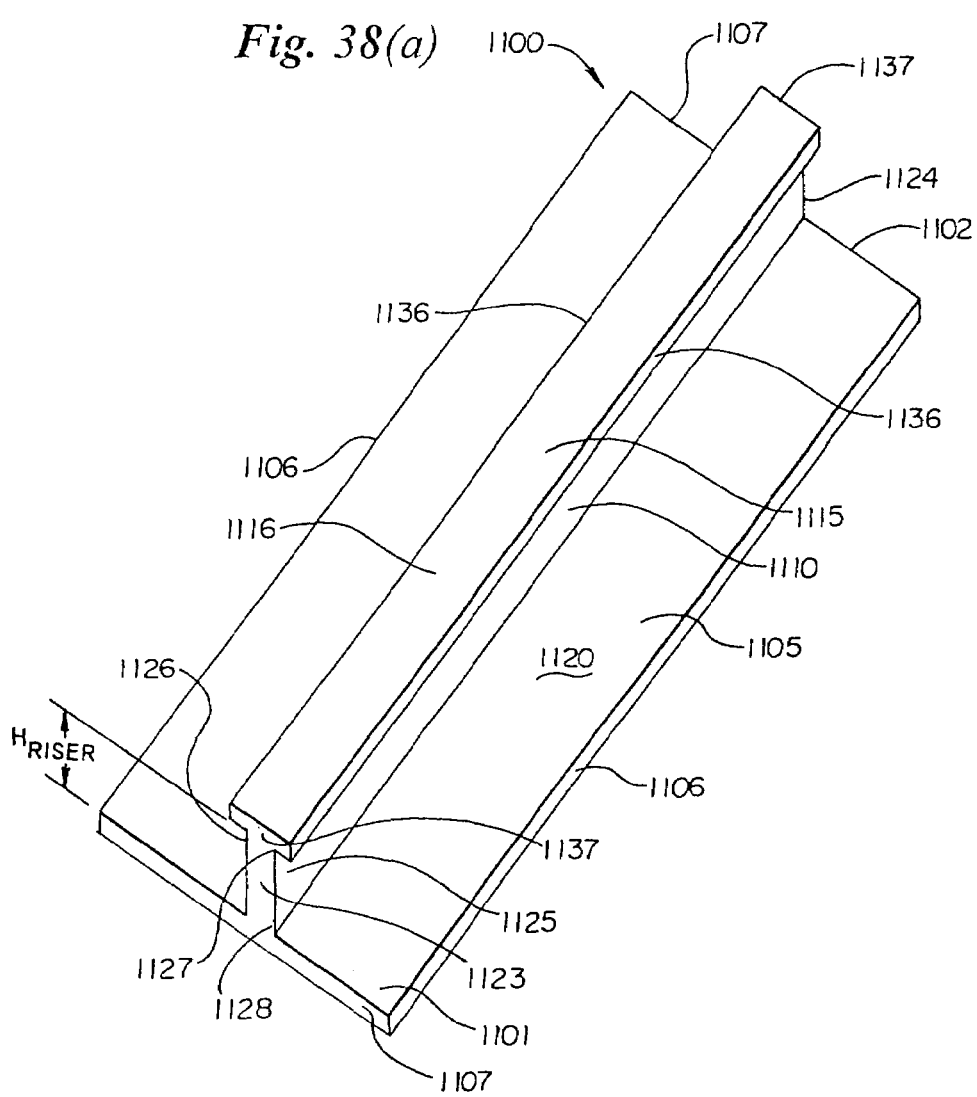
FIG. 38(a) is a perspective view of a rail of an embodiment of the lead electrode assembly.
Figure 38B:
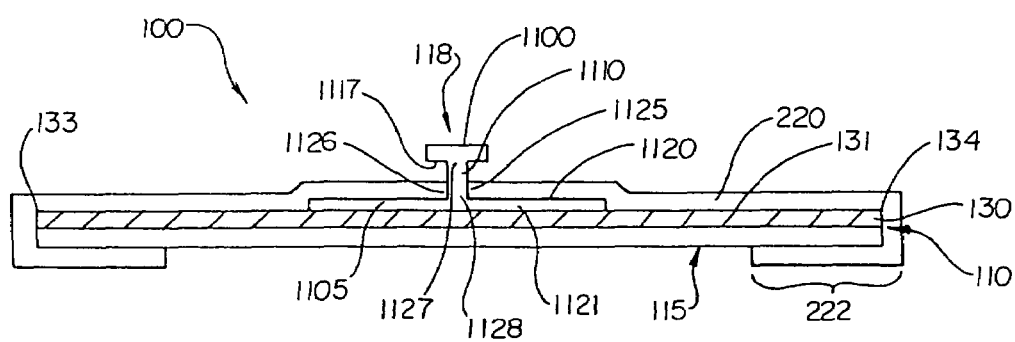
FIG. 38(b) is a cross-sectional front plan view of an embodiment of the lead electrode assembly where the appendage is a rail.
Figure 38C:
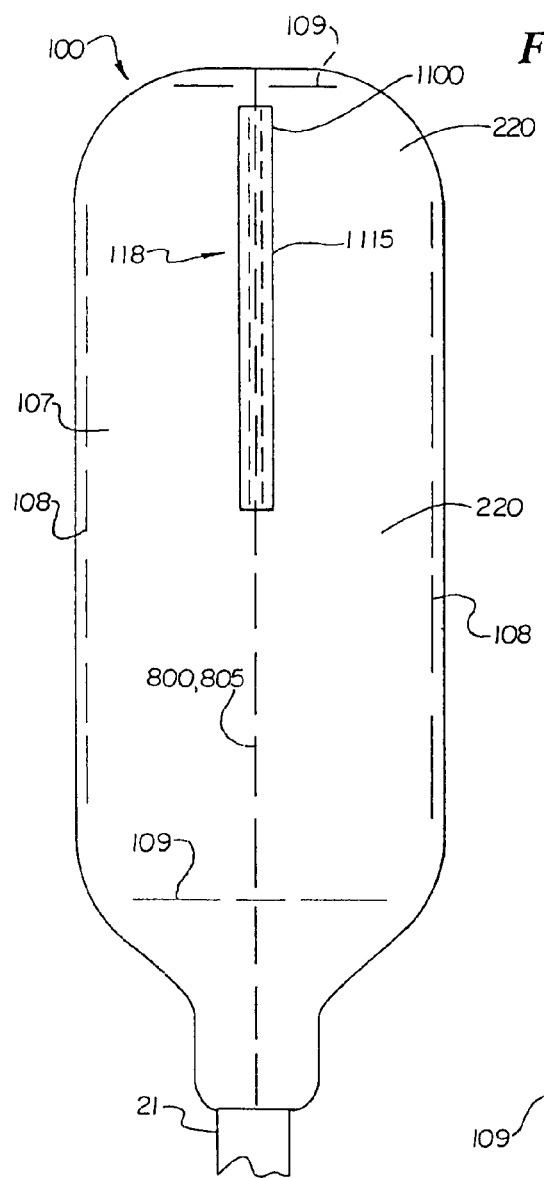
FIG. 38(c) is a top plan view of an embodiment of the lead electrode assembly where the appendage is a rail.

FIGS. 38(a)-38(c) illustrate an alternative embodiment of the lead electrode assembly 100. This embodiment is substantially similar to the embodiments illustrated in FIGS. 22(a)-22(g). The backing layer 130 of this embodiment, however, lacks an integrated fin tab 180. Moreover, the appendage 118 of the lead electrode assembly 100 of this embodiment comprises a rail 1100.

FIG. 38(a) illustrates the rail 1100 of the lead electrode assembly 100 of this embodiment. The rail 1100 is a member attached to the electrode 107 that can be captured by a lead electrode assembly manipulation tool and used to precisely locate the electrode 107 during its surgical implantation within the patient. The rail 1100 comprises three sections: a foundation 1105, a riser 1110 and a head 1115. The foundation 1105 is separated from the head 1115 by the riser 1125.

The foundation 1105 comprises a flat, substantially planar member, comprising a first pair of sides 1106 and a second pair of sides 1107. The first pair of sides 1106 of the foundation 1105 is substantially linear and substantially parallel. In an alternate embodiment, the first pair of sides 1106 of the foundation 1105 is neither linear nor parallel. The length of the first pair of sides 1106 of the foundation 1105 is approximately 2 cm. In alternate embodiments, the length of the first pair of sides 1106 of the foundation 1105 ranges from approximately 2 mm to approximately 6 cm. In an alternate embodiment, the first pair of sides 1106 of the foundation 1105 is as long as the electrode 107 (not shown) of the lead electrode assembly 100 (not shown).

The second pair of sides 1107 of the foundation 1105 is substantially linear and substantially parallel. In an alternate embodiment, the second pair of sides 1107 of the foundation 1105 is neither linear nor parallel. The length of the second pair of sides 1107 of the foundation 1105 is approximately 1 cm. In alternate embodiments, the length of the second pair of sides 1107 of the foundation 1105 ranges from approximately 0.5 cm to approximately 3 cm.

The foundation 1105 further comprises a top surface 1120 and a bottom surface 1121. The foundation 1105 has a thickness, measured as the distance between the top surface 1120 and the bottom surface 1121. The thickness of the foundation 1105 is 2 mm. In alternate embodiments, the thickness of the foundation 1105 ranges between approximately 1 mm and approximately 5 mm.

Turning now to the riser 1110, the riser 1110 comprises a flat, substantially planar protrusion from the top surface 1120 of the foundation 1105 of the rail 1100. The riser comprises a first face 1125, a second face 1126, a top 1127, a bottom 1128, a proximal end 1123 and a distal end 1124. The first face 1125 and second face 1126 are parallel to each other and perpendicular to the top surface 1120 of the foundation 1105. The first face 1125 and a second face 1126 of the riser 1110 are parallel to the first pair of sides 1106 of the foundation 1105. The bottom 1128 of the riser 1110 joins the foundation 1105 in a position centered between the first pair of sides 1106 of the foundation 1105. The proximal end 1123 of the riser 1110 and the distal end 1124 of the riser 1110 are parallel to each other and perpendicular to the top surface 1120 of the foundation 1105. In other embodiments, the proximal end 1123 of the riser 1110 and the distal end 1124 of the riser 1110 are not parallel to each other.

In one embodiment, the proximal end 1123 of the riser 1110 is not perpendicular the top surface 1120 of the foundation 1105. Instead, the proximal end 1123 of the riser 1110 is sloped, so that the proximal end 1123 and the distal end 1124 of the riser 1110 are closer at the top 1127 of the riser 1110 than at the bottom 1128 of the riser. A slanted proximal end 1123 make the rail 1100 of the lead electrode assembly 100 offer less resistance against the tissues of the patient during insertion into the patient.

The height of the riser, $H_{Riser}$, is measured as the distance between the top surface 1120 of the foundation 1105 to the head 1115, perpendicular to the top surface 1120 of the foundation 1105. The height of the riser is approximately 5 mm. In alternate embodiments, the height of the riser ranges from approximately 1 mm to approximately 10 mm.

The riser 1110 has a width, measured as the distance between the first face 1125 and the second face 1126. The width of the riser 1110 is 2 mm. In alternate embodiments, the width of the riser 1110 ranges from approximately 1 mm to approximately 6 mm.

Turning now to the head 1115, the head 1115 is a flat, substantially planar member. The head 1115 comprises a first pair of sides 1136, a second pair of sides 1137, a top surface 1116 and a bottom surface 1117 (not shown). The first pair of sides 1136 and the second pair of sides 1137 of the head 1115 are substantially linear and substantially parallel. In an alternate embodiment, the first pair of sides 1136 of the head 1115 is neither linear nor parallel. In an alternate embodiment, the second pair of sides 1137 of the head 1115 is neither linear nor parallel.

The length of the first pair of sides 1136 of the head 1115 is equal to the length of the first pair of sides 1106 of the foundation 1105. In alternate embodiments, the length of the first pair of sides 1136 of the head 1115 is unequal to the length of the first pair of sides 1106 of the foundation 1105. The length of the second pair of sides 1137 of the head 1115 is approximately 5 mm. In alternate embodiments, the length of the second pair of sides 1137 of the head 1115 ranges from approximately 3 mm to approximately 10 mm.

The bottom surface 1117 of the head 1115 joins the top 1127 of the riser 1110 opposite the foundation 1105 of the rail 1100. The top surface 1116 and the bottom surface 1117 of the head 1115 are parallel to the top surface 1120 of the foundation 1105. In an alternate embodiment, the top surface 1116 and the bottom surface 1117 of the head 1115 are not parallel to the top surface 1120 of the foundation 1105.

The head 1115 has a thickness, measured as the distance between the top surface 1116 and the bottom surface 1117 of the head 1115. The thickness of the head 1115 is approximately 2 mm. In alternate embodiments, the thickness of the head ranges between approximately 2 mm and approximately 10 mm.

The foundation 1105, the head 1115 and the riser 1110 are made of stainless steel. In alternate embodiments, some or all of the sections of the rail 1100 are made of metals other than stainless steel. In alternate embodiments, some or all of the sections of the rail 1100 are made of a polymeric material wherein the polymeric material is selected from the group consisting essentially of a polyurethane, a polyamide, a polyetheretherketone (PEEK), a polyether block amide (PEBA), a polytctrafluoroethylene (PTFE), a silicone and mixtures thereof.

The foundation 1105, the head 1115 and the riser 1110 are machined from the same piece of material. In an alternate embodiment, some or all of the sections are formed independently and welded to the others.

Turning in detail to FIG. 38(b), the position of the rail 1100 within the lead electrode assembly 100 will be discussed. The rail 1100 is positioned so that its bottom surface 1121 is adjacent to and covers a region of the first surface 131 of the backing layer 130. The rail is centered between the first side 133 and second side 134 of the backing layer 130. In an alternate embodiment, the rail is not centered between the first side 133 and second side 134 of the backing layer 130.

In an alternate embodiment, there is no backing layer 130 and the rail 1100 is positioned so that its bottom surface 1121 is adjacent to the top surface 110 of the electrode 107.

Turning now to the electrode 107 of this embodiment, the electrode 107 is the same shape and size as the electrode 107 discussed with reference to FIGS. 22(a)-22(g). In alternative embodiments, the length of the first pair of sides 108 (not shown) and second pair of sides 109 (not shown) of the electrode 107 ranges independently between approximately 1 cm and approximately 5 cm.

Turning now to the molded cover 220, the skirt 222 of the molded cover 220 partially covers the bottom surface 115 of the electrode 107 as discussed with reference to FIG. 22(d). The molded cover 220 further substantially covers the first surface 131 of the backing layer 130. The molded cover 220 does not cover the first surface 131 of the backing layer 220 in the region in which the bottom surface 1121 of the rail 1100 is adjacent to the backing layer 130. Instead, the molded cover 220 in this region substantially covers the top surface 1120 of the rail 1100. The molded cover 220 abuts the first face 1125 and second face 1126 of the riser 1110 of the rail 1100.

Turning to FIG. 38(c), the position of the lead 21 and the appendage 118 will now be discussed. The interface line 800 of the appendage 118 and the line of the lead 805 are the same line. In an alternate embodiment, interface line 800 of the appendage 118 and the line of the lead 805 are not the same line. The line of the lead 805 is centered between the first pair of sides 108 (phantom view) of the electrode 107 (phantom view). In an alternate embodiment, the line of the lead 805 is not centered between the first pair of sides 108 of the electrode 107.

Figure 39:
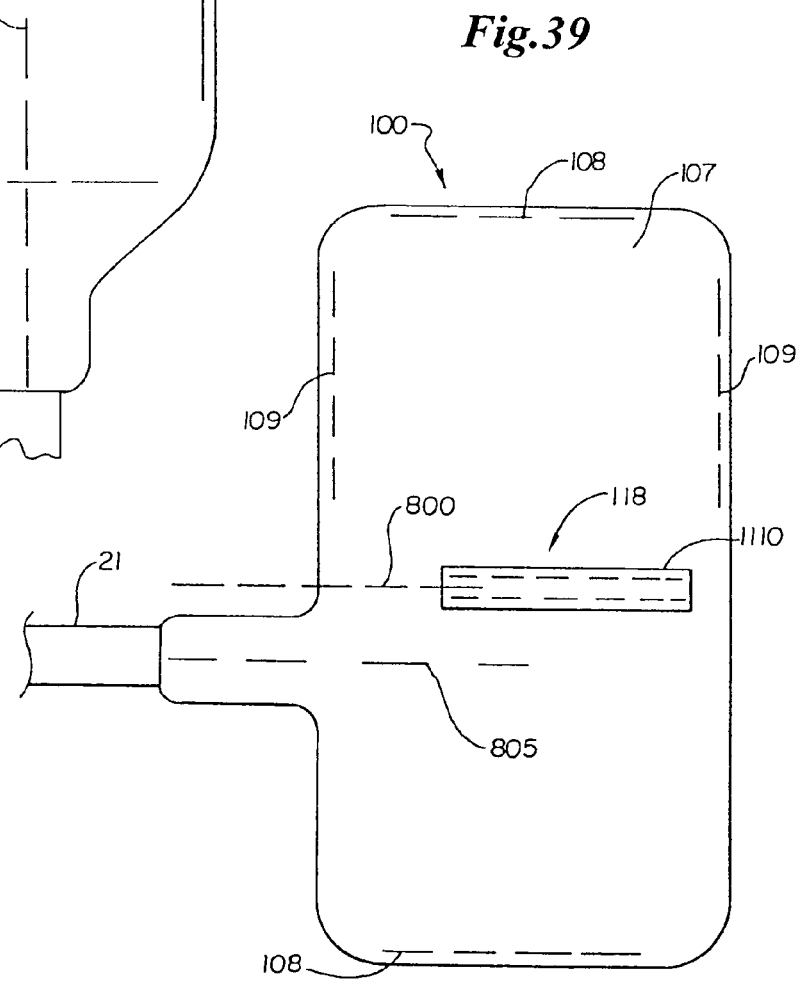
FIG. 39 is a top view of an embodiment of the lead electrode assembly where the appendage is a rail.

FIG. 39 illustrates an alternative embodiment of the lead electrode assembly 100. This embodiment is substantially similar to the embodiment illustrated in FIGS. 38(a)-38(c). In this embodiment, however, the dimensions of the electrode 107 are different from those of the embodiment illustrated in FIGS. 38(a)-38(c).

The first pair of sides 108 of the electrode 107 (phantom view) is approximately 2.4 cm in length. The second pair of sides 109 of the electrode 107 is approximately 4 cm in length. In alternative embodiments, the length of the first pair of sides 108 and second pair of sides 109 of the electrode 107 ranges independently between approximately 1 cm and approximately 5 cm.

The interface line 800 of the rail 1100 is parallel to the line of the lead 805. In an alternate embodiment, the interface line 800 of the rail 1110 is not parallel to the line of the lead 805. The interface line 800 of the rail 1100 is centered between the first pair of sides 108 of the electrode 107. In an alternate embodiment, the interface line 800 of the rail 1100 is not centered between the first pair of sides 108 of the electrode 107.

The line of the lead 805 is not centered between the first pair of sides 108 of the electrode 107. Because the lead 805 is not centered between the first pair of sides 108 of the electrode 107, the lead rail 1110 may be more easily accessed by a lead electrode manipulation tool (not shown). In an alternate embodiment, the line of the lead 805 is centered between the first pair of sides 108 of the electrode 107.

FIG. 40 illustrates a lead electrode assembly manipulation tool 927 useful for manipulating a lead electrode assembly (not shown) having an appendage 118 comprising a rail 1100 during the implantation of the lead electrode assembly 100 in a patient. Examples of such lead electrode assembly 100 embodiments are shown in FIGS. 38(a)-38(c) and 39.

The lead electrode assembly manipulation tool 927 comprises a handle 1142, a rod 1144 and a rail fork 1146. The handle 1142 is connected to the rod 1144. The rail fork 1146 is also connected to the rod 1144.

The rod 1144 is a cylindrical member with a diameter of approximately 4 mm, approximately 25 cm in length, having a proximal end 1147 and a distal end 1148. The rod 1144 is curved with a radius of approximately 20 cm.

The rod is made of steel. In other embodiments, the rod is composed of titanium, a polymeric material or any other material suitable for this purpose.

The handle 1142 is a cylindrical member with a diameter sized to fit comfortably in the palm of a surgeon's hand. The rod is connected to the proximal end 1147 of the rod 1144. In an alternate embodiment, the handle 1142 is not cylindrical. In an alternate embodiment, the handle 1142 has ergodynamic contours.

The handle is made of polyurethane. In an alternate embodiment, the handle is made of any metal, or any polymeric material suitable for this purpose.

Figure 40A:
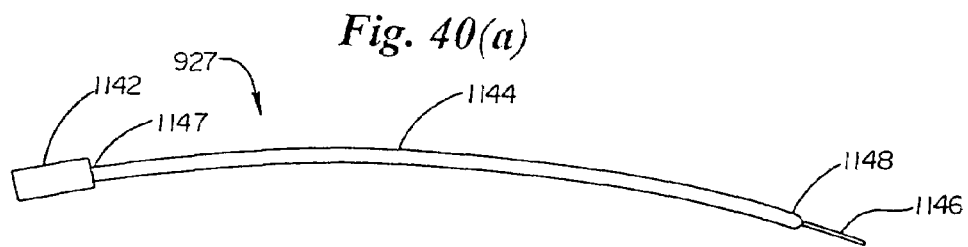
FIG. 40(a) is a perspective view of a lead electrode assembly manipulation tool with a rail fork.
Figure 40B:
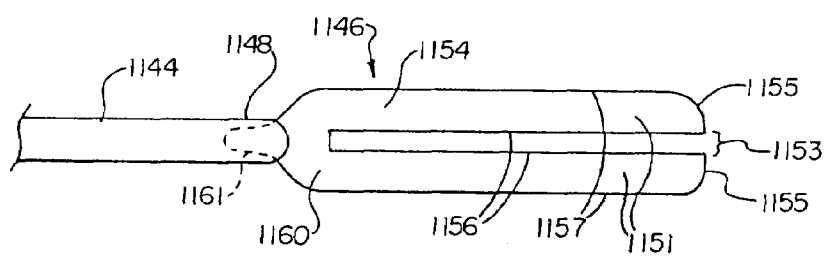
FIG. 40(b) is a top plan view of a lead electrode assembly manipulation tool with a rail fork.

Turning now to FIG. 40(b), the rail fork 1146 is attached to the distal end 1148 of the rod 1144. The rod further comprises a slot 1162 in its distal end. The rail fork comprises a pair of tines 1151 separated by a gap 1153 and a tine base 1160 having a tang 1161.

Each of the pair of tines 1151 has a proximal end 1154 and a distal end 1155. The proximal ends 1154 of the pair of tines 1151 are attached to the tine base 1160. Each of the pair of tines 1151 has a substantially rectangular form with straight inner sides 1156 and straight outer sides 1157. The distal ends 1155 of each of the pair of tines 1151 are rounded. The length of the pair of tines 1151, measured from the distal end 1155 to the proximal end 1154, is substantially equal to the length of the first pair of sides 1106 of the rail 1100 of the lead electrode assembly 100. In alternate embodiments, the length of the pair of tines 1151 is substantially greater than or less than the length of the first pair of sides 1106 of the rail 1100.

The pair of tines 1151 is separated by a gap 1153 formed by the inner sides 1156 of the pair of tines 1151 and the tine base 1160.

The pair of tines 1151 and the tine base 1160 comprising the rail fork 1146 are punched from a single sheet of steel having a thickness of approximately 3 mm. In other embodiments, the rail fork 1146 is composed of titanium, a polymeric material or any other material suitable for this purpose. In one embodiment, the handle 1142, the rod 1144 and the rail fork 1146 are all made from the same piece of material.

Figure 40C:
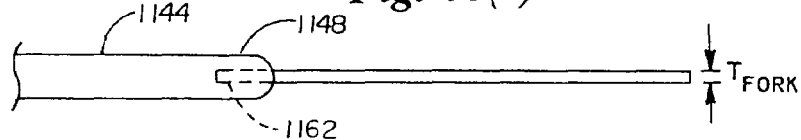
FIG. 40(c) is a side plan view of a lead electrode assembly manipulation tool with a rail fork.

FIG. 40(c) illustrates a side plan view of the lead electrode assembly manipulation tool 927. The rod 1144 further comprises a slot 1162 in its distal end 1148. The tine base 1160 connects the pair of tines 1151 to the distal end 1148 of the rod 1144. The tine base 1160 comprises a tang 1161 (phantom view). The tang 1161 is inserted in the slot 1162 in the rod 1144. The tang 1161 is welded in the slot 1162 of the rod 1144.

We now turn to a description of the use of the lead electrode assembly manipulation tool 927 in the implantation of a lead electrode assembly 100 into a patient.

As discussed with reference to FIG. 36, an incision 905 is made in the patient 900. As discussed with reference to FIG. 37(a), a subcutaneous path 1090 is created in the patient 900 with a hemostat 932.

Figure 40D:
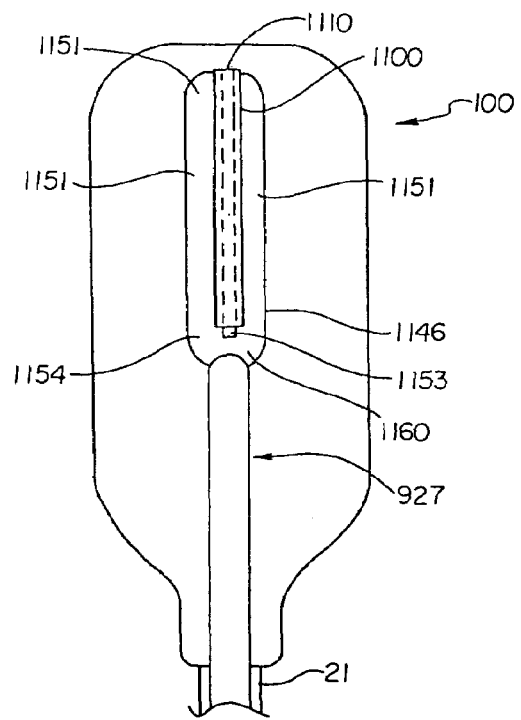
FIG. 40(d) is a top plan view of a lead electrode assembly having a rail captured by a lead electrode assembly manipulation tool with a rail fork.

As shown in FIG. 40(d), the lead electrode assembly 100 is then captured by the lead electrode assembly manipulation tool 927. The rail 1110 of the lead electrode assembly 100 is inserted into the rail fork 1146 of the lead electrode assembly manipulation tool 927. The riser 1110 (phantom view) of the rail is placed into the gap 1153 between the pair of tines 1151 of the rail fork 1146. The pair of tines 1151 fits between the bottom surface 1117 of the head 1115 of the rail 1100 and the molded cover 220. The rail 1100 is slid toward the proximal end 1155 of the pair of tines 1151 until the riser 1110 of the rail 1100 reaches the tine base 1160 of the rail fork 1146. The lead 21 of the lead electrode assembly 100 can then be pulled in toward the handle 1142 of the lead electrode assembly manipulation tool 927 until it is taut. This acts to prevent the rail 1100 of the lead electrode assembly 100 from sliding toward the distal end 1151 of the pair of tines 1151 of the rail fork 1146.

As discussed with reference to FIG. 37(c), the lead electrode assembly manipulation tool 927 may then be used to place the lead electrode assembly 100 into the incision 905 of the patient 900 and used to move the electrode 107 to the termination point 1085 of the subcutaneous path 1090.

The lead electrode assembly 100 is then released from the lead electrode assembly manipulation tool 927. To achieve this, the lead 21 of the lead electrode assembly 100 is released so that the pair of tines 1151 of the rail fork 1146 of the lead electrode assembly manipulation tool 927 can slide relative to the rail 1100 of the lead electrode assembly 100. The lead electrode assembly manipulation tool 927 may then be extracted from the subcutaneous path 1090, leaving the lead electrode assembly 100 behind.

Figure 41A:
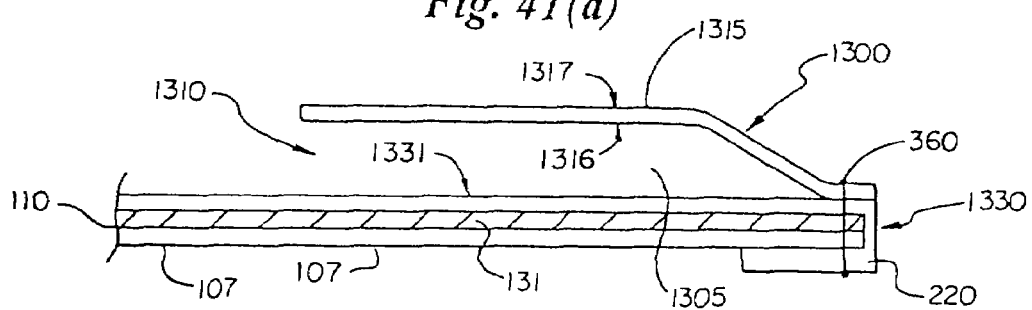
FIG. 41(a) is a cross-sectional side plan view of a lead electrode assembly with a pocket.
Figure 41B:
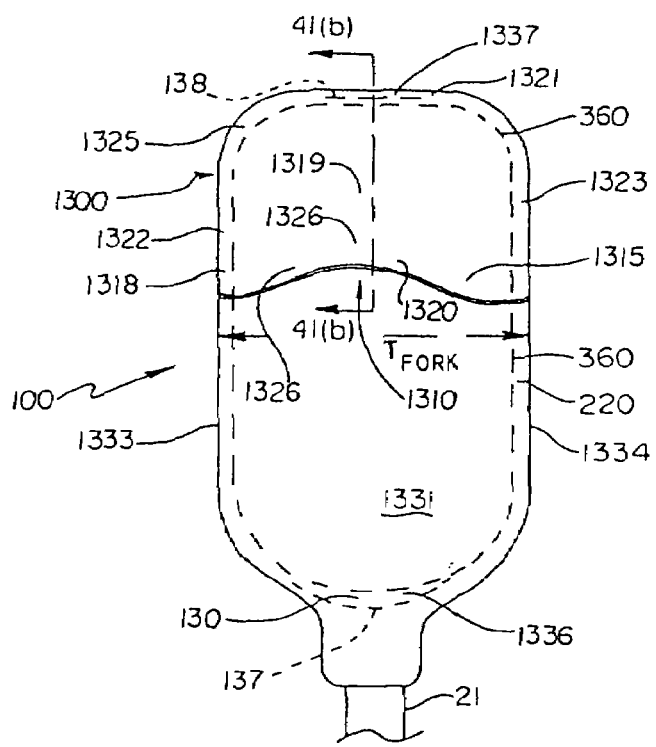
FIG. 41(b) is a top plan view of a lead electrode assembly with a pocket.

FIGS. 41(a)-41(b) illustrate an alternative embodiment of the lead electrode assembly 100. This embodiment is substantially similar to the embodiments illustrated in FIGS. 22(a)-22(g). The backing layer 130 of this embodiment, however, lacks an integrated fin tab 180. Moreover, the lead electrode assembly 100 of this embodiment further comprises a pocket 1300.

FIG. 41(a) illustrates a cross-sectional side plan view of this embodiment. The pocket 1300 comprises a layer of material 1315 and stitching 360. The pocket further comprises an interior 1305 and an opening 1310. The layer of material 1315 is attached to the molded cover 220 with the stitching 360. The molded cover 220 is, in turn, attached to the electrode 107.

The molded cover 220 comprises an outer surface 1330 and a top surface 1331. The outer surface 1330 of the molded cover 220 is the surface of the molded cover 220 that does not lie adjacent to the backing layer 131 or the electrode 107. The top surface 1331 of the molded cover 220 faces away from, and parallel to the electrode 107.

The layer of material 1315 of the pocket 1300 comprises an inner face 1316 and an outer face 1317. The layer of material 1315 is attached to the top surface 1331 of the molded cover 220 so that the inner face 1316 of the layer of material 1315 faces the top surface 1331 of the molded cover 220. The inner face 1316 of the layer of material 1315 also faces the top surface 110 of the electrode 107.

The layer of material 1315 is made of polyurethane. In other embodiments, the layer of material 1315 is made of any bio-compatible material suitable for this purpose. In other embodiments, the layer of material 1315 is made of any bio-compatible polymeric material.

The stitching 360 fastening the layer of material 1315 to the top surface 1331 of the molded cover 220 is comprised of nylon. In alternate embodiments, the stitching 360 comprises any polymeric material.

FIG. 41(b) illustrates a top plan view of the lead electrode assembly 100 of FIG. 41(a). The top surface 1331 of the molded cover 220 has a first side 1333, a second side 1334, a distal end 1336, a proximal end 1337, a length and a width.

The distal end 1336, proximal end 1337, first side 1333 and second side 1334 of the top surface 1331 of the molded cover 220 are positioned substantially over the distal end 137 (phantom view), proximal end 138 (phantom view), first side 133 (not shown) and second side 134 (not shown) of the backing layer 130 (phantom view) respectively.

The width of the top surface 1331 of the molded cover 220 is measured as the distance between the first side 1333 and second side 1334 of the back surface. The length of the top surface 1331 of the molded cover is measured as the distance between the distal end 1336 and proximal end 1337 of the molded cover 220.

The layer of material 1315 comprises a periphery 1318 and a middle portion 1319. More particularly, the layer of material 1315 comprises a distal end 1320, a proximal end 1321, a first side 1322 and a second side 1323. The periphery 1318 of the layer of material 1315 comprises the distal end 1320, the proximal end 1321, the first side 1322 and the second side 1323 of the layer of material 1315. The middle portion 1319 of the layer of material 1315 comprises the area between the distal end 1320, the proximal end 1321, the first side 1322 and the second side 1323 of the layer of material 1315.

The pocket 1300 formed by the layer of material 1315 further comprises a bounded region 1325 and a center 1326. The bounded region 1325 of the pocket 1300 is attached to the back face 1317 of the molded cover 220. The center 1326 of the pocket 1300 is not attached to the back face 1317 of the molded cover 220. Stitching 360 in the bounded region 1325 is used to attach the layer of material 1315 to the molded cover 220.

In the embodiment under discussion, the bounded region 1325 of the pocket 1300 comprises a portion of the periphery 1318 of the layer of material 1315. The bounded region 1325 of the pocket 1300 comprises the proximal end 1321, the first side 1322 and the second side 1323 of the layer of material 1315. In this embodiment, the bounded region 1325 of the pocket 1300 does not comprise the distal end 1320 of the layer of material 1315. The center 1326 of the pocket 1300 comprises the middle portion 1319 of the layer of material 1315. The bounded region 1325 is curved around the center 1326 of the pocket 1300 in a "U" shape. The bounded region 1325 of the pocket 1300 does not completely enclose the center 1326 of the pocket 1300.

In this embodiment, the bounded region 1325 of the pocket comprises a contiguous portion of the periphery 1318 of the layer of material 1315. In an alternate embodiment, the bounded region 1325 of the pocket comprises a plurality of segmented portions of the periphery 1318 of the layer of material 1315.

In an alternate embodiment the bounded region 1325 of the pocket 1300 does not comprise any portion of the periphery 1318 of the layer of material 1315. In alternate embodiments, the bounded region 1325 comprises any shape that could be traced on the layer of material 1315 that partially encloses a center 1326. In one embodiment, the bounded region 1325 of the pocket 1300 is a portion of a circle's circumference (not shown) that does not touch the periphery 1318 of the layer of material 1315. The center 1326 is the area inside the circle.

In an alternate embodiment, the pocket 1300 comprises a sheet of molded silicone. The molded silicone is fused to the molded cover 220 in the bounded region 1325.

The opening 1310 of the pocket 1300 comprises the area between the distal end 1320 of the layer of material 1315 and the top surface 1331 of the molded cover 220. The interior 1305 of the pocket 1300 comprises the area between the middle portion 1319 of the layer of material 1315 and the top surface 1331 of the molded cover 220.

The layer of material 1315 is positioned so that its first side 1322 and second side 1323 are positioned over the first side 1333 and second side 1334 of the top surface 1331 of the molded cover 220 respectively. The layer of material 1315 is positioned so that its proximal end 1321 is positioned over the proximal end 1337 of the top surface 1331 of the molded cover 220.

The layer of material 1315 is sized so that its length is shorter than the length of the top surface 1331 of the molded cover 220. In alternate embodiments, the layer of material 1315 is sized so that its length is equal to, or longer than the length of the top surface 1331 of the molded cover 220.

The proximal end 1321 of the layer of material 1315 is sized so that its width is substantially equal to the width of the proximal end 1337 of the top surface 1331 of the molded cover 220. The layer of material 1315 is sized so that its width steadily increases toward its distal end 1320.

The first side 1318 of the distal end 1320 of the layer of material 1315 is fastened to the first side 1333 of the top surface 1331 of the molded cover 220. The second side 1323 of the distal end 1320 of the layer of material 1315 is fastened to the second side 1334 of the top surface 1331 of the molded cover 220.

Since the first end 1322 of the layer of material 1315 is wider than the top surface 1331 of the molded cover 220, the layer of material 1315 separates from the top surface 1331 of the molded cover 220 to form the interior 1305 of the pocket 1300.

In an alternate embodiment, the lead electrode assembly 100 lacks a molded cover 220 and the pocket 1300 is attached directly to the backing layer 130. In another alternate embodiment the lead electrode assembly 100 lacks a molded cover 220 and a backing layer 130 and the pocket 1300 is attached directly to the electrode 107. In a further alternate embodiment, the pocket 1300 is molded as part of the molded cover 220.

Figure 41C:
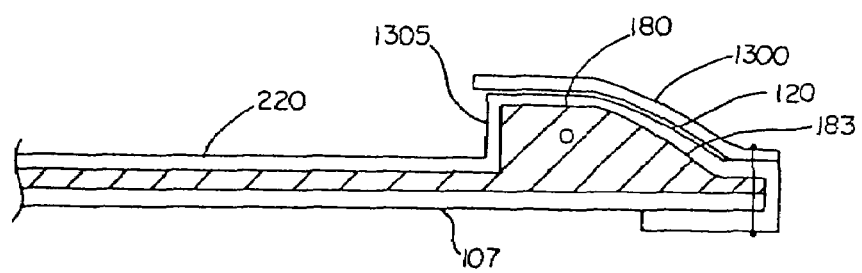
FIG. 41(c) is a cross-sectional side plan view of a lead electrode assembly with a pocket and a fin.

FIG. 41(c) illustrates a cross-sectional side plan view of an alternative embodiment of the lead electrode assembly 100. This embodiment is substantially similar to the embodiment illustrated in FIGS. 41(a)-41(b). The backing layer 130 of this embodiment, however, further comprises a fin 120 positioned in the interior 1305 of the pocket 1300. The fin 120 of this embodiment is substantially similar to the fin 120 of the embodiment illustrated in FIG. 22(b).

The fin 120 comprises an integrated fin tab 180 formed on the backing layer 130. The molded cover 220 covers the integrated fin tab 180 to form the fin 120. The integrated fin tab 180 has a slope-shaped proximal edge 183. The sloped shape of the resulting fin 120 permits the fin 120 to fit deeply into the interior 1305 of the pocket 1300. The hood can act to reduce the resistance presented by the tissues of the patient against the fin 120 and any tool used to grasp the fin 120 during insertion of the lead electrode assembly 100. Such a hood can be placed over any fin discussed in the specification to perform this function or any other function.

In alternate embodiments, appendages other than a fin are positioned between the pocket 1300 and the electrode 107, in the interior 1305 of the pocket 1300. In one embodiment, a loop such as that discussed with reference to FIGS. 26(a)-26(c) is positioned in the interior 1305 of the pocket 1300. In another embodiment, a tube such as that discussed with reference to FIG. 31 is positioned in the interior 1305 of the pocket 1300.

Figure 42A:
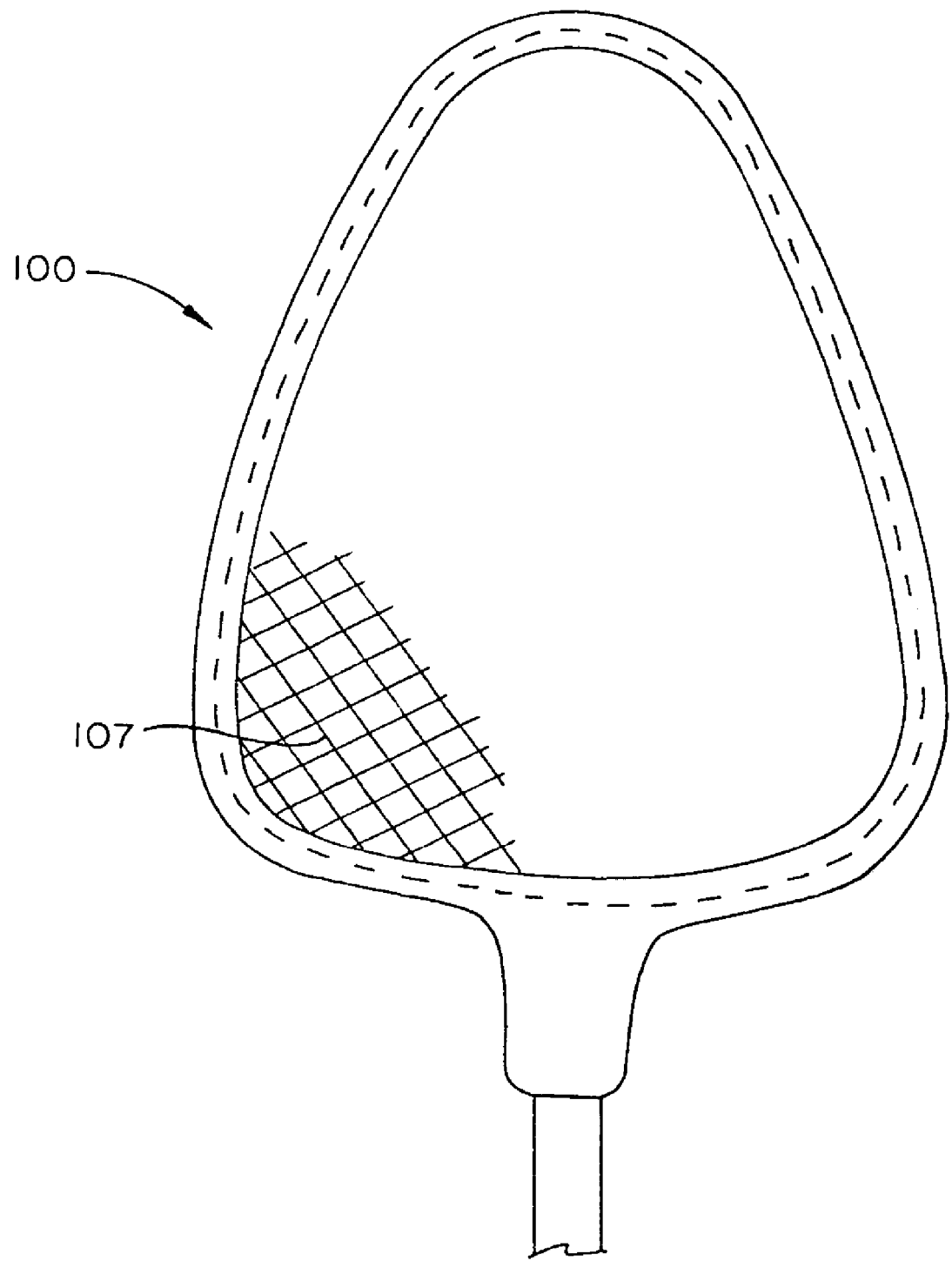
FIG. 42(a) is a bottom plan view of a lead electrode assembly with a pocket.
Figure 42B:
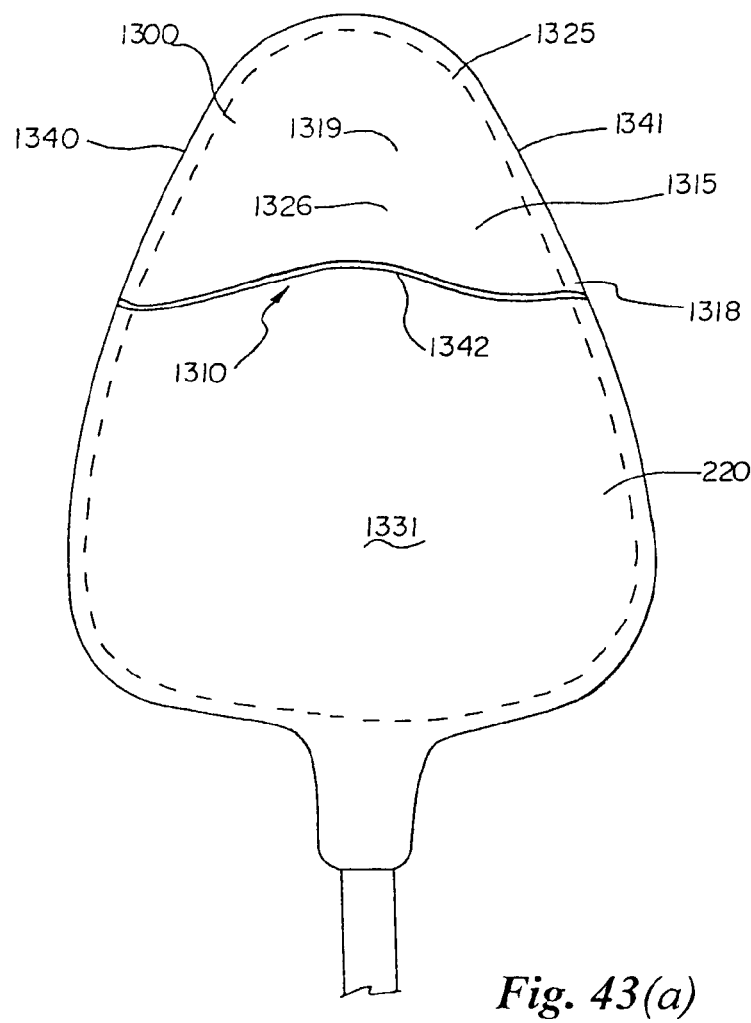
FIG. 42(b) is a top plan view of a lead electrode assembly with a pocket.

FIGS. 42(a) and 42(b) illustrates an alternate embodiment of the lead electrode assembly 100. This embodiment is substantially similar to the embodiment illustrated in FIGS. 41(a)-41(b).

FIG. 42(a) illustrates a bottom plan view of the lead electrode assembly 100 of this embodiment. In this embodiment, the electrode 107 is thumbnail shaped.

FIG. 42(b) illustrates a top plan view of the lead electrode assembly 100 of this embodiment. The top surface 1331 of the molded cover 220 is shaped to accommodate the thumbnail shaped electrode 107.

Like the embodiment discussed with reference to FIGS. 41(a)-41(b), the pocket 1300 comprises a layer of material 1315. In this embodiment, however, the layer of material 1315 has a roughly triangular shape. The layer of material 1315 comprises a periphery 1318 and a middle portion 1319. More particularly, the layer of material comprises a first side 1340, a second side 1341 and a third side 1342 of the layer of material 1315. The periphery 1318 of the layer of material comprises the first side 1340, the second side 1341 and the third side 1342 of the layer of material 1315. The middle portion 1319 of the layer of material 1315 comprises the area between the first side 1340, the second side 1341 and the third side 1342 of the layer of material 1315.

In this embodiment, the bounded region 1325 of the pocket 1300 comprises a portion of the periphery 1318 of the layer of material 1315. The bounded region 1325 of the pocket 1300 comprises the first side 1340 and the second side 1341 of the layer of material 1315. The center 1326 of the pocket 1300 comprises the middle portion 1319 of the layer of material 1315. The opening 1310 of the pocket 1300 comprises the third side 1342 of the layer of material 1315 and the top surface 1331 of the molded cover 220. The bounded region 1325 of the pocket 1300 is curved around the center 1326 of the pocket 1300. The bounded region 1325 of the pocket 1300 does not completely enclose the center 1326.

In this embodiment, the bounded region 1325 of the pocket comprises a contiguous portion of the periphery 1318 of the layer of material 1315. In an alternate embodiment, the bounded region 1325 of the pocket comprises a plurality of segmented portions of the periphery 1318 of the layer of material 1315.

In an alternate embodiment the bounded region 1325 of the pocket 1300 does not comprise any portion of the periphery 1318 of the layer of material 1315.

Figure 43A:
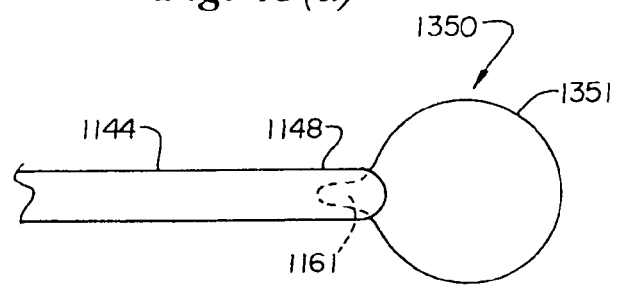
FIG. 43(a) is a top plan view of a lead electrode assembly manipulation tool with a paddle.
Figure 43B:
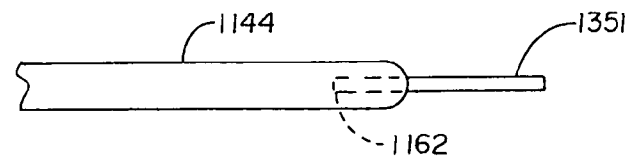
FIG. 43(b) is a side plan view of a lead electrode assembly manipulation tool with a paddle.
Figure 43C:
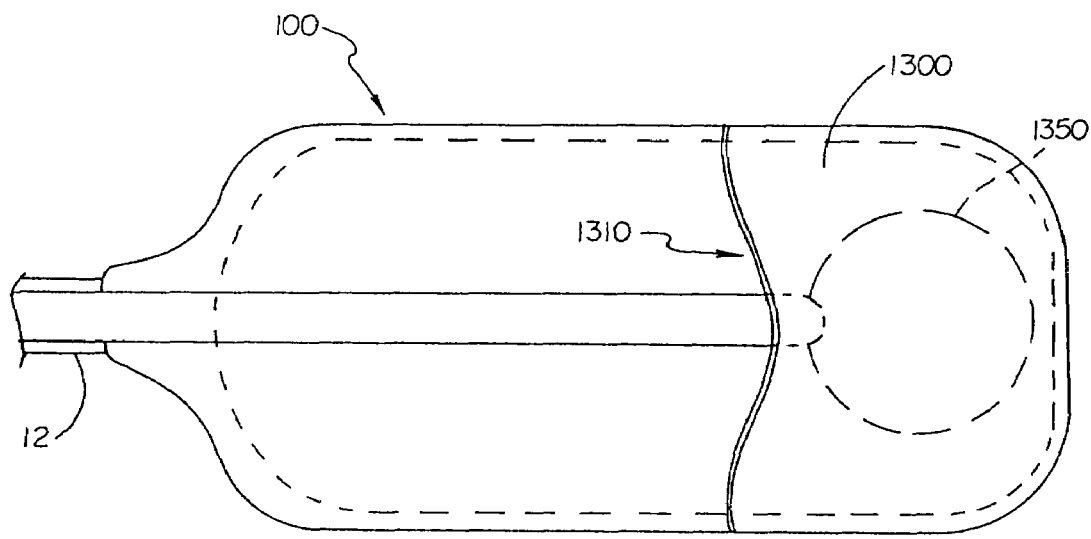
FIG. 43(c) is a top plan view of a lead electrode assembly with a pocket captured by a lead electrode assembly manipulation tool with a paddle.

FIG. 43(*a*)-43(*c*) illustrates a lead electrode assembly manipulation tool 927. The lead electrode assembly manipulation tool 927 illustrated is useful for manipulating a lead electrode assembly 100 having a pocket 1300 during the implantation of the lead electrode assembly 100 in a patient. Examples of such a lead electrode assembly 100 embodiments are shown in FIGS. 41(*a*), 41(*b*), 42(*a*) and 42(*b*).

FIG. 43(*a*) is a top view of the lead electrode assembly manipulation tool 927 of this embodiment. The lead electrode assembly manipulation tool 927 comprises a handle 1142 (not shown), a rod 1144 and a paddle 1350.

The rod 1144 and handle 1142 are substantially similar to the rod 1144 and handle 1142 of the lead electrode assembly manipulation tool 927 illustrated in FIGS. 40(*a*)-40(*d*). The handle 1142 is connected to the rod 1144.

The paddle 1350 is attached to the distal end 1148 of the rod 1144. The paddle 1350 comprises a disk 1351 and a tang 1161 (phantom view).

FIG. 43(*b*) is a side view of the lead electrode assembly manipulation tool 927 of this embodiment. The tang 1161 is inserted in the slot 1162 in the rod 1144. The tang 1161 is welded into the slot 1162 of the rod 1144.

The disk 1351 and the tang 1161 are punched from a single sheet of steel having a thickness of approximately 3 mm. In other embodiments, the disk 1351 and tang 1161 are composed of titanium, a polymeric material or any other material suitable for this purpose. In one embodiment, the handle 1142, the rod 1144 and the paddle 1350 are all made from the same piece of material.

We now turn to FIG. 43(*c*) for a description of the use of the lead electrode assembly manipulation tool 927 in the implantation of a lead electrode assembly 100 into a patient.

As discussed with reference to FIG. 36, an incision 905 is made in the patient 900. As discussed with reference to FIG. 37(*a*), a subcutaneous path 1090 is created in the patient 900 with a hemostat 932.

The lead electrode assembly 100 is then captured by the lead electrode assembly manipulation tool 927. The paddle 1350 of the lead electrode assembly manipulation tool 927 is inserted into the pocket 1300 of the lead electrode assembly 100. The paddle 1350 is slid into the interior 1305 of the pocket via the opening 1310 of the pocket until it can go no further. At this point, the paddle 1350 touches the inner surface 1316 of the proximal end 1321 of the layer of material 1315.

The lead 21 of the lead electrode assembly 100 can then be pulled toward the handle 1142 of the lead electrode assembly manipulation tool 927 until it is taut. This acts to prevent the paddle 1350 of the lead electrode assembly manipulation tool 927 from sliding out of the pocket 1300 of the lead electrode assembly 100.

The lead electrode assembly manipulation tool 927 may then be used to place the lead electrode assembly 100 into the incision 905 of the patient as seen in FIG. 36. The lead electrode assembly manipulation tool 927 may then be used to move the electrode 107 to the termination point 1085 of the subcutaneous path 1090 created as discussed with reference to FIG. 37(*c*).

The lead electrode assembly 100 is then released from the lead electrode assembly manipulation tool 927. To achieve this, the lead 21 of the lead electrode assembly 100 is released so that the paddle 1350 can slide relative to the pocket 1300 of the lead electrode assembly 100. The lead electrode assembly manipulation tool 927 may then be extracted from the subcutaneous path 1090 leaving the lead electrode assembly 100 behind.

Alternately, a curved hemostat, such as the hemostat 930 discussed with reference to FIG. 37(*b*) could be inserted in the pocket 1300 of the lead electrode assembly 100. The hemostat could then be used to move the electrode 107 to the termination point 1085 of the subcutaneous path 1090 as discussed above.

Alternately, a curved hemostat, such as the hemostat 930 discussed with reference to FIG. 37(*b*) could be used to grip the pocket 1300 of the lead electrode assembly 100, and used to move the electrode 107 to the termination point 1085 of the subcutaneous path 1090 as discussed above.

Figure 44A:
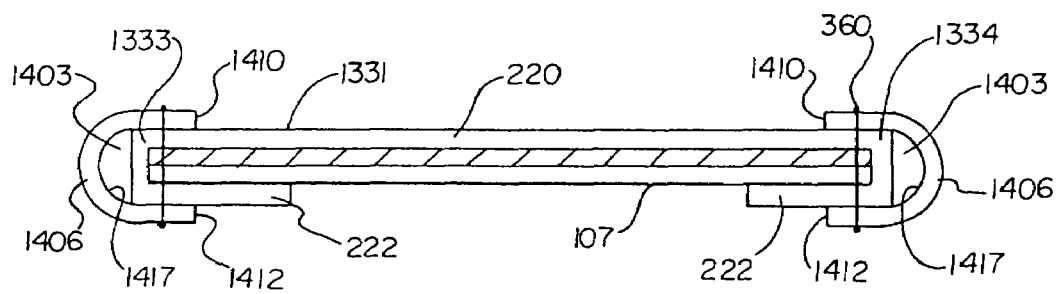
FIG. 44(a) is a cross-sectional rear plan view of a lead electrode assembly with a first channel guide and a second channel guide.
Figure 44B:
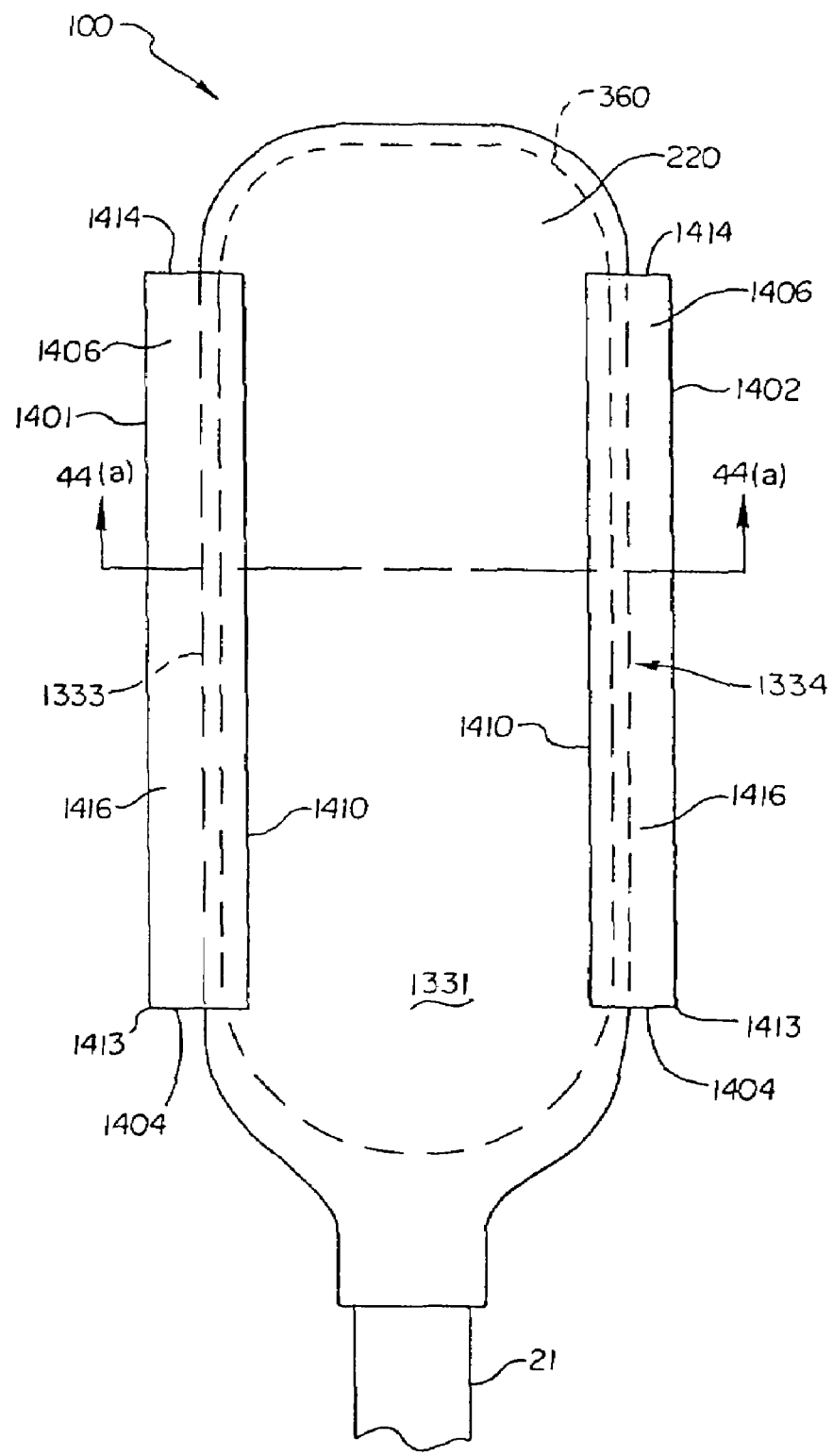
FIG. 44(b) is a top plan view of a lead electrode assembly with a first channel guide and a second channel guide.

FIGS. 44(*a*)-44(*b*) illustrate an alternative embodiment of the lead electrode assembly 100. This embodiment is substantially similar to the embodiment illustrated in FIGS. 43(*a*)-43(*c*). The backing layer 130 of this embodiment, however, lacks a pocket 1300. Moreover, the lead electrode assembly 100 of this embodiment further comprises a first channel guide 1401 and a second channel guide 1402.

FIG. 44(*a*) illustrates a cross-sectional rear plan view of the lead electrode assembly 100 of this embodiment. The first channel guide 1401 and a second channel guide 1402 each have an interior 1403 and an opening 1404.

The first channel guide 1401 and the second channel guide 1402 each comprise a strip of material 1406 attached to the molded cover 220.

The strip of material 1406 comprising the first channel guide 1401 is substantially rectangular in shape. The strip of material 1406 comprises a first side 1410 and a second side 1412. The first side 1410 and the second side 1412 of the strip of material 1406 are parallel to each other. In another embodiment, the first side 1410 of the strip of material 1406 is not parallel to the second side 1412.

The strip of material 1406 further comprises an inner surface 1417 and an outer surface 1416. The strip of material is positioned so that the inner surface 1417 of the first side 1410 faces the outer surface 1330 of the molded cover 220. The first side 1410 of the strip of material is attached to the first side 1333 of the top surface 1331 of the molded cover 220. The second side 1412 of the strip of material 1406 is attached to the skirt 222 of the molded cover 220.

The interior 1403 of the first channel guide is formed between the inner face 1417 of the strip of material 1406 and the outer surface 1330 of the molded cover 220.

The second channel guide is formed in substantially the same way on the second side 1334 of the molded cover 220.

FIG. 44(*b*) illustrates a top plan view of the lead electrode assembly of the embodiment of FIG. 44(*a*). The strip of material 1406 comprising the first channel guide 1401 is substantially rectangular in shape having a distal end 1413 and a proximal end 1414. The distal end 1413 and the proximal end 1414 of the strip of material 1406 are parallel to each other. In another embodiment, the distal end 1413 of the strip of material 1406 is not parallel to the proximal end 1414 of the strip of material 1406.

The opening 1404 of the first channel guide 1401 is formed by the distal end 1413 of the strip of material 1406 and the outer surface 1330 of the molded cover 220.

The first side 1410 and the second side 1412 (not shown) of the strip of material 1406 comprising the first channel guide 1401 are positioned so that they lie parallel to the first side 1333 (phantom view) of the molded cover 220.

The second channel guide 1402 is formed and mounted to the lead electrode assembly 100 in substantially the same way as the first channel guide 1401. The first side 1410 and the second side 1412 (not shown) of the strip of material 1406 comprising the second channel guide 1402 are positioned so that they lie parallel to the second side 1333 (phantom view) of the molded cover 220.

The strips of material 1406 are composed of polyurethane. In an alternate embodiment, the strips of material 1406 are composed of any polymeric material. The strips of material 1406 are fastened to the molded cover 220 with stitching 360.

In an alternate embodiment, the strips of material 1406 are made of molded silicone and attached to the molded cover 220 by fusing them to the molded cover 220. In an alternate embodiment, the first channel guide 1401 and the second channel guide 1402 are formed as part of the molded cover 220.

Figure 45A:
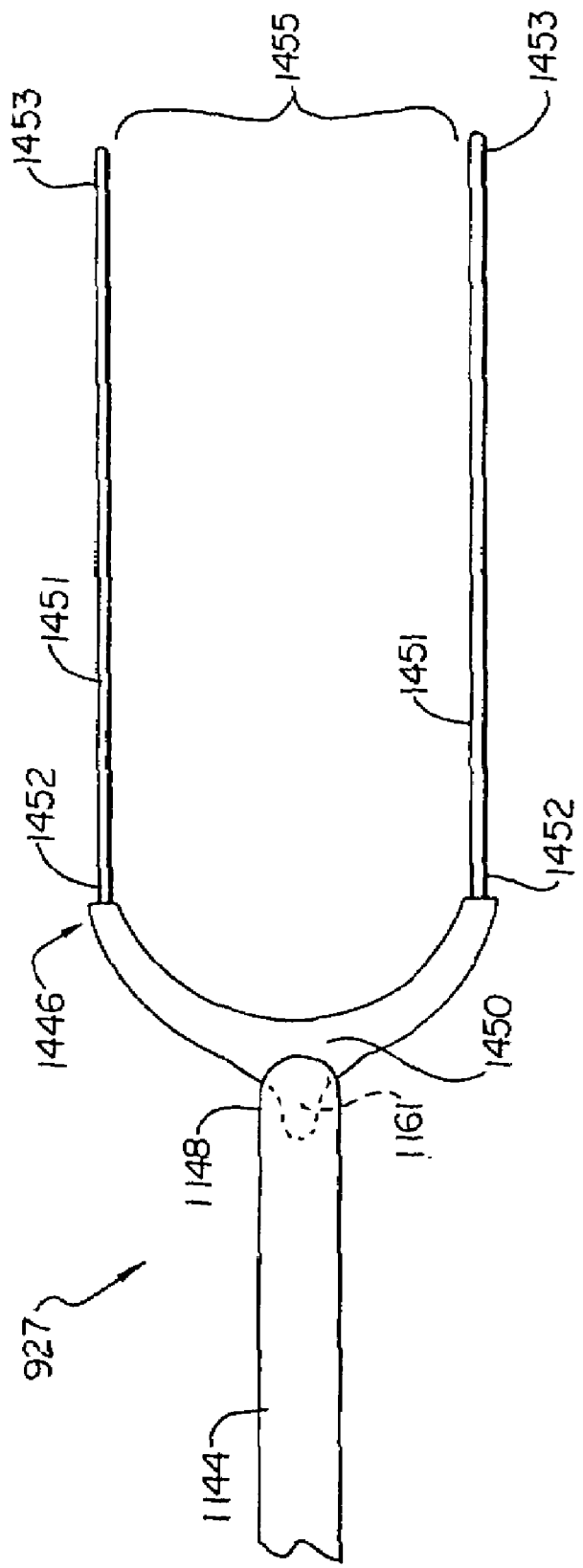
FIG. 45(a) is a top plan view of a lead electrode assembly manipulation tool with a channel guide fork.
Figure 45B:
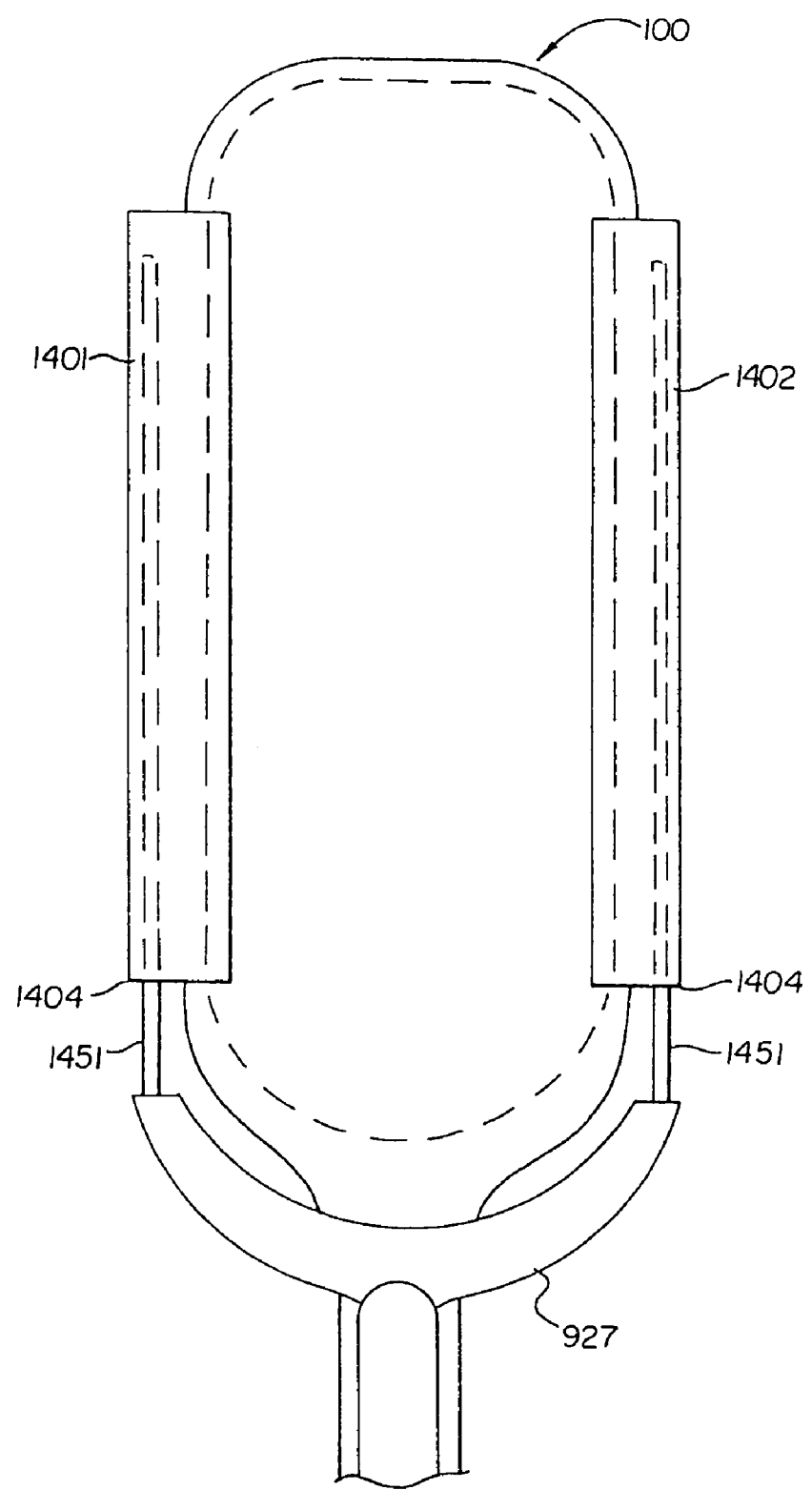
FIG. 45(b) is a top plan view of a lead electrode assembly with a first channel guide and a second channel guide captured by a lead electrode assembly manipulation tool with a channel guide fork.

FIGS. 45(*a*)-45(*b*) illustrate a lead electrode assembly manipulation tool 927. The lead electrode assembly manipulation tool 927 illustrated is useful for manipulating a lead electrode assembly 100 having a first channel guide 1401 and a second channel guide 1402 during the implantation of the lead electrode assembly 100 in a patient. Examples of such a lead electrode assembly 100 embodiments are shown in FIGS. 44(*a*)-44(*b*).

FIG. 45(*a*) illustrates a top plan view of a lead electrode assembly manipulation tool 927. The lead electrode assembly manipulation tool 927 in this embodiment comprises a handle 1142 (not shown), a rod 1144 and a channel guide fork 1446.

The rod 1144 and handle 1142 are substantially similar to the rod 1144 and handle 1142 of the lead electrode assembly manipulation tool 927 illustrated in FIGS. 40(*a*)-40(*d*). The handle 1142 is connected to the rod 1144.

The channel guide fork 1446 is attached to the distal end 1148 of the rod 1144. The channel guide fork 1446 comprises a pair of tines 1451 separated by a gap 1455 and a tine base 1450 having a tang 1161.

The pair of tines 1451 each has a proximal end 1452 and a distal end 1453. The proximal ends 1452 of the pair of tines 1451 are attached to the tine base 1450. The pair of tines 1451 has a substantially cylindrical form. The distal end 1453 of each of the pair of tines 1451 is rounded.

The length of the pair of tines 1451 is substantially equal to the length of the first side 1410 of the strips of material 1406 comprising the first channel guide 1401 and second channel guide 1402. In alternate embodiments, the length of the tines 1451 is substantially greater than or less than the length of the first side 1410 of the strips of material 1406 comprising the first channel guide 1401 and second channel guide 1402.

The tines are separated by a gap 1455 between the proximal ends 1452 of the pair of tines 1451. The pair of tines 1451 is substantially straight and substantially parallel to each other.

The tine base 1450 connects the pair of tines 1451 to the distal end 1148 of the rod 1144. The tine base 1450 comprises a tang 1161 (phantom view). The tang 1161 is inserted in a slot 1162 in the rod 1144. The tang 1161 is welded in the slot 1162 of the rod 1144.

The pair of tines 1451 comprising the channel guide fork 1446 is composed of steel and has a diameter of approximately 3 mm. The tine base 1450 comprising the channel guide fork 1446 is punched from a single strip of steel having a thickness of approximately 3 mm. The pair of tines 1451 is welded to the tine base 1450.

In other embodiments, the channel guide fork 1446 is composed of metal, a polymeric material, or any other material suitable for this purpose. In one embodiment, the handle 1142, the rod 1144 and the channel guide fork 1446 are all made from the same piece of material.

We now turn to FIG. 45(*b*) for a description of the use of the lead electrode assembly manipulation tool 927 in the implantation of a lead electrode assembly 100 into a patient.

As discussed with reference to FIG. 36, an incision 905 is made in the patient 900. As discussed with reference to FIG. 37(*a*), a subcutaneous path 1090 is created in the patient 900 with a hemostat 932.

The lead electrode assembly 100 is then captured by the lead electrode assembly manipulation tool 927. The pair of tines 1451 of the lead electrode assembly manipulation tool 927 is inserted into the openings 1404 in the first channel guide 1401 and second channel guide 1402.

The electrode 107 is placed into the gap 1455 between the tines of the channel guide fork 1446. The tines 1451 fit into the interior 1403 of the first channel guide 1401 and second channel guide 1402. The molded cover is slid toward the proximal end 1452 of the tines until it can go no further. The lead 21 of the lead electrode assembly 100 can then be pulled in toward the handle 1142 of the lead electrode assembly manipulation tool 927 until it is taut. This acts to prevent the lead electrode assembly 100 from sliding toward the distal end 1453 of the pair of tines 1451 of the channel guide fork 1446.

The lead electrode assembly manipulation tool 927 may then be used to place the lead electrode assembly 100 into the incision 905 of the patient as seen in FIG. 36. The lead electrode assembly manipulation tool 927 may then be used to move the electrode 107 through the termination point 1085 of the subcutaneous path 1090 created as discussed with reference to FIG. 37(*c*).

The lead electrode assembly 100 is then released from the lead electrode assembly manipulation tool 927. To achieve this, the lead 21 of the lead electrode assembly 100 is released so that the pair of tines 1451 of the channel guide fork 1446 of the lead electrode assembly manipulation tool 927 can slide relative to the first channel guide 1401 and second channel guide 1402 of the lead electrode assembly 100. The lead electrode assembly manipulation tool 927 may then be extracted from the subcutaneous path 1090 leaving the lead electrode assembly 100 behind.

Figure 46A:
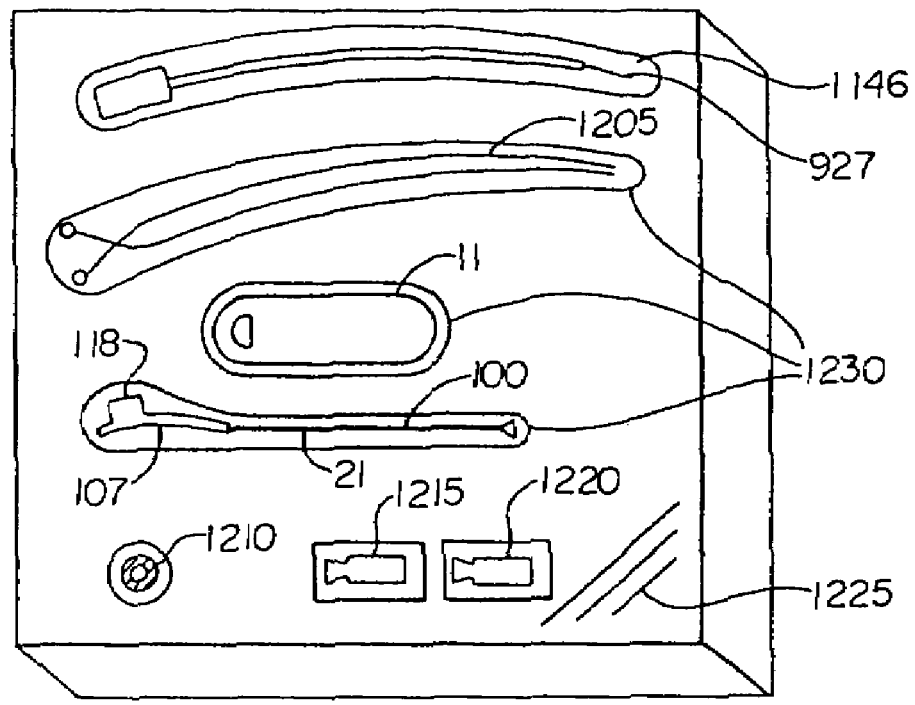
FIG. 46(a) is a perspective view of a subcutaneous implantable cardioverter-defibrillator kit.
Figure 46B:
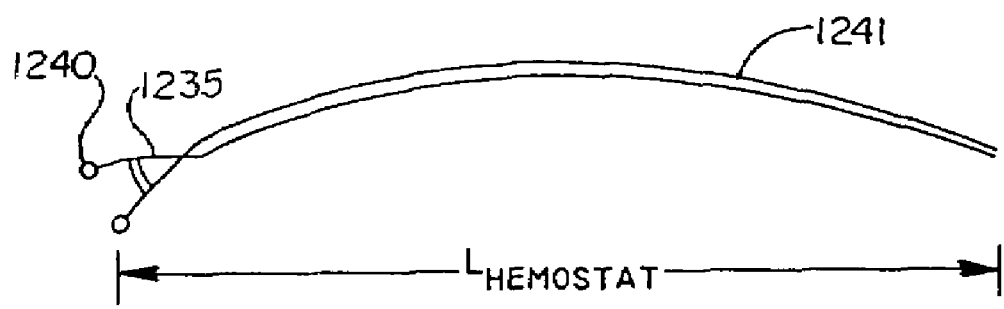
FIG. 46(b) is a perspective view of a hemostat illustrating the length measurement.

FIG. 46(*a*) illustrates a subcutaneous implantable cardioverter-defibrillator kit 1201 of the present invention. The kit comprises a group of items that may be used in implanting an S-ICD system in a patient. The kit 1201 comprises a group of one or more of the following items: an S-ICD canister 11, a lead electrode assembly 100, a hemostat 1205, a lead electrode assembly manipulation tool 927, a medical adhesive 1210, an anesthetic 1215, a tube of mineral oil 1220 and a tray 1200 for storing these items.

In one embodiment, the S-ICD canister 11 is the S-ICD canister 11 seen in and discussed with reference to FIG. 1.

The lead electrode assembly 100 is the lead electrode assembly 100 with a rail 1100, and discussed with reference to FIGS. 38(*b*) and 38(*c*). In alternate embodiments, the lead electrode assembly 100 is any lead electrode assembly 100 including an electrode 107 with an appendage 118; a pocket; or a first and second channel guide for positioning the electrode 107 during implantation.

The hemostat 1205 is a curved hemostat made of steel having a first end 1240 and a second end 1241. The hemostat 1205 has a length, measured between the first end 1240 and the second end 1241 as shown in FIG. 46(*b*) by dimension $L_{Hemostat}$. The length of the hemostat 1205, $L_{Hemostat}$, is approximately 75 cm. In an alternate embodiment, the hemostat 1205 is a length other than 75 cm. In an alternate embodiment, the hemostat 1205 is the enhanced hemostat seen in and discussed with reference to FIG. 36.

The lead electrode assembly manipulation tool 927 is the lead electrode assembly manipulation tool 927 with a rail fork 1146. In alternate embodiments, the lead electrode assembly manipulation tool 927 is any lead electrode assembly manipulation tool 927 including a paddle or a channel guide fork.

The medical adhesive 1210 comprises a roll of clear, 1-inch wide medical adhesive tape. As will be recognized, the medical adhesive could be a liquid adhesive, or any other adhesive substance.

The anesthetic 1215 is a one ounce tube of lidocaine gel. This can be used as a local anesthetic for the introduction of the lead electrode assembly 100 as discussed below. As will be recognized, the anesthetic could be any substance that has a pain-killing effect. Alternatively, one could use an injectable form of anesthetic inserted along the path of the lead.

The tube of mineral oil 1220 is a one-ounce tube of mineral oil. This can be used for oiling parts of the electrode connector block 17 seen in FIG. 1.

The tray 1200 is a box sized to fit the items of the kit 1201. The tray 1200 is composed of molded plastic. In another embodiment, the tray 1200 is a cardboard box. One skilled in the art will recognize that the tray 1200 may comprise any container capable of containing the items of the kit. In one embodiment, the tray is formed with recessed partitions 1230 that generally follow the outline of the items of the kit 1201 to be stored in the tray. In one embodiment, the tray 1200 has packaging material 1225 disposed over it, wherein the packing material 1225 provides a sanitary cover for the items of the kit 1201. The packaging material 1225 further acts to contain the items of the kit 1201.

In an alternate embodiment the kit 1201 comprises ten lead electrode assemblies 100 each comprising a lead 21 having a lead length, $I_{Lead}$, different from the others. In one embodiment, the lead lengths range between approximately 5 cm and approximately 52 cm with approximately a 10 cm difference between the lead length of each lead electrode assembly 100.

In an alternative embodiment, the kit 1201 comprises an S-ICD canister 11, a hemostat 1205 and an assortment of lead electrode assemblies 100 each comprising a lead 21 having a lead length, $1_{Lead}$, different from the others.

In one embodiment, the kit 1200 further comprises a tray 1201 and an assortment of lead electrode assemblies 100, each with an electrode 107 curved at a radius r different from the others.

In another embodiment, the kit 1200 includes components sized for surgery on a patient of a particular size. A kit 1200 for a 10 year old child, for example, includes an S-ICD canister 11 with a length of approximately 10 cm, a lead electrode assembly 100 with a lead length, $I_{Lead}$ of approximately 12 cm and a radius r of approximately 10 cm and hemostat 1205 with a hemostat length, $L_{Hemostat}$, of approximately 12 cm.

The S-ICD device and method of the present invention may be embodied in other specific forms without departing from the teachings or essential characteristics of the invention. The described embodiments are therefore to be considered in all respects as illustrative and not restrictive, the scope of the invention being indicated by the appended claims rather than by the foregoing description and all changes which come within the meaning and range of equivalency of the claims are therefore to be embraced therein.

What is claimed is:

1. An implantable lead electrode assembly comprising:
   an electrode having a proximal end and a distal end and a discharging face and an opposing face, one of the ends being configured for attaching to a lead;
   a backing layer attached to the opposing face of the electrode, the backing layer having a proximal end, a distal end, and sides extending therebetween;
   a fin formed by the backing layer, the fin extending laterally from a side of the backing layer; and
   a cover attached to the backing layer, the cover completely enclosing the backing layer and fin, as well as enclosing at least a portion of the discharging face of the electrode.

2. The implantable lead electrode assembly of claim 1, wherein the fin extends beyond an outside edge of the side of the backing layer and is in substantially the same plane as the backing layer.

3. The implantable lead electrode assembly of claim 1, wherein the fin has a proximal end and a distal end, wherein the proximal end of the fin is sloped.

4. The implantable lead electrode assembly of claim 1, further comprising a lead electrically coupled to the distal end the electrode.

5. The implantable lead electrode assembly of claim 1, further comprising a reinforcing polymer disposed between the fin and cover.

6. The implantable lead electrode assembly of claim 1, wherein the electrode has a perimeter and a main body portion, wherein the cover encloses the perimeter of the discharging face of the electrode but the main body portion of the discharging face is uncovered.

7. The implantable lead electrode assembly of claim 1, wherein the fin has a height in the range of about 1 mm to 10 mm.

8. The implantable lead electrode assembly of claim 7, wherein the fin has a width in the range of about 2 mm to 6 cm.

9. An implantable lead electrode assembly comprising:
   an electrode having a discharging face and an opposing face; and
   a backing layer attached to the opposing face of the electrode, the backing layer having a proximal end, a distal end, and sides extending therebetween, the backing layer having an extension forming a fin, the fin extending laterally from a side of the backing layer;
   wherein the electrode discharging face includes a main body portion and a perimeter, the implantable lead electrode assembly further comprising a cover attached to the backing layer, the cover completely enclosing the backing layer, fin, and perimeter of the discharging face of the electrode;
   wherein the main body portion of the discharging face is unobstructed.

10. The implantable lead electrode assembly of claim 9, wherein the fin extends beyond an outside edge of the side of the backing layer and in the same plane as the backing layer.

* * * * *

UNITED STATES PATENT AND TRADEMARK OFFICE
CERTIFICATE OF CORRECTION

PATENT NO. : 7,657,322 B2  Page 1 of 1
APPLICATION NO. : 11/429089
DATED : February 2, 2010
INVENTOR(S) : Bardy et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 706 days.

Signed and Sealed this

Thirtieth Day of November, 2010

David J. Kappos
*Director of the United States Patent and Trademark Office*